(12) United States Patent
Chiba et al.

(10) Patent No.: US 9,371,519 B2
(45) Date of Patent: Jun. 21, 2016

(54) COMPLEX TYPE SUGAR CHAIN HYDROLASE

(71) Applicant: National Institute of Advanced Industrial Science and Technology, Tokyo (JP)

(72) Inventors: Yasunori Chiba, Ibaraki (JP); Satoshi Murakami, Ibaraki (JP); Hisashi Narimatsu, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 5 days.

(21) Appl. No.: 14/349,569

(22) PCT Filed: Oct. 3, 2012

(86) PCT No.: PCT/JP2012/075650
§ 371 (c)(1),
(2) Date: Apr. 3, 2014

(87) PCT Pub. No.: WO2013/051608
PCT Pub. Date: Apr. 11, 2013

(65) Prior Publication Data
US 2014/0315246 A1 Oct. 23, 2014

(30) Foreign Application Priority Data

Oct. 3, 2011 (JP) .................. 2011-219169

(51) Int. Cl.
*C12N 9/24* (2006.01)
*C12N 9/42* (2006.01)
*C12P 21/00* (2006.01)

(52) U.S. Cl.
CPC ............ *C12N 9/2434* (2013.01); *C12N 9/2402* (2013.01); *C12P 21/005* (2013.01); *C12Y 302/01052* (2013.01); *C12Y 302/01096* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 2006/0148039 A1 | 7/2006 | Kobayashi et al. | |
| 2010/0121041 A1 | 5/2010 | Shoda et al. | |
| 2011/0014651 A1 | 1/2011 | Chiba et al. | |

FOREIGN PATENT DOCUMENTS

| | | | |
|---|---|---|---|
| EP | 0769550 A2 | 4/1997 | |
| EP | 1081221 A1 | 3/2001 | |
| JP | H0759587 A | 3/1995 | |
| JP | H09173083 A | 7/1997 | |
| JP | H09191875 A | 7/1997 | |
| JP | H11332568 A | 12/1999 | |
| JP | 4464269 B2 | 5/2010 | |
| WO | WO 99/61591 | * | 5/1999 |
| WO | 03/091431 A1 | 11/2003 | |
| WO | 2008111526 A1 | 9/2008 | |
| WO | 2009057813 A1 | 5/2009 | |

OTHER PUBLICATIONS

Basic Cloning Procedures, V. Berzins (ed), Springer Lab Manual, 1998, Springer: New York.*
Database UniProtKB/TrEMBL [online], Accession No. E7RB23, <http://www.uniprot.org/uniprot/E7RB23.txt?version=2>, May 31, 2011 uploaded, [retrieved on Oct. 11, 2012].
Database GenBank [online], Accession No. AJ306295, <http://www.ncbi.nlm.nih.gov/nuccore/AJ306295>, Nov. 14, 2006 uploaded, [retrieved on Oct. 22, 2012].
Database UniProtKB/TrEMBL [online], Accession No. Q96TVV7, <http://www.uniprot.org/uniprot/Q96TW7.txt?version=39>, Jun. 28, 2011 uploaded, [retrieved on Oct. 22, 2012].
Yamagishi, H. et al., Differentiation between brewing and non-brewing yeasts using a combination of PCR and RFLP, J. Appl. Microbiol., 1999, vol. 86, Issue 3, p. 505-513, Table 1.
Database GenBank [online], Accession No. CU928174, <http://www.ncbi.nlm.nih.gov/nuccore/CU928174>, Jan. 14, 2010 uploaded, [retrieved on Oct. 22, 2012].
Database UniprotKB/TrEMBL [online], Accession No. C5DRB8, <http://www.uniprot.org/uniprot/C5DRB8.txt?version=17, Jun. 28, 2011 uploaded, [retrieved on Oct. 22, 2012].
Haneda, Katsuji et al., Transglycosylation of intact sialo complex-type oligosaccharides to the N-acetylglucosamine moieties of glycopeptides by Mucor hiemalis endo-beta-N-acetylglucosaminidase, Carbohydr. Res., 1996, vol. 292, p. 61-70, Fig. 6.
Fan, Jian-Qiang et al., Enhanced transglycosylation activity of Arthrobacter protophormiae endo-beta-N-acetylglucosaminidase in media containing organic solvents, J. Biol. Chem., 1995, vol. 270, No. 30, p. 17723-17729, Table II.

(Continued)

*Primary Examiner* — Suzanne M Noakes
(74) *Attorney, Agent, or Firm* — Mintz Levin Cohn Ferris Glovsky and Popeo, P.C.; Peter F. Corless; Christopher R. Cowles

(57) ABSTRACT

The present invention provides a novel endo-β-N-acetylglucosaminidase (Endo-Om) using a transformant produced by cloning an endo-β-N-acetylglucosaminidase (Endo-Om) gene originated from a methylotrophic yeast *Ogataea minuta* IFO10746 strain. The Endo-Om according to the present invention has a specific activity 13-fold higher than that of known Endo-M and a Vmax value 55-fold higher than that of the known Endo-M, and is useful for the analysis of the structures of sugar chains, including complex type sugar chains, in glycoproteins and the modification of the sugar chains. Also provided are an endo-β-N-acetylglucosaminidase (Endo-Cp), an endo-β-N-acetylglucosaminidase (Endo-Pa) and an endo-β-N-acetylglucosamimidase (Endo Zr) which are produced from *Candida parapolymorpha* DL-1 ATCC26012 strain, *Pichia anomala* ATCC36904 strain and *Zygosaccharomyces rouxii* ATCC2623 strain, respectively, on the basis of an Endo-Om gene sequence, and each of which has a similar level of complex type sugar chain cleavage activity and a similar level of complex type sugar chain transfer activity to those of Endo-Om.

12 Claims, 18 Drawing Sheets

(56) References Cited

OTHER PUBLICATIONS

Fujita, Kiyotaka et al., Characterization of endo-beta-N-acetylglucosaminidase from alkaliphilic Bacillus halodurans C-125., Biosci. Biotechnol. Biochem., 2004, vol. 68, No. 5, p. 1059-1066, Fig. 3, 4.

Kuroda, Kousuke et al., Production of Man5GlcNAc2-type sugar chain by the methylotrophic yeast *Ogataea minuta*, FEMS Yeast Res., 2006, vol. 6, Issue 7, p. 1052-1062.

International Search Report from corresponding International Application Serial No. PCT/JP2012/075650, Oct. 30, 2012, 4 pages.

Takegawa, Kaoru, et al., Induction and Purification of Endo-β-N-Acetylglucosaminidase from Arthrobacter protophormiae Grown in Ovalbumin, Applied and Environmental Microbiology, Dec. 1989, p. 3107-3112.

Koide, Norio et al., Endo-β-N-acetylglucosaminidase Acting on Carbohydrate Moieties of Glycoproteins, the Journal of Biological Chemistry, vol. 249, No. 15, Issue of Aug. 10, pp. 4897-4904, 1974.

Elder, John H., et al.. endo-β-N-Acetylglucosaminidase F: Endoglycosidase from Flavobacterium meningosepticum that cleaves both high-mannose and complex glycoproteins, Proc. Natl. Acad. Sci. USA, vol. 79, pp. 4540-4544, Aug. 1982.

Robbins, Phillips W., et al., Primary Structure of the Streptomyces Enzyme Endo-B-N-acetylglucosaminidase H, The Journal of Biological Chemistry, vol. 259, No. 12, Issue of Jun. 25, pp. 7577-7583, 1984.

Kimura, Y., Structural and Functional Features of Plant Glycoprotein Glycans, Okayama University, Okayama, Japan, 2007, pp. 61-77.

Fujita, Kiyotaka, et al., Molecular cloning of Mucor hiemalis endo-b-N-acetylglucosaminidase and some properties of the recombinant enzyme, Archives of Biochemistry and Biophysics 432 (2004) 41-49.

Kadowaki, Setsu, et al., Purification and Characterization of a Novel Fungal Endo-β-N-acetylglucosaminidase Acting on Complex Oligosaccharides of Glycoproteins, Agric. Biol. Chem., 54(1), 97-106, 1990.

Tarentino, Anthony L., et al., Multiple Endoglycosidase F Activities Expressed by Flavobacterium meningosepticum Endoglycosidases F2 and F3, The Journal of Biological Chemistry, vol. 268, No. 13, Issue of May 5, pp. 9702-9708, 1993.

Goodfellow, Jonathan J. et al., An Endoglycosidase with Alternative Glycan Specificity Allows Broadened Glycoprotein Redmodelling, Journal of the American Chemical Society, 2012, 134, 8030-8033.

Kato, Toshihiko, et al., Identification of an endo-β-N-acetylglucosaminidase gene in Caenorhabditis elegans and its expression in *Escherichia coli*, Glycobiology, vol. 12 No. 10 pp. 581-587, 2002.

Partial supplementary European search report issued in corresponding European Application No. 12839059.8, Apr. 30, 2015, 6 pages.

First Office Action issued in corresponding Japanese Application No. 2013-537533, May 27, 2012, 7 pages.

Teresa Ruiz et al: "The sequence of a 15769 bp segment of Pichia anomala identifies the SEC61 and FBP1 genes and five new open reading frames", Yeast, vol. 18, Jun. 1, 2001, pp. 1187-1195, XP055182857, *sequence Q96TW7* & Database UniProt [Online].

J.-L. Souciet et al: Comparative genomics of protoploid Saccaromycetaceae, Genome Research, vol. 19, No. 10, Jun. 12, 2009, pp. 1696-1709, XP055182860, ISSN: 1088-9051, DOI: 10.1101/gr.091546.109 *sequence C5DRB8* & Database UniProt [Online].

Kenji Yamamoto, Microbial Endoglycosidases for Analyses of Oligosaccharide Chains in Glycoproteins, JB Review, J. Biochem. vol. 116, No. 2, 1994, pp. 229-235.

* cited by examiner

FIG. 1

7.5% Gel, CBB stain.

A. Optimum pH

B. Optimum temperature

COMPLEX TYPE SUGAR CHAIN HYDROLASE

CROSS-REFERENCES TO RELATED APPLICATIONS

This application is a 35 U.S.C. §371 U.S. national entry of International Application PCT/JP2012/075650 (WO 2013/051608) having an International filing date of Oct. 3, 2012, which claims under 35 U.S.C. §119(a) the benefit of Japanese Application No. 2011-219169, filed Oct. 3, 2011, the entire contents of all of which applications are incorporated herein by reference.

TECHNICAL FIELD

The present invention relates to a complex type sugar chain hydrolase and its gene.

BACKGROUND ART

Glycoproteins are found in eukaryotes from microorganisms such as yeast to human, and are reported to be found in several bacteria in recent years. The functions of their sugar chains relate to stability and protease resistance of protein, and are necessary for folding for the formation of a higher-order structure. In addition, glycoproteins are known to control the interaction between proteins, and bind to lectin on the cell surface to cause signal transduction. The analysis of these glycoproteins requires cleavage of the sugar chains and determination of their structure. Peptide: N-glycanase and endo-β-N-acetylglucosaminidases are known as the enzymes which cleaves the N-linked sugar chain attached to asparagine residues. The latter endo-β-N-acetylglucosaminidases are enzymes which cleave the bond between chitobiose molecules at the reducing ends of N-type sugar chains, and known examples include *Arthrobacter*-derived Endo-A (Non Patent Literature 1, Patent Literature 4), *Streptococcus pneumoniae*-derived Endo-D (Non Patent Literature 2), *Flavobacterium*-derived Endo-F (Non Patent Literature 3), *Streptomyces plicatus*-derived Endo-H (Non Patent Literature 4), *Mycosphaerella*-derived endo-β-N-acetylglucosaminidase (Patent Literature 3), rice-derived Endo-Os (Non Patent Literature 5), *Mucor hiemalis*-derived Endo-M (Patent Literatures 1, 2, and 5, Non Patent Literatures 6 and 7) are known. Many of them have digestion activity between chitobiose molecules, and transglycosidase activity for transferring sugar chains. More specifically, they efficiently catalyze the reaction including the action on the N-type sugar chain of a glycoprotein to cut out the sugar chain, and transfer of the sugar chain to a carbohydrate or complex carbohydrate as the acceptor. Accordingly, endo-β-N-acetylglucosaminidases are enzymes useful not only for the analysis of the sugar chain structure of glycoproteins, and also for the modification of glycoproteins and glycolipids, preparation of neoglycoproteins, and homogenization of the sugar chain of glycoproteins.

The asparagine-linked sugar chains of glycoproteins showing major biological activity are classified into high-mannose type (mannan type sugar chain), hybrid type, and complex type sugar chains, according to their structures. However, among the endo-β-N-acetylglucosaminidases, Endo-M, Endo-F2, Endo-F3, Endo-S, and Endo-CE are reported to have activity for cleaving the complex type sugar chain.

The properties of Endo-M are studied in detail, and its substrate specificity is 4.4% for the biantennary complex type sugar chain (agalacto biantennary PA-sugar) when the activity for the high-mannose type Man8GlcNAc2 is set at 100% (Non Patent Literature 6). In addition, there is a description that Endo-M can cleave the triantennary and asialo tetraantennary N-type sugar chains (Non Patent Literature 7), but the activity for asialo triantennary and asialo tetraantennary was not detected in the enzyme activity measurement using a PA sugar chain (Non Patent Literature 6). Endo-M also cannot cleave the biantennary PA-sugar chain to which core fucose is attached.

Endo-F2 is an enzyme derived from *Elizabethkingia miricola*, and hydrolyzes high-mannose- and biantennary complex type sugar chains, but has no activity for hydrolyzing a hybrid type sugar chain (Non Patent Literature 8). Endo-F3 is also an enzyme derived from *Elizabethkingia miricola*, and hydrolyzes a biantennary or triantennary complex type sugar chain, but has no activity for hydrolyzing high-mannose and hybrid type sugar chains (Non Patent Literature 8). Endo-S is an enzyme derived from *Streptococcus pyogenes*, and hydrolyzes a biantennary complex type sugar chain, but has no activity for hydrolyzing high-mannose type and hybrid type sugar chains (Non Patent Literature 9). Endo-CE is an enzyme derived from *Caenorhabditis elegans*, and hydrolyzes high-mannose and biantennary complex type sugar chains. However, it is unknown whether it cleaves a hybrid type sugar chain (Non Patent Literature 10).

Regarding the modification of a complex type sugar chain, based on prior art findings, the substrate specificity of transglycosidase activity of endo-β-N-acetylglucosaminidases is the same as their digestion activity, so only these enzymes can transfer complex type sugar chains to acceptors.

The provision of an endo-β-N-acetylglucosaminidase having different substrate specificity from Endo-M is desired for the analysis of the sugar chain structure of a glycoprotein and the synthesis of glycoproteins having various sugar chains including complex type carbohydrate sugar chains, and the enzyme having high specific activity for a complex type sugar chain is also desired.

CITATION LIST

Patent Literatures

Patent Literature 1: JP 11-332568 A
Patent Literature 2: JP 7-59587 A
Patent Literature 3: JP 9-191875 A
Patent Literature 4: JP 9-173083 A
Patent Literature 5: WO 2008/111526 A
Patent Literature 6: WO 2009/057813 A
Patent Literature 7: JP 4464269 B1

Non Patent Literatures

Non Patent Literature 1: Takegawa K et al., (1989) Appl Environ Microbiol. 55: p3107-3112
Non Patent Literature 2: Koide N and Muramatsu T, (1974) J Biol. Chem. 249: p4897-4904
Non Patent Literature 3: Elder J H and Alexander S, (1982) PNAS U.S.A. 79: 4540-4544
Non Patent Literature 4: Robbins P W et al., (1984) J Biol. Chem. 259: p7577-7583
Non Patent Literature 5: Kimura Y, (2007) In Comprehensive Glycoscience 3: p61-78
Non Patent Literature 6: Fujita et al., (2004) Arch Biochem Biophy. 432: p41-49
Non Patent Literature 7: Kadowaki S et al., (1990) Agric Biol. Chem. 54: p97-106

Non Patent Literature 8: Tarentino A L et al., (1993) Biol. Chem. 268: p9702-9708

Non Patent Literature 9: Goodfellow J J et al., (2012) Am Chem. Sci. 134: p8030-8033

Non Patent Literature 10: Kato T et al., (2002) Glycobiology 12: p581-587

SUMMARY OF INVENTION

Technical Problem

The present invention is intended to solve the problems with the prior art method for liberating a sugar chain from these asparagine-linked glycoproteins, and the transfer of a complex type sugar chain using transglycosidase activity. More specifically, the present invention is intended to obtain a novel enzyme which is different from the previously reported endo-β-N-acetylglucosaminidases, and provide endo-β-N-acetylglucosaminidase which is different from Endo-M in the substrate specificity and specific activity, and the method for producing the same.

Solution to Problem

During the study on the properties of the methylotrophic yeast *Ogataea minuta* IFO10746 strain, the inventors found that high endo-β-N-acetylglucosaminidase (Endo-Om) activity is present in the culture supernatant. Therefore, they isolated the Endo-Om gene from the yeast, and determined the nucleotide sequence and corresponding amino acid sequence (SEQ ID Nos. 1 and 2). The Endo-Om of the present invention has low homology (identity) with any of the sequences of known endo-β-N-acetylglucosaminidases, and is a novel enzyme having an identity at the amino acid level of 33.9% with the known Endo-M derived from the genus *Mucor*, 8.8% with Endo-F2, 9.0% with Endo-F3, 14.7% with Endo-S, 18.9% with Endo-CE, and about 53.9% with the hypothetical protein derived from the genus *Candida*, which has the closest sequence on the database. *O. minuta* strain was transformed using the Endo-Om gene derived from the *O. minuta* strain, and an Endo-Om gene-overexpressing strain was prepared, thereby increasing endo-β-N-acetylglucosaminidase activity. Endo-β-N-acetylglucosaminidase was isolated from this overexpressing strain, its properties were determined, and thus the present invention has been accomplished.

The endo-β-N-acetylglucosaminidase (Endo-Om) of the present invention has the following enzymological and physicochemical properties;

(1) Action; acts on an asparagine-linked glycoprotein in an endo-type, and liberates a sugar chain.

(2) Substrate specificity;

1) cleaves the N,N'-diacetylchitobiose moiety, which is contained in the core structure of the high-mannose type, hybrid type, and biantennary complex type sugar chains, to form an oligosaccharide.

2) when the activity for the high-mannose type M8A-PA sugar chain is set at 100%, the activity for the high-mannose type M6B-PA sugar chain is about 103%, and the activity for a biantennary complex type sugar chain (agalacto biantennary PA-sugar) is about 15%.

(3) Optimal pH; about 5.5

(4) Optimal temperature; 45 to 50° C.

(5) Gene; 2,319 bp (homology of 33% with the amino acid sequence of Endo-M)

(6) Molecular weight; 87,398 Da (from the amino acid sequence)

(7) Specific activity when 1 mM of the biantennary complex type sugar chain (NGA2-Asn-Fmoc) is used as the substrate; 0.80 µmol/min/mg (about 13 times the specific activity of Endo-M (0.06 vol/min/mg))

(8) Km to the biantennary complex type sugar chain (NGA2-Asn-Fmoc); 5539 µM, Vmax; 3.88 µmol/min/mg (31 times the Km of Endo-M (176 µM), 55 times the Vmax of Endo-M (0.070 µmol/min/mg))

(9) Transglycosidase activity; when the biantennary complex type (NGA2-Asn-Fmoc) was used as the sugar donor, and the acceptor was p-nitrophenylglucose, significant transglycosidase activity was confirmed.

When the activity for the high-mannose type M8A-PA sugar chain is set at 100%, the Endo-Om of the present invention has activity for the high-mannose type M6B-PA sugar chain is about 103%, and the activity for a biantennary complex type sugar chain (agalacto biantennary PA-sugar) is about 15%. Therefore, it has different substrate specificity from well-known Endo-M, and has specific activity as high as 13 times that of Endo-M and Vmax as high as 55 times that of Endo-M. The use of the overexpression system developed by the present invention allows high-volume production of high quality enzymes at a low cost.

Furthermore, based on the amino acid sequence of the Endo-Om of the present invention, BLAST search was carried on the NCBI amino acid sequence database of closely-related yeasts, and several genes partially having high homology region were detected. These yeast-derived genes were cloned and their sequences were determined, and the expression products were purified to obtain enzyme solutions. The enzymatic activity of these enzyme solutions was studied in detail, and it was found that the enzymes derived from the *Candida parapolymorpha* DL-1 strain belonging to the genus *Candida*, *Pichia anomala* belonging to the genus *Pichia*, and *Zygosaccharomyces rouxii* belonging to the genus *Zygosaccharomyces* are novel enzymes having high endo-β-N-acetylglucosaminidase (ENGase) activity as Endo-Om. These enzymes were named "Endo-Cp", "Endo-Pa", and "Endo-Zr", respectively.

More specifically, aspects of the present invention are as follows.

[1] A protein having endo-β-N-acetylglucosaminidase activity containing any of the following amino acid sequences (1) to (5):

(1) the amino acid sequence set forth in SEQ ID NO. 1, 5, 9, or 13;

(2) the amino acid sequence obtained by deletion, substitution, insertion and/or addition of one or several amino acids in the amino acid sequence set forth in SEQ ID NO. 1, 5, 9, or 13, (3) the amino acid sequence having an identity of 70% or more with the amino acid sequence set forth in SEQ ID NO. 1, 5, 9, or 13;

(4) the amino acid sequence coded by the nucleotide sequence set forth in SEQ ID NO. 2, 6, 10, or 14;

(5) the amino acid sequence coded by the nucleotide sequence of the polynucleotide which hybridizes with the polynucleotide including the complementary sequence of the nucleotide sequence set forth in SEQ ID NO. 2, 6, 10, or 14 under stringent conditions.

[2] The polynucleotide which codes the protein having endo-β-N-acetylglucosaminidase activity of [1].

[3] A polynucleotide containing any of the following nucleotide sequences (1) to (6):

(1) the nucleotide sequence set forth in SEQ ID NO. 2, 6, 10, or 14 in containing polynucleotide;

(2) the polynucleotide which hybridizes with the polynucleotide including the complementary sequence of the nucleotide sequence set forth in SEQ ID NO. 2, 6, 10, or 14 under stringent conditions, and codes a protein having endo-β-N-acetylglucosaminidase activity;

(3) the polynucleotide which is amplified by the primer set containing the nucleotide sequences set forth in SEQ ID NO. 3 and 4, has an identity of 70% or more with SEQ ID NO. 2, and codes a protein having endo-β-N-acetylglucosaminidase activity;

(4) the polynucleotide which is amplified by the primer set containing the nucleotide sequences set forth in SEQ ID NO. 7 and 8, has an identity of 70% or more with SEQ ID NO. 6, and codes a protein having endo-β-N-acetylglucosaminidase activity;

(5) the polynucleotide which is amplified by the primer set containing the nucleotide sequences set forth in SEQ ID NO. 11 and 12, has an identity of 70% or more with SEQ ID NO. 10, and codes a protein having endo-β-N-acetylglucosaminidase activity.

(6) the polynucleotide which is amplified by the primer set containing the nucleotide sequences set forth in SEQ ID NO. 15 and 16, has an identity of 70% or more with SEQ ID NO. 14, and codes a protein having endo-β-N-acetylglucosaminidase activity.

[4] A vector for expressing a protein having endo-β-N-acetylglucosaminidase activity, containing the polynucleotide of [2] or [3].

[5] A transformant for expressing a protein having endo-β-N-acetylglucosaminidase activity into which the vector of [4] is introduced.

[6] The transformant of [5], wherein the transformant is hosted by yeast cells selected from any of the yeasts *Ogataea minuta*, *Candida parapolymorpha*, *Pichia anomala*, and *Zygosaccharomyces rouxii*.

[7] A method for producing a protein having endo-β-N-acetylglucosaminidase activity, including the use of the transformant of [5] or [6].

[8] A method for digesting an asparagine-linked sugar chain from a glycoprotein, including the use of the protein having endo-β-N-acetylglucosaminidase activity of [1].

[9] A method for transferring an asparagine-linked sugar chain to any acceptor molecule, including the use of the protein having endo-β-N-acetylglucosaminidase activity of [1].

Advantageous Effects of Invention

The endo-β-N-acetylglucosaminidase Endo-Om in the present invention has an identity of as low as 33.9% with known Endo-M at the amino acid sequence level, and has different substrate specificity in that the activity for a high-mannose type M6B-PA sugar chain is about 103%, and the activity for a biantennary complex type sugar chain (agalacto biantennary PA-sugar) is about 15%, when the activity for the high-mannose type M8A-PA sugar chain is set at 100%, and high specific activity and Vmax which are 13 times and 55 times those of Endo-M, respectively. Therefore, the Endo-Om is evidently a novel enzyme, but it has marked functions of Endo-M, so that it hydrolyzes a complex type sugar chain and has transglycosidase activity for a complex type sugar chain. In addition, Endo-Om has markedly high specific activity and maximum reaction speed, and thus is highly expected to be useful in the analysis and glycosylation of the sugar chain structure including the complex type sugar chains in glycoproteins. In addition, the use of the overexpression system developed by the present invention allows high-volume production of the high quality Endo-Om enzyme at a low cost.

Endo-Cp, Endo-Pa, and Endo-Zr, which are other endo-β-N-acetylglucosaminidase of the present invention also have similar complex type sugar chain cleavage activity and complex type sugar chain transfer activity, and are expected to have similar uses as those of Endo-Om.

BRIEF DESCRIPTION OF DRAWINGS

FIG. 1 shows the amino acid sequence and nucleotide sequence of the Endo-Om gene. In FIG. 1, the underlined part indicates the sequence highly conserved in GH family 85 ENGase; and ■ indicates the presumed amino acid residue at the active center.

In FIG. 2, the values in parentheses show the length of the amino acid sequence and homology with Endo-Om. Accession No., *Ashbya gossypii*, NP_986144; *Mucor hiemalis* (Endo-M), BAB43869; *Candida parapolymorpha* DL-1 (*Hansenula polymorpha* DL-1), EFW94296; *Pichia anomala*, CAC69142; *Zygosaccharomyces rouxii*, xP_002495262.

FIG. 8 shows the nucleotide sequence and amino acid sequence of the Endo-Cp gene. In FIG. 8, the underlined part indicates the sequence highly conserved in GH family 85 ENGase; and ■ indicates the presumed amino acid residue at the active center.

FIG. 12 shows the nucleotide sequence and amino acid sequence of the Endo-Pa gene. In FIG. 12, the underlined part indicates the sequence highly conserved in GH family 85 ENGase; and ■ indicates the presumed amino acid residue at the active center.

FIG. 16 shows the nucleotide sequence and amino acid sequence of the Endo-Zr gene. In FIG. 16, the underlined part indicates the sequence highly conserved in GH family 85 ENGase; and ■ indicates the presumed amino acid residue at the active center.

DESCRIPTION OF EMBODIMENTS

Figure 2:
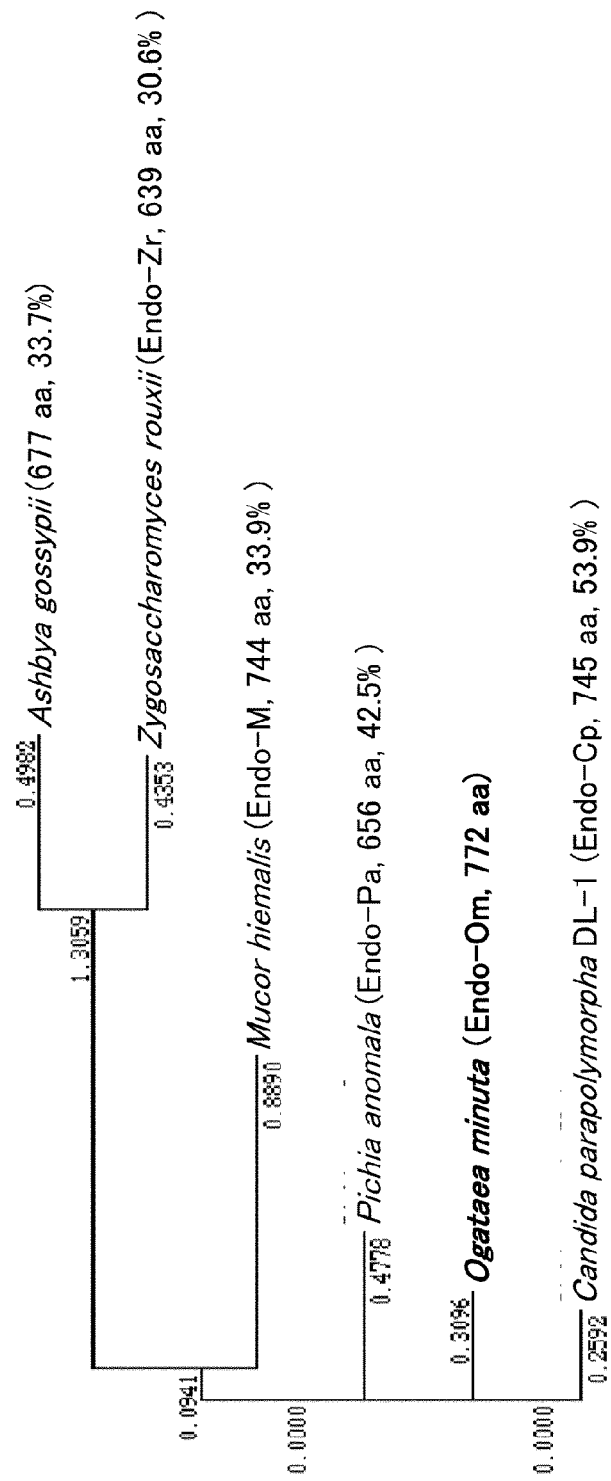
FIG. 2 shows the dendrogram of Endo-Om and ENGases derived from species close to yeast.

1. Endo-β-N-Acetylglucosaminidase of the Present Invention 1-1. About "Endo-Om"

(1) Enzymological and Physicochemical Properties;
(1) action; acts on an asparagine-linked glycoprotein in an endo type, and liberates a sugar chain.
(2) Substrate specificity;
1) cleaves the N,N'-diacetylchitobiose moiety, which is contained in the core structure of the high-mannose type, hybrid type, and biantennary complex type sugar chains, to form an oligosaccharide.
2) when the activity for the high-mannose type M8A-PA sugar chain is set at 100%, the activity for a high-mannose type M6B-PA sugar chain is about 103%, and the activity for a biantennary complex type sugar chain (agalacto biantennary PA-sugar) is about 15%.
(3) Optimal pH; about 5.5
(4) Optimal temperature; 45 to 50° C.
(5) Gene; 2,319 bp (homology of 33% with the amino acid sequence of Endo-M)
(6) Molecular weight; 87,398 Da (from the amino acid sequence)
(7) Specific activity when 1 mM of the biantennary complex type sugar chain (NGA2-Asn-Fmoc) is used as the substrate; 0.80 μmol/min/mg
(about 13 times the specific activity of Endo-M (0.06 μmol/min/mg))
(8) Km for the biantennary complex type sugar chain (NGA2-Asn-Fmoc); 5539 μM, Vmax 3.88 μmol/min/mg
(31 times the Km of Endo-M (176 μM), 55 times the Vmax of Endo-M (0.070 μmol/min/mg))
(9) Transglycosidase activity; significant transglycosidase activity was confirmed when the biantennary complex type (NGA2-Asn-Fmoc) was used as the sugar donor, and the acceptor was p-nitrophenylglucose.
(2) Amino Acid Sequence and Nucleotide Sequence The endo-β-N-acetylglucosaminidase (Endo-Om) of the present invention can be expressed as a protein having endo-β-N-acetylglucosaminidase activity containing any of the following amino acid sequences (1) to (5). The protein is preferably derived from a yeast, and particular preferably derived from an Ogataea yeast.

(1) the amino acid sequence set forth in SEQ ID No. 1;
(2) the amino acid sequence obtained by deletion, substitution, insertion and/or addition of one or several amino acids in the amino acid sequence set forth in SEQ ID No. 1 ("several amino acids" means 1 to 20, preferably 1 to 10, and more preferably 1 to 5 amino acids);
(3) the amino acid sequence having an identity of at least 70% with the amino acid sequence set forth in SEQ ID No. 1 (the amino acid sequence preferably has an identity of 80% or more, more preferably 85% or more, and even more preferably 90% or more);
(4) the amino acid sequence coded by the nucleotide sequence set forth in SEQ ID NO. 2;
(5) the amino acid sequence coded by the nucleotide sequence of the polynucleotide which hybridizes with the polynucleotide including the complementary sequence of the nucleotide sequence set forth in SEQ ID NO. 2 under stringent conditions;

wherein the "stringent conditions" mean the conditions of an ordinary hybridization operation described in, for example, edited by T. Maniatis et al, Molecular Cloning: A Laboratory Manual 2nd ed. (1989) Cold Spring Harbor Laboratory, wherein a so-called specific hybrid is formed, and no nonspecific hybrid is formed. For example, the conditions mean the incubation in 6×SSC (1×SSC is 0.15 M NaCl, 0.015 M sodium citrate, pH 7.0), 0.5% SDS, 5×Denhardt's [Denhardt's, 0.1% bovine serum albumin (BSA), 0.1% polyvinyl pyrrolidone, and 0.1% Ficoll 400] and 100 μg/ml salmon sperm DNA, at 50° C. for 4 hours to overnight. When the increase in the stringency is desired, the incubation is carried out in 2×SSC, 0.5% SDS, 25% formamide, 5×Denhardt's, and 100 μg/ml salmon sperm DNA, at 55° C. for 4 hours to overnight. Commonly, the conditions allow less than 15%, preferably less than 10% of mismatch in the entire nucleotide sequence.

Further, the protein having Endo-Om activity of the present invention is including a yeast-derived amino acid sequence which is detected by the BLAST search through the NCBI GenBank amino acid sequence database at a homology of 30% or more, preferably 40% or more, more preferably 50% or more, even more preferably 70% or more, most preferably 80% or more with the amino acid sequence set forth in SEQ ID No. 1, and is a protein having endo-β-N-acetylglucosaminidase activity. In particular, it is preferably the gene derived from a genus Ogataea yeast.

Alternatively, it can be expressed as a protein which is coded by the gene including the yeast-derived nucleotide sequence detected by the BLAST search through the NCBI GenBank nucleotide sequence database at a homology of 30% or more, preferably 40% or more, more preferably 50% or more, even more preferably 70% or more, and most preferably 80% or more with the nucleotide sequence set forth in SEQ ID NO. 2, and has endo-β-N-acetylglucosaminidase activity.

In addition, the Endo-Om gene of the present invention can be expressed as a polynucleotide which codes the protein having endo-β-N-acetylglucosaminidase activity containing any of the above-described amino acid sequences (1) to (5), and also can be expressed as any of the following polynucleotides (1) to (3), wherein the polynucleotide is preferably derived from a yeast, particularly preferably derived from a genus Ogataea yeast:

(1) the polynucleotide containing the nucleotide sequence set forth in SEQ ID NO. 2;

(2) the polynucleotide which hybridizes with the polynucleotide including the complementary sequence of the nucleotide sequence set forth in SEQ ID NO. 2 under stringent conditions, and codes a protein having endo-β-N-acetylglucosaminidase activity;

(3) the polynucleotide which is amplified by the primer set containing the nucleotide sequences set forth in SEQ ID NO. 3 and 4, has an identity of 70% or more with SEQ ID NO. 2, and codes a protein having endo-β-N-acetylglucosaminidase activity (the nucleotide sequence preferably has an identity of 80% or more, more preferably 85% or more, and even more preferably 90% or more);

As shown in FIG. 2, the endo-β-N-acetylglucosaminidase (Endo-Om) of the present invention has specific sequence which has an identity of only 33.9% at the amino acid sequence level with the well-known Endo-M derived of the genus *Mucor*, and has an identity of about 53.9% at the amino acid level with the hypothetical protein derived from the genus *Candida* at the closest position in the database. Therefore, when the polypeptide is including an amino acid sequence having an identity of 70% or more, preferably 80% or more, and even more preferably 90% or more with the amino acid sequence set forth in SEQ ID No. 1, it has an extremely high probability of having Endo-Om activity, and the polynucleotide including the nucleotide sequence having an identity of 70% or more, preferably 80% or more, and more preferably 90% or more with the nucleotide sequence set forth in SEQ ID NO. 2 also has a high probability of being an Endo-Om gene. The homology search of polypeptides and polynucleotides can be carried out by, for example, using the FASTA or BLAST program for DNA Databank of JAPAN (DDBJ).

(3) Hydrolysis Activity for Various Sugar Chains

Using the Endo-Om partially purified enzyme solution of the present invention, hydrolysis activity for various PA-labeled commercially available sugar chains (TaKaRa-Bio Inc.) were measured, and the results are shown in the following (Table 1) together with the measurements in a literature on Endo-M (Non Patent Literature 6). The hydrolysis activity at that time was calculated from the peak area ratio between the PA-labeled sugar chain and its hydrolysate as substrates in HPLC, and the relative activity for the various sugar chains was calculated, with the hydrolysis activity for the sugar chain with an M8A structure set at 100%.

TABLE 1

| Substrate | Endo-Om | Endo-M* |
|---|---|---|
| 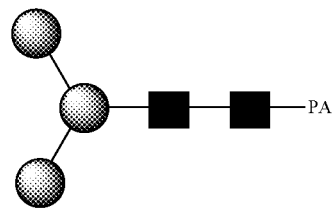<br>M3B | 55.9% | 19.5% |
| 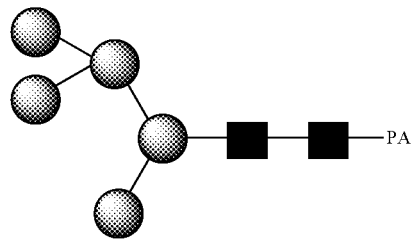<br>M5A | 13.7% | 15.4% |
| 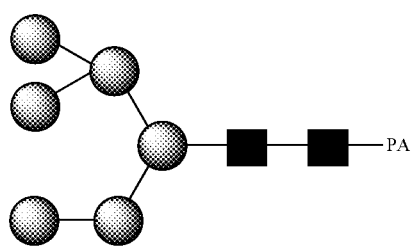<br>M6B | 103% | 74.0% |

TABLE 1-continued
| Substrate | Endo-Om | Endo-M* |
|---|---|---|
| 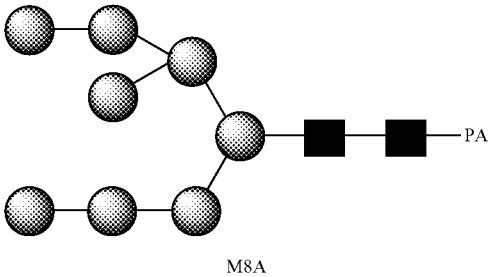 M8A | 100% | 100% |
| 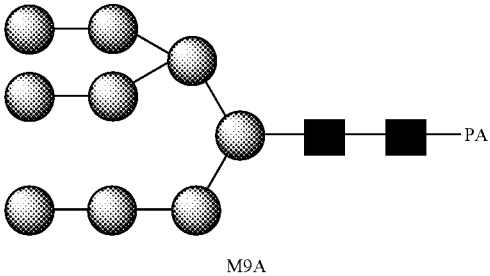 M9A | 81.3% | 66.5% |
| 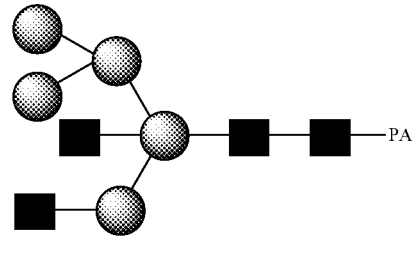 hybrid-type (bisecting GlcNAc) | 0.8% | — |
| 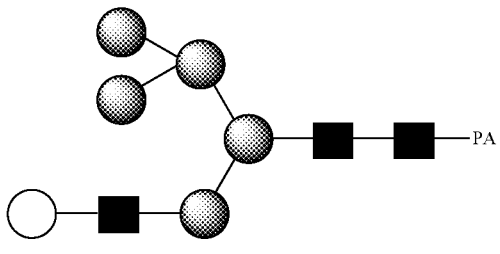 hibrid-type | 5.9% | — |
| 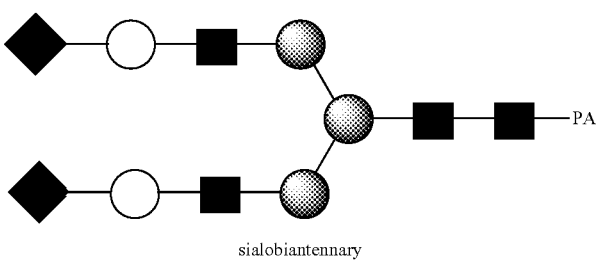 sialobiantennary | 1.6% | 7.0% |

TABLE 1-continued

| Substrate | Endo-Om | Endo-M* |
|---|---|---|
| 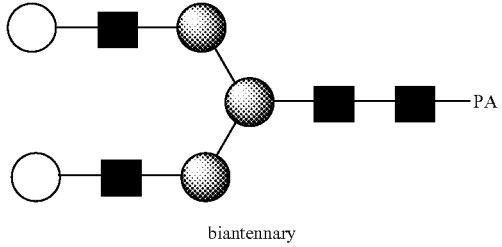 biantennary | 4.6% | 13.3% |
| 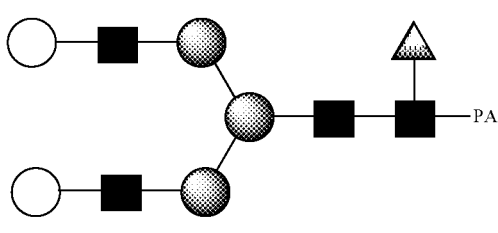 fucosyl biantennary | ND | ND |
| 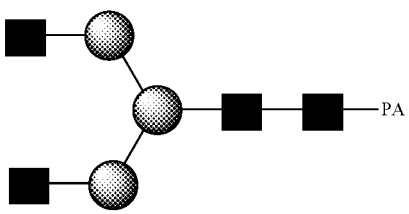 agalacto biantennary | 15.1% | 4.4% |
| 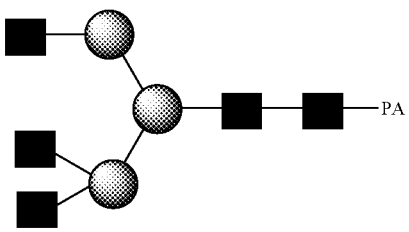 agalacto triantennary | ND | ND |
| 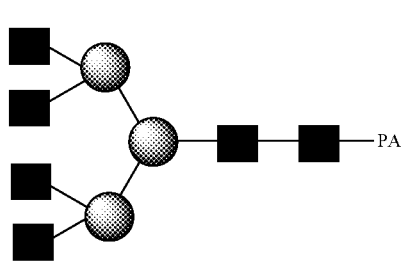 agalacto tetraantennary | ND | ND |

The relative activity was calculated using M8A as the substrate.

*Relative activity of Endo-M was cited from Fujita et al. (2004) Arch Biochem Biophy, 432: p 41-49

- ⦿: Mannose,
- ■: GlcNAc,
- ○: Galactose,
- ▲: Fucose,
- ♦: Neu5Ac,

ND: Not detected.

The above-described results (Table 1) indicate that Endo-Om has as high hydrolysis activity as Endo-M for a high-mannose sugar chain, and further hydrolyzes a hybrid type sugar chain and a biantennary complex type sugar chain. On the other hand, it cannot hydrolyze a triantennary or more highly branched complex type sugar chain, and a sugar chain having a core fucose structure. In addition, it shows different reactivity for several sugar chains from Endo-M, and exhibits particularly higher reactivity for the sugar chains having an agalacto biantennary, M3B, M6B, or M9A structure than Endo-M.

(4) Transglycosidase Activity

Endo-Om has activity for transferring a sugar chain to any acceptor molecule, like Endo-M. Examples of the typical acceptor molecules include monosaccharides and derivatives thereof such as a glucose and GlcNAc, and glycopeptides and glycoproteins having them. The sugar chain to be transferred is an asparagine-linked sugar chain, and may be a chemically synthesized sugar chain or cleaved sugar chain.

Figure 7:
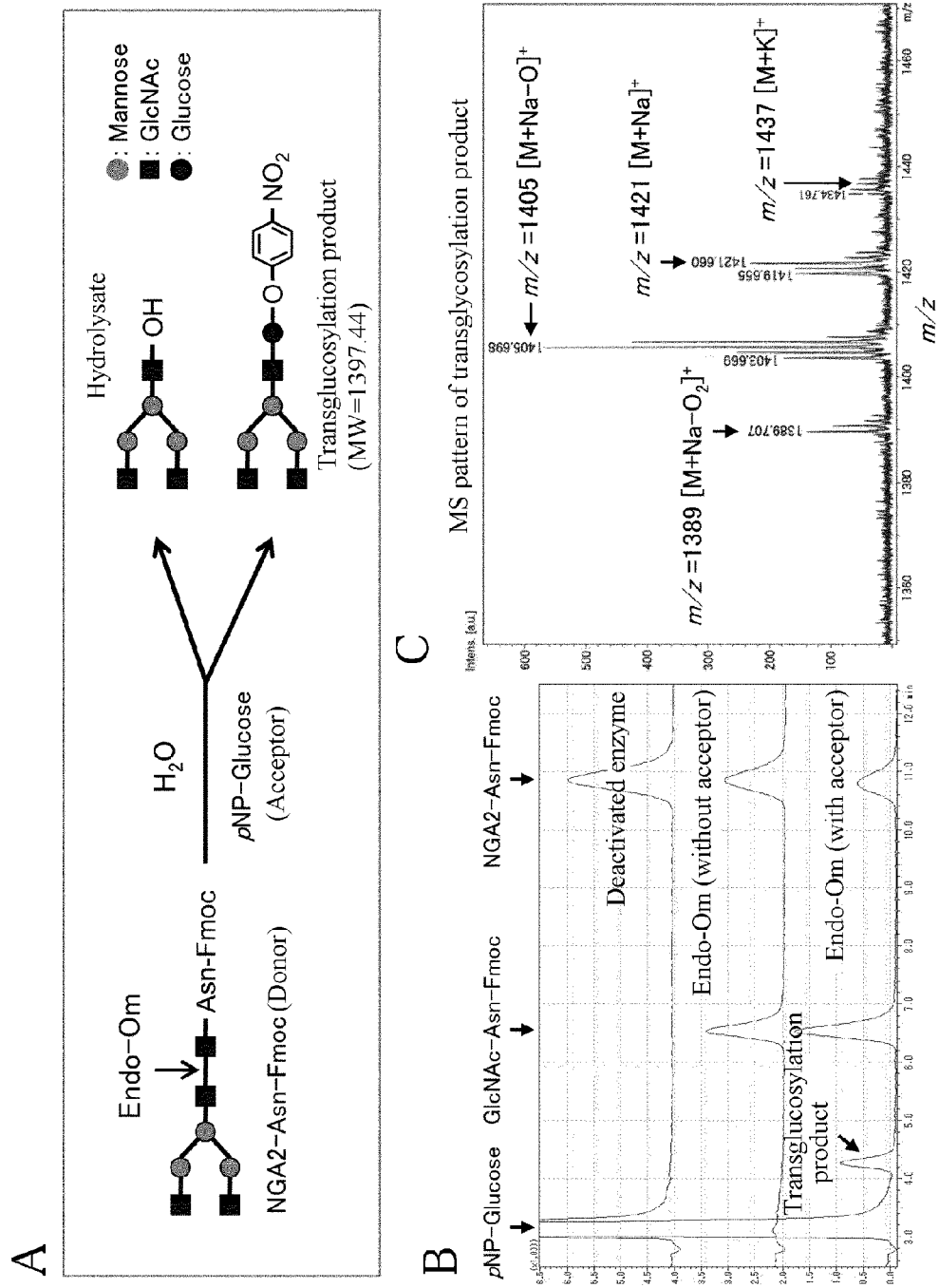
FIG. 7 shows the results of detection of the presence or absence of transglycosidase activity of Endo-Om. A: transglycosylation of Endo-Om; B: detection of sugar transfer activity by HPLC; C: MS patterns of the transglycosylation product

The transglycosidase activity of Endo-Om was detected by incubating the reaction solution containing a biantennary complex type sugar chain as the substrate, acceptor molecules (p-nitrophenylglucose), and an Endo-Om partially purified enzyme solution at 30° C. for 3 hours, and then subjecting it to HPLC after the completion of the reaction; a new peak different from the hydrolysate was detected, and was identified by MS analysis to be a transglycosylation product including an acceptor molecule to which a biantennary complex type sugar chain is added (FIG. 7).

1-2. About "Endo-Cp"

(1) Enzymological and Physicochemical Properties;

(1) action; acts on an asparagine-linked glycoprotein in an endo type, and liberates a sugar chain.

(2) substrate specificity;

1) cleaves the N,N'-diacetylchitobiose moiety, which is contained in the core structure of the high-mannose type, hybrid type, and biantennary complex type sugar chains, to form an oligosaccharide;

2) when the activity for the high-mannose type M8A-PA sugar chain is set at 100%, the activity for a high-mannose type M6B-PA sugar chain is about 172%, and the activity for a biantennary complex type sugar chain (agalacto biantennary PA-sugar) is about 7.0%;

(3) Optimal pH; about 5.5

(4) Optimal temperature; 60° C.

(5) Gene; 2,238 bp (homology of 38% with the amino acid sequence of Endo-M)

(6) Molecular weight; 86,500 Da (from the amino acid sequence)

(7) Transglycosidase activity; when the biantennary complex type (NGA2-Asn-Fmoc) was used as the sugar donor, and the acceptor was p-nitrophenylglucose, significant transglycosidase activity was confirmed.

(2) Amino Acid Sequence and Nucleotide Sequence

The endo-β-N-acetylglucosaminidase of the present invention (Endo-Cp) can be expressed as a protein containing any of the following amino acid sequences (1) to (5) and having endo-β-N-acetylglucosaminidase activity; the protein is preferably derived from a yeast, more preferably a *Candida* yeast, and most preferably *Candida* parapolymorpha:

(1) the amino acid sequence set forth in SEQ ID NO. 5;

(2) the amino acid sequence obtained by deletion, substitution, insertion and/or addition of one or several amino acids in the amino acid sequence set forth in SEQ ID No. 5 ("several amino acids" means 1 to 20, preferably 1 to 10, and more preferably 1 to 5 amino acids);

(3) the amino acid sequence having an identity of at least 70% with the amino acid sequence set forth in SEQ ID No. 5 (the amino acid sequence preferably has an identity of 80% or more, more preferably 85% or more, and even more preferably 90% or more);

(4) the amino acid sequence coded by the nucleotide sequence set forth in SEQ ID NO. 6; and (5) the amino acid sequence coded by the nucleotide sequence of the polynucleotide which hybridizes with the polynucleotide including the complementary sequence of the nucleotide sequence set forth in SEQ ID NO. 6 under stringent conditions (wherein the "stringent conditions" are as described above).

Furthermore, the protein having Endo-Cp activity of the present invention is including the yeast-derived amino acid sequence detected by the BLAST search through the NCBI GenBank amino acid sequence database at a homology of 30% or more, preferably 40% or more, more preferably 50% or more, even more preferably 70% or more, and most preferably 80% or more with the amino acid sequence set forth in SEQ ID NO. 5, and has endo-β-N-acetylglucosaminidase activity.

In particular, it is preferably derived from a genus *Candida* yeast, particularly *Candida parapolymorpha*.

Alternatively, it can be expressed as a protein which is coded by the gene detected by the BLAST search through the NCBI GenBank nucleotide sequence database at a homology of 30% or more, preferably 40% or more, more preferably 50% or more, even more preferably 70% or more, and most preferably 80% or more with the nucleotide sequence set forth in SEQ ID NO. 6, and has endo-β-N-acetylglucosaminidase activity.

The Endo-Cp gene of the present invention can be expressed as a polynucleotide which codes the protein containing any of the above-described amino acid sequences (1) to (5) and having endo-β-N-acetylglucosaminidase activity, and also can be expressed as a polynucleotide of any of the following (1) to (3); the polynucleotide is preferably derived from a yeast, and particularly preferably derived from a genus *Candida* yeast:

(1) the polynucleotide containing the nucleotide sequence set forth in SEQ ID NO. 6, (2) the polynucleotide which hybridizes with the polynucleotide including the complementary sequence of the nucleotide sequence set forth in SEQ ID NO. 6 under stringent conditions, and codes a protein having endo-β-N-acetylglucosaminidase activity;

(3) the polynucleotide which is amplified by the primer set containing the nucleotide sequences set forth in SEQ ID NO. 7 and 8, has an identity of 70% or more with SEQ ID NO. 6, and codes a protein having endo-β-N-acetylglucosaminidase activity (the nucleotide sequence preferably has an identity of 80% or more, more preferably 85% or more, and even more preferably 90% or more).

As shown in FIG. 2, the endo-β-N-acetylglucosaminidase of the present invention (Endo-Cp) has an identity of 53.9% at the amino acid sequence level with the "Endo-Om" of the present invention derived from *Ogataea minuta*, and has identities of 42.8% and 31.9% with the "Endo-Pa" enzyme derived from *Pichia anomala* and the "Endo-Zr" enzyme derived from *Zygosaccharomyces rouxii*, which were found at the same time, respectively. The identity with the well-known "Endo-M" derived from the genus *Mucor* is only 38.2% at the amino acid sequence level. In this manner, the "Endo-Cp" of the present invention has a specific sequence.

Therefore, when the polypeptide is including an amino acid sequence having an identity of 70% or more, preferably 80% or more, and even more preferably 90% or more with the amino acid sequence set forth in SEQ ID No. 5, it has an extremely high probability of having Endo-Cp activity, and the polynucleotide including the nucleotide sequence having an identity of 70% or more, preferably 80% or more, and more preferably 90% or more with the nucleotide sequence set forth in SEQ ID NO. 6 also has a high probability of being an Endo-Cp gene. The homology search of polypeptides and polynucleotides can be carried out by, for example, using the FASTA or BLAST program for DNA Databank of JAPAN (DDBJ).

(3) Hydrolysis Activity for Various Sugar Chains

Using the Endo-Cp partially purified enzyme solution of the present invention, hydrolysis activity for various PA-labeled commercially available sugar chains (TaKaRa-Bio Inc.) were measured, and the results are shown in the following (Table 2) together with the measurements in a literature on Endo-M (Non Patent Literature 6). The hydrolysis activity at that time was calculated from the peak area ratio between the PA-labeled sugar chain and its hydrolysate as substrates in HPLC, and the relative activity for the various sugar chains was calculated, with the hydrolysis activity for the sugar chain with an M8A structure set at 100%.

TABLE 2

| Substrate | Endo-Cp | Endo-M* |
|---|---|---|
| 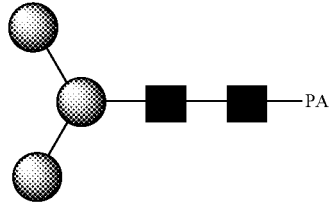 M3B | 37.3% | 19.5% |
| 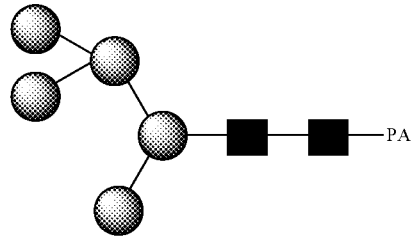 M5A | 15.1% | 15.4% |
| 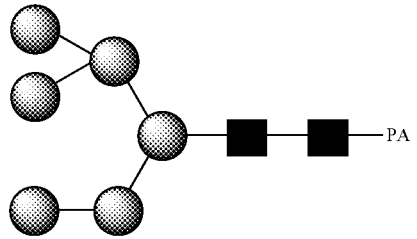 M6B | 172% | 74.0% |
| 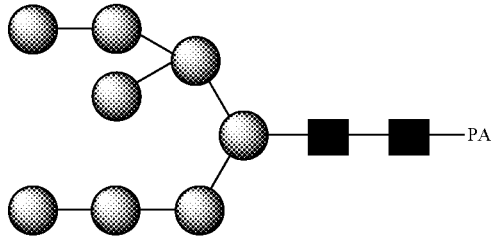 M8A | 100% | 100% |

TABLE 2-continued

| Substrate | Endo-Cp | Endo-M* |
|---|---|---|
| M9A | 21.6% | 66.5% |
| hybrid-type (bisecting GlcNAc) | 0.4% | — |
| hibrid-type | 4.7% | — |
| sialobiantennary | 1.1% | 7.0% |
| biantennary | 3.1% | 13.3% |

TABLE 2-continued

| Substrate | Endo-Cp | Endo-M* |
|---|---|---|
| 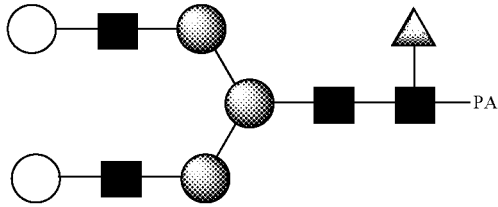fucosyl biantennary | ND | ND |
| 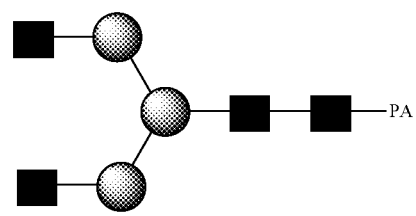agalacto biantennary | 7.0% | 4.4% |
| 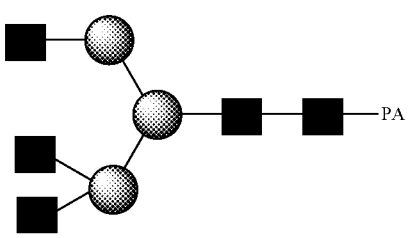agalacto triantennary | ND | ND |
| 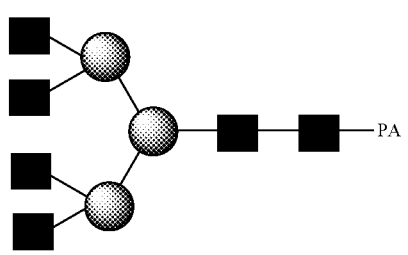agalacto tetraantennary | ND | ND |

The relative activity was calculated using M8A as the substrate.
*Relative activity of Endo-M was cited from Fujita et al. (2004) Arch Biochem Biophy, 432: p 41-49

⬢: Mannose,
■: GlcNAc,
○: Galactose,
▲: Fucose,
♦: Neu5Ac,
ND: Not detected.

The above-described results (Table 2) indicate that Endo-Cp has as high hydrolysis activity as Endo-M for a high-mannose sugar chain, and further hydrolyzes a hybrid type sugar chain and a biantennary complex type sugar chain. On the other hand, it cannot hydrolyze a triantennary or more highly branched complex type sugar chain and a sugar chain having a core fucose structure. In addition, it exhibits higher reactivity for almost all sugar chains than Endo-M. In addition, it shows different reactivity for several sugar chains from Endo-M, and exhibits particularly higher reactivity for sugar chains having an agalacto biantennary, M3B, and M6B structures than Endo-M.

(4) Transglycosidase Activity

Endo-Cp has activity for transferring a sugar chain to any acceptor molecule, like Endo-M. Examples of the typical acceptor molecules include monosaccharides and derivatives thereof such as a glucose and GlcNAc, and glycopeptides and glycoproteins having them. The sugar chain to be transferred is an asparagine-linked sugar chain, and may be a chemically synthesized sugar chain or cleaved sugar chain.

Figure 11:
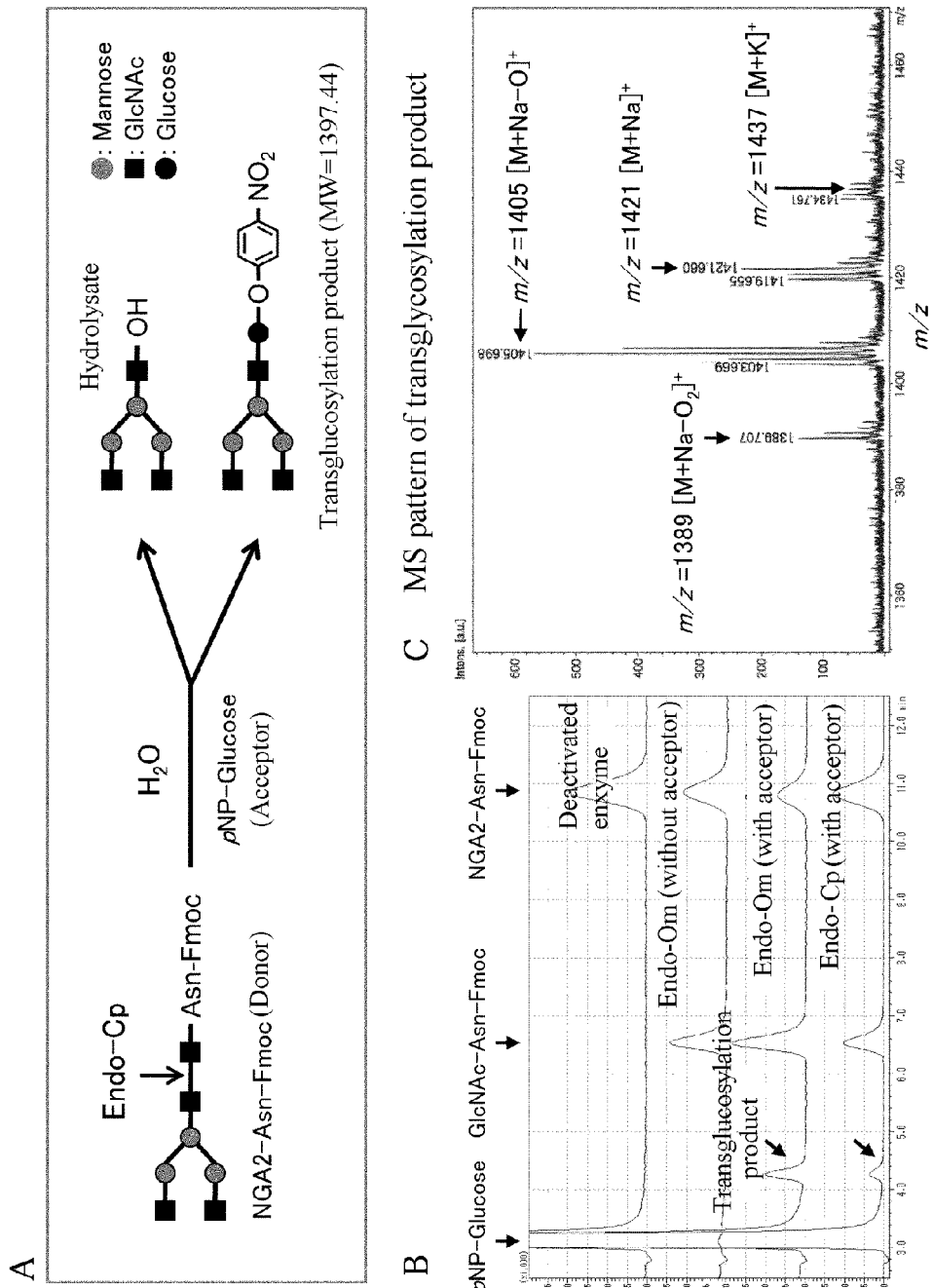
FIG. 11 shows the results of the detection of the presence or absence of transglycosidase activity of Endo-Cp. A: transglycosylation of Endo-Om; B: detection of sugar transfer activity by HPLC; and C: MS patterns of the transglycosylation product.

The transglycosidase activity of Endo-Cp was detected by incubating the reaction solution containing a biantennary complex type sugar chain as the substrate, acceptor molecules (p-nitrophenylglucose), and an Endo-Cp partially purified enzyme solution at 30° C. for 3 hours, and then subjecting it to HPLC after the completion of the reaction; a new peak different from the hydrolysate was detected, and was identified by MS analysis to be a transglycosylation product including an acceptor molecule to which a biantennary complex type sugar chain is added (FIG. 11).

1-3. About "Endo-Pa"

(1) Enzymological and Physicochemical Properties;
(1) Action; acts on an asparagine-linked glycoprotein in an endo type, and liberates a sugar chain.
(2) Substrate specificity;
1) cleaves the N,N'-diacetylchitobiose moiety, which is contained in the core structure of the high-mannose type, hybrid type, and biantennary complex type sugar chains, to form an oligosaccharide;
2) when the activity for the high-mannose type M8A-PA sugar chain is set at 100%, the activity for the high-mannose type M6B-PA sugar chain is about 140%, and the activity for a biantennary complex type sugar chain (agalacto biantennary PA-sugar) is about 54.4%.
(3) Optimal pH; about 5.0 to 5.5
(4) Optimal temperature; 40° C.
(5) Gene; 1,971 bp (homology of 33.0% with the amino acid sequence of Endo-M)
(6) Molecular weight; 76,050 Da (from the amino acid sequence)
(7) Transglycosidase activity; when the biantennary complex type (NGA2-Asn-Fmoc) was used as the sugar donor, and the acceptor was p-nitrophenylglucose, significant transglycosidase activity was confirmed.
(2) Amino Acid Sequence and Nucleotide Sequence The endo-β-N-acetylglucosaminidase of the present invention (Endo-Pa) can be expressed as a protein containing any of the following amino acid sequences (1) to (5) and having endo-β-N-acetylglucosaminidase activity; the protein is preferably derived from a yeast, more preferably a *Pichia* yeast, and most preferably *Pichia anomala*:

(1) the amino acid sequence set forth in SEQ ID NO. 9;
(2) the amino acid sequence obtained by deletion, substitution, insertion and/or addition of one or several amino acids in the amino acid sequence set forth in SEQ ID No. 9 ("several amino acids" means 1 to 20, preferably 1 to 10, and more preferably 1 to 5 amino acids);
(3) the amino acid sequence having an identity of at least 70% with the amino acid sequence set forth in SEQ ID No. 9 (the amino acid sequence preferably has an identity of 80% or more, more preferably 85% or more, and even more preferably 90% or more);
(4) the amino acid sequence coded by the nucleotide sequence set forth in SEQ ID NO. 10; and
(5) the amino acid sequence coded by the nucleotide sequence of the polynucleotide which hybridizes with the polynucleotide including the complementary sequence of the nucleotide sequence set forth in SEQ ID NO. 10 under stringent conditions (wherein the "stringent conditions" are as described above).

Furthermore, the protein having Endo-Pa activity of the present invention is including the yeast-derived amino acid sequence detected by the BLAST search through the NCBI GenBank amino acid sequence database at a homology of 30% or more, preferably 40% or more, more preferably 50% or more, even more preferably 70% or more, and most preferably 80% or more with the amino acid sequence set forth in SEQ ID NO. 10, and has endo-β-N-acetylglucosaminidase activity. In particular, the gene is preferably derived from a *Pichia* yeast, and particularly preferably derived from *Pichia anomala*.

Alternatively, it can be expressed as a protein which is coded by the gene including the yeast-derived nucleotide sequence detected by the BLAST search through the NCBI GenBank nucleotide sequence database at a homology of 30% or more, preferably 40% or more, more preferably 50% or more, even more preferably 70% or more, and most preferably 80% or more with the nucleotide sequence set forth in SEQ ID NO. 10, and has endo-β-N-acetylglucosaminidase activity.

In addition, the Endo-Pa gene of the present invention can be expressed as a polynucleotide which codes the protein having endo-β-N-acetylglucosaminidase activity containing any of the above-described amino acid sequences (1) to (5), and also can be expressed as any of the following polynucleotides (1) to (3), wherein the polynucleotide is preferably derived from a yeast, particularly preferably derived from a *Pichia* yeast, and most preferably derived from *Pichia anomala*:

(1) the polynucleotide containing the nucleotide sequence set forth in SEQ ID NO. 10;
(2) the polynucleotide which hybridizes with the polynucleotide including the complementary sequence of the nucleotide sequence set forth in SEQ ID NO. 10 under stringent conditions, and codes a protein having endo-β-N-acetylglucosaminidase activity;
(3) the polynucleotide which is amplified by the primer set containing the nucleotide sequences set forth in SEQ ID NO. 11 and 12, has an identity of 70% or more with SEQ ID NO. 10, and codes a protein having endo-β-N-acetylglucosaminidase activity (the nucleotide sequence preferably has an identity of 80% or more, more preferably 85% or more, and even more preferably 90% or more);

As shown in FIG. 2, the endo-β-N-acetylglucosaminidase (Endo-Pa) of the present invention has an identity of 42.5% at the amino acid sequence level with the "Endo-Om" of the present invention derived from *Ogataea minuta*, and has identities of 42.8% and 30.2% with the "Endo-Cp" enzyme derived from *Candida* parapolymorpha DL-1 and the "Endo-Zr" enzyme derived from *Zygosaccharomyces rouxii*, which were found at the same time, respectively. The identity with the well-known "Endo-M" derived from the genus *Mucor* is only 33.0% at the amino acid sequence level. In this manner, the "Endo-Pa" of the present invention has a specific sequence. Therefore, when the polypeptide is including an amino acid sequence having an identity of 70% or more, preferably 80% or more, and even more preferably 90% or more with the amino acid sequence set forth in SEQ ID No. 9, it has an extremely high probability of having Endo-Pa activity, and the polynucleotide including the nucleotide sequence having an identity of 70% or more, preferably 80% or more, and more preferably 90% or more with the nucleotide sequence set forth in SEQ ID NO. 10 also has a high probability of being an Endo-Pa gene. The homology search of polypeptides and polynucleotides can be carried out by, for example, using the FASTA or BLAST program for DNA Databank of JAPAN (DDBJ).

(3) Hydrolysis Activity for Various Sugar Chains

Using the Endo-Pa partially purified enzyme solution of the present invention, hydrolysis activity for various PA-labeled commercially available sugar chains (TaKaRa-Bio Inc.) were measured, and the results are shown in the following (Table 3) together with the measurements in a literature on Endo-M (Non Patent Literature 6). The hydrolysis activity at that time was calculated from the peak area ratio between the PA-labeled sugar chain and its hydrolysate as substrates in HPLC, and the relative activity for the various sugar chains was calculated, with the hydrolysis activity for the sugar chain with an M8A structure set at 100%.

TABLE 3

| Substrate | Endo-Pa | Endo-M* |
|---|---|---|
| 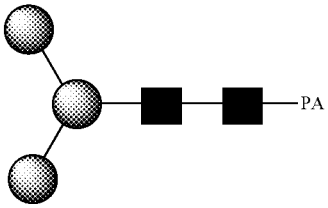 M3B | 152% | 19.5% |
| 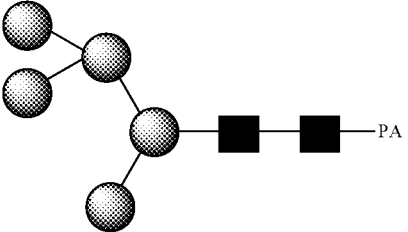 M5A | 94.3% | 15.4% |
| 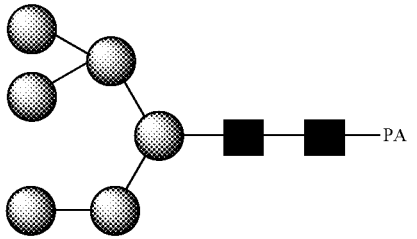 M6B | 140% | 74.0% |
| 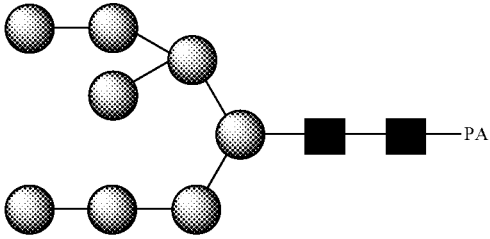 M8A | 100% | 100% |
| 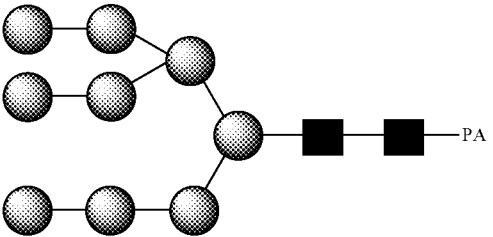 M9A | 115% | 66.5% |

TABLE 3-continued

| Substrate | Endo-Pa | Endo-M* |
|---|---|---|
| hybrid-type (bisecting GlcNAc) | 4.0% | — |
| hibrid-type | 35.4% | — |
| sialobiantennary | 36.3% | 7.0% |
| biantennary | 40.5% | 13.3% |
| fucosyl biantennary | ND | ND |
| agalacto biantennary | 54.4% | 4.4% |

TABLE 3-continued

| Substrate | Endo-Pa | Endo-M* |
|---|---|---|
| agalacto triantennary | ND | ND |
| agalacto tetraantennary | ND | ND |

The relative activity was calculated using M8A as the substrate.
*Relative activity of Endo-M was cited from Fujita et al. (2004) Arch Biochem Biophy, 432: p 41-49.
◉: Mannose,
■: GlcNAc,
○: Galactose,
▲: Fucose,
♦: Neu5Ac,
ND: Not detected.

The above-described results (Table 3) indicate that Endo-Pa has as high hydrolysis activity as Endo-M for a high-mannose sugar chain, and further hydrolyzes a hybrid type sugar chain and a biantennary complex type sugar chain. On the other hand, it cannot hydrolyze a triantennary or more highly branched complex type sugar chain and a sugar chain having a core fucose structure. In addition, it exhibits higher reactivity for almost all sugar chains than Endo-M.

(4) Transglycosidase Activity

Endo-Pa has activity for transferring a sugar chain to any acceptor molecule, like Endo-M. Examples of the typical acceptor molecules include monosaccharides and derivatives thereof such as a glucose and GlcNAc, and glycopeptides and glycoproteins having them. The sugar chain to be transferred is an asparagine-linked sugar chain, and may be a chemically synthesized sugar chain or cleaved sugar chain.

Figure 15:
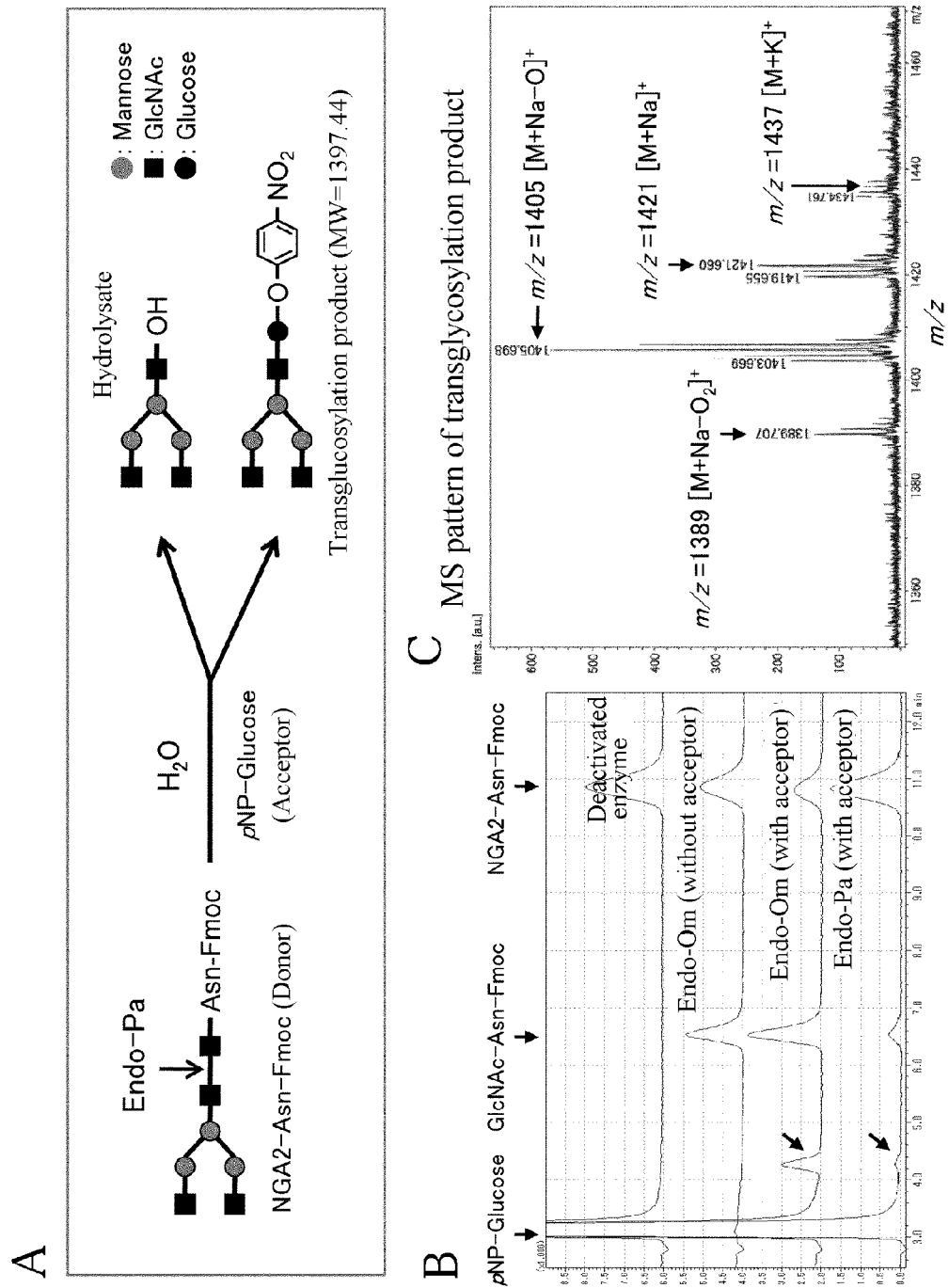
FIG. 15 shows the results of detection of the presence or absence of transglycosidase activity of Endo-Pa. A: transglycosylation of Endo-Pa; B: detection of sugar transfer activity by HPLC; and C: MS patterns of the transglycosylation product.

The transglycosidase activity of Endo-Pa was detected by incubating the reaction solution containing a biantennary complex type sugar chain as the substrate, acceptor molecules (p-nitrophenylglucose), and an Endo-Pa partially purified enzyme solution at 30° C. for 16 hours, and then subjecting it to HPLC after the completion of the reaction; a new peak different from the hydrolysate was detected, and was identified by MS analysis to be a transglycosylation product including an acceptor molecule to which a biantennary complex type sugar chain is added (FIG. 15).

1-4. About "Endo-Zr"

(1) Enzymological and Physicochemical Properties;
(1) Action; acts on an asparagine-linked glycoprotein in an endo type, and liberates a sugar chain.

(2) Substrate specificity;
1) cleaves the N,N'-diacetylchitobiose moiety, which is contained in the core structure of the high-mannose type, hybrid type, and biantennary complex type sugar chains, to form an oligosaccharide;
2) when the activity for the high-mannose type M8A-PA sugar chain is set at 100%, the activity for the high-mannose type M6B-PA sugar chain is about 127%, and the activity for a biantennary complex type sugar chain (agalacto bianten-nary PA-sugar) is about 23.6%.
(3) Optimal pH; about 4.5 to 5.0
(4) Optimal temperature; 40° C.
(5) Gene; 1920 bp (homology of 29.4% with the amino acid sequence of Endo-M)
(6) Molecular weight; 73,105 Da (from the amino acid sequence)
(7) Transglycosidase activity; not detected.

(2) Amino Acid Sequence and Nucleotide Sequence

The endo-β-N-acetylglucosaminidase of the present invention (Endo-Zr) can be expressed as a protein containing any of the following amino acid sequences (1) to (5) and having endo-β-N-acetylglucosaminidase activity; the protein is preferably derived from a yeast, more preferably a *Zygosaccharomyces* yeast, and most preferably derived from *Zygosaccharomyces rouxii*:
(1) the amino acid sequence set forth in SEQ ID NO. 13,
(2) the amino acid sequence obtained by deletion, substitution, insertion and/or addition of one or several amino acids in the amino acid sequence set forth in SEQ ID No. 13 ("several amino acids" means 1 to 20, preferably 1 to 10, and more preferably 1 to 5 amino acids);

(3) the amino acid sequence having an identity of at least 70% with the amino acid sequence set forth in SEQ ID No. 13 (the amino acid sequence preferably has an identity of 80% or more, more preferably 85% or more, and even more preferably 90% or more);

(4) the amino acid sequence coded by the nucleotide sequence set forth in SEQ ID NO. 14; and (5) the amino acid sequence coded by the nucleotide sequence of the polynucleotide which hybridizes with the polynucleotide including the complementary sequence of the nucleotide sequence set forth in SEQ ID NO. 14 under stringent conditions (wherein the "stringent conditions" are as described above).

Furthermore, the protein having Endo-Zr activity of the present invention is including the yeast-derived amino acid sequence detected by the BLAST search through the NCBI GenBank amino acid sequence database at a homology of 30% or more, preferably 40% or more, more preferably 50% or more, even more preferably 70% or more, and most preferably 80% or more with the amino acid sequence set forth in SEQ ID NO. 13, and has endo-β-N-acetylglucosaminidase activity. In particular, the gene is preferably derived from a *Zygosaccharomyces* yeast.

Alternatively, it can be expressed as a protein which is coded by the gene including the yeast-derived nucleotide sequence detected by the BLAST search through the NCBI GenBank nucleotide sequence database at a homology of 30% or more, preferably 40% or more, more preferably 50% or more, even more preferably 70% or more, and most preferably 80% or more with the nucleotide sequence set forth in SEQ ID NO. 14, and has endo-β-N-acetylglucosaminidase activity.

In addition, the Endo-Zr gene of the present invention can be expressed as a polynucleotide which codes the protein having endo-β-N-acetylglucosaminidase activity containing any of the above-described amino acid sequences (1) to (5), and also can be expressed as any of the following polynucleotides (1) to (3), wherein the polynucleotide is preferably derived from a yeast, particularly preferably derived from a *Zygosaccharomyces* yeast:

(1) the polynucleotide containing the nucleotide sequence set forth in SEQ ID NO. 14;

(2) the polynucleotide which hybridizes with the polynucleotide including the complementary sequence of the nucleotide sequence set forth in SEQ ID NO. 14 under stringent conditions, and codes a protein having endo-β-N-acetylglucosaminidase activity;

(3) the polynucleotide which is amplified by the primer set containing the nucleotide sequences set forth in SEQ ID NO. 15 and 16, has an identity of 70% or more with SEQ ID NO. 14, and codes a protein having endo-β-N-acetylglucosaminidase activity (the nucleotide sequence preferably has an identity of 80% or more, more preferably 85% or more, and even more preferably 90% or more);

As shown in FIG. 2, the endo-β-N-acetylglucosaminidase (Endo-Zr) of the present invention has an identity of 30.6% at the amino acid sequence level with the "Endo-Om" of the present invention derived from *Ogataea minuta*, and has identities of 31.9% and 30.2% with the "Endo-Cp" enzyme derived from *Candida parapolymorpha* DL-1 and the "Endo-Pa" enzyme derived from *Pichia anomala*, which were found at the same time, respectively. The identity with the well-known "Endo-M" derived from the genus *Mucor* is only 29.4% at the amino acid sequence level. In this manner, the "Endo-Zr" of the present invention has a specific sequence. Therefore, when the polypeptide is including an amino acid sequence having an identity of 70% or more, preferably 80% or more, and even more preferably 90% or more with the amino acid sequence set forth in SEQ ID No. 13, it has an extremely high probability of having Endo-Zr activity, and the polynucleotide including the nucleotide sequence having an identity of 70% or more, preferably 80% or more, and more preferably 90% or more with the nucleotide sequence set forth in SEQ ID NO. 14 also has a high probability of being an Endo-Zr gene. The homology search of polypeptides and polynucleotides can be carried out by, for example, using the FASTA or BLAST program for DNA Databank of JAPAN (DDBJ).

(3) Hydrolysis activity for various sugar chains

Using the Endo-Zr partially purified enzyme solution of the present invention, hydrolysis activity for various PA-labeled commercially available sugar chains (TaKaRa-Bio Inc.) were measured, and the results are shown in the following (Table 4) together with the measurements in a literature on Endo-M (Non Patent Literature 6). The hydrolysis activity at that time was calculated from the peak area ratio between the PA-labeled sugar chain and its hydrolysate as substrates in HPLC, and the relative activity for the various sugar chains was calculated, with the hydrolysis activity for the sugar chain with an M8A structure set at 100%.

TABLE 4

| Substrate | Endo-Zr | Endo-M* |
|---|---|---|
| 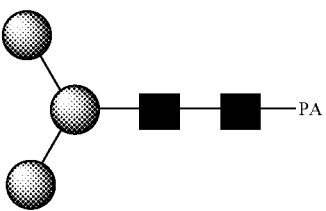 M3B | 85.7% | 19.5% |

TABLE 4-continued
| Substrate | Endo-Zr | Endo-M* |
|---|---|---|
| 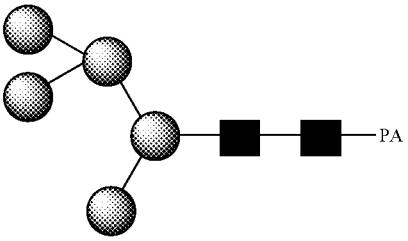 M5A | 39.8% | 15.4% |
| 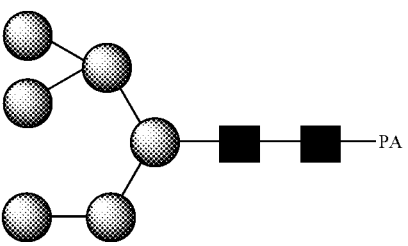 M6B | 127% | 74.0% |
| 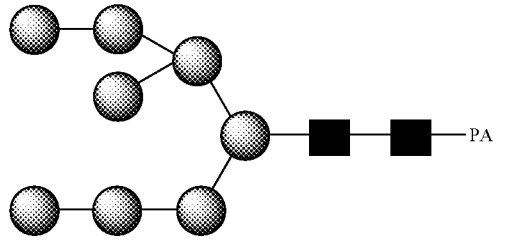 M8A | 100% | 100% |
| 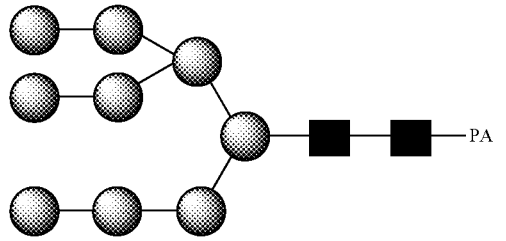 M9A | 33.4% | 66.5% |
| 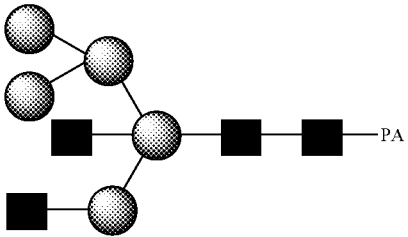 hybrid-type (bisecting GlcNAc) | ND | — |

TABLE 4-continued

| Substrate | Endo-Zr | Endo-M* |
|---|---|---|
| hibrid-type | 13.2% | — |
| sialobiantennary | 17.3% | 7.0% |
| biantennary | 30.0% | 13.3% |
| fucosyl biantennary | ND | ND |
| agalacto biantennary | 23.6% | 4.4% |
| agalacto triantennary | ND | ND |

TABLE 4-continued

| Substrate | Endo-Zr | Endo-M* |
|---|---|---|
| 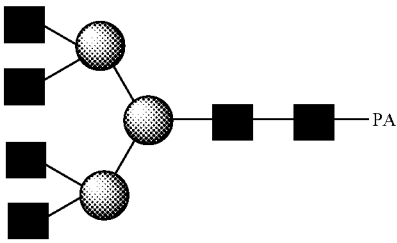<br>agalacto tetraantennary | ND | ND |

The relative activity was calculated using M8A as the substrate.
*Relative activity of Endo-M was cited from Fujita et al. (2004) Arch Biochem Biophy, 432: p. 41-49

●: Mannose,
■: GlcNAc,
○: Galactose,
▲: Fucose,
♦: Neu5Ac,
ND: Not detected.

The above-described results (Table 4) indicate that Endo-Zr has as high hydrolysis activity as Endo-M for a high-mannose sugar chain, and further hydrolyzes a hybrid type sugar chain and a biantennary complex type sugar chain. On the other hand, it cannot hydrolyze a triantennary or more highly branched complex type sugar chain, a sugar chain having a core fucose structure, and a hybrid type sugar chain having bisecting GlcNAc. In addition, it shows different reactivity for several sugar chains from Endo-M, and exhibits particularly higher reactivity for a biantennary complex type sugar chain and sugar chains having an M3B, MSA, or M6B structure than Endo-M.

2. Method for Obtaining and Producing the Endo-β-N-Acetylglucosaminidase of the Present Invention 2-1. Method for Obtaining and Producing Endo-Om (1) Strain Producing the Endo-β-N-Acetylglucosaminidase (Endo-Om) of the Present Invention The microorganism producing the Endo-Om of the present invention is the methylotrophic yeast *Ogataea minuta* IFO10746 strain described in Patent Literature 6 previously applied by the inventors, and is a yeast strain which can be grown using methanol as the only one carbon source. Details about the culture method are as described in Patent Literature 6. Methanol is added to a medium for ordinary yeasts, and ordinary yeast culture conditions are used. The cultured cells are collected and crushed, and the supernatant free from impurity can be used as a crude enzyme solution. However, the amount of production was small, so that the Endo-Om gene was cloned, and transformed using the original yeast strain as the host, and an Endo-Om gene-overexpression system was prepared as described in the following (3).

(2) Method for Obtaining Endo-Om and its Gene from Other Microorganism

The host-vector system using the *Ogataea minuta* IFO10746 strain is described in JP 4464269 B1 (Patent Literature 7). The genome sequence information was searched for the gene having high homology with Endo-M, and a gene partially having high homology was found. Then, the genome DNA of *O. minuta* was extracted by a common procedure, and the ORF full length sequence of the Endo-Om gene was amplified by the PCR method using the primer 1 (SEQ ID NO. 3) and primer 2 (SEQ ID NO. 4).

```
Primer 1:
                                          (SEQ ID NO. 3)
5'-CGATGACAAGGGATCATGGCGCAATCTCAGCTACTGG-3'

Primer 2:
                                          (SEQ ID NO. 4)
5'-GCACCGTCTCGGATCTCACACCCAAACCTCACTCC-3'
```

The PCR fragment thus obtained was subcloned by TOPO Blunt cloning kit (Invitrogen), and thus the nucleotide sequence was determined.

Figure 1:
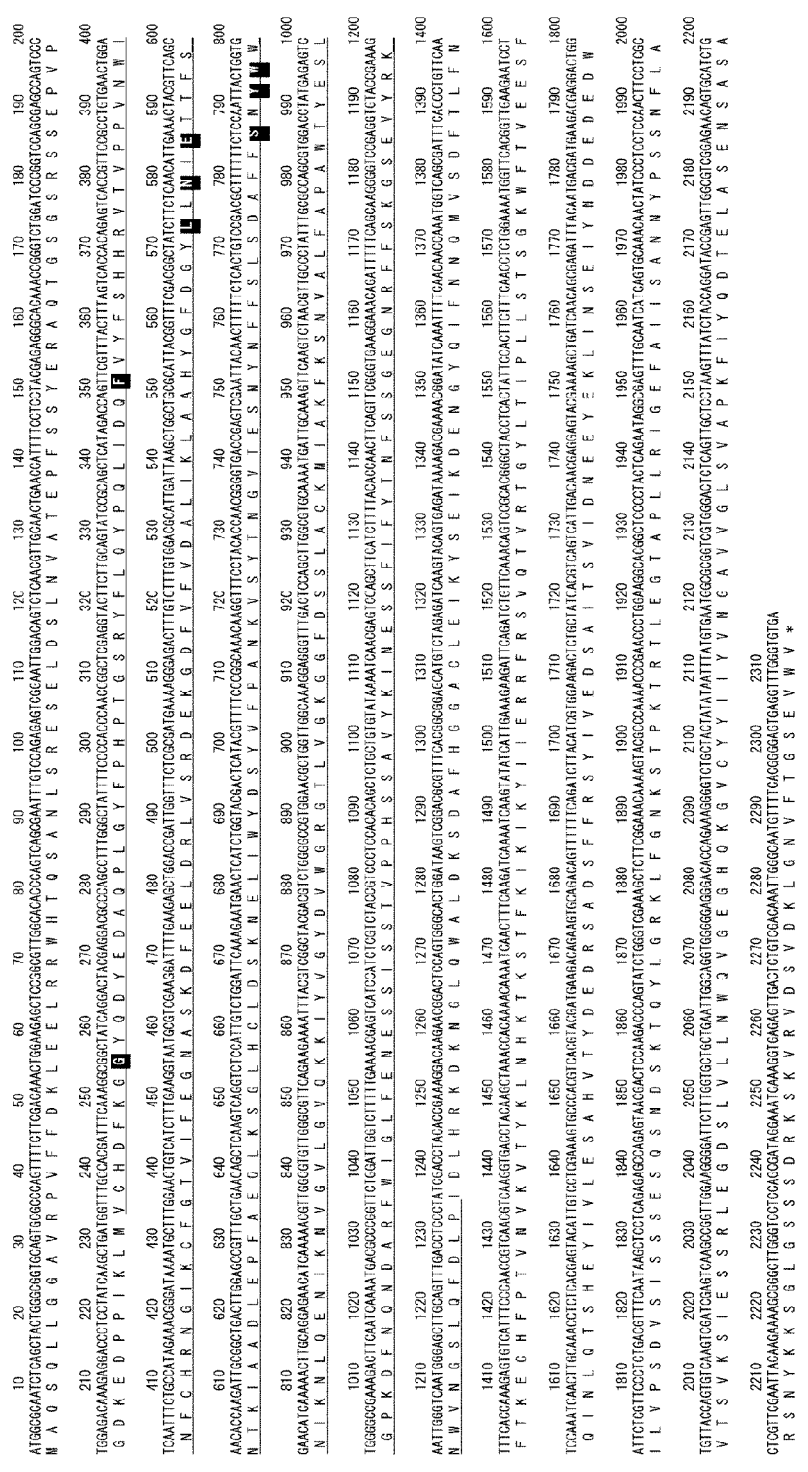

The nucleotide sequence and amino acid sequence of the Endo-Om gene obtained by the cloning are shown in FIG. 1. The ORF of Endo-Om is including 2319 bases, and coded the protein including 772 amino acids and having a molecular weight of 87,398.

The present method may be used for a closely-related organism of *Ogataea minuta* from which the Endo-Om gene of the present invention is obtained, for example, a *Pichia* yeast which is other methylotrophic yeast, or a DNA library derived from a microorganism such as a bacterium, thereby obtaining an enzyme gene having Endo-Om activity.

More specifically, the Endo-Om gene thus obtained can be described as the gene which hybridizes with the DNA including the nucleotide sequence set forth in SEQ ID NO. 2 and the DNA including its complementary nucleotide sequence under stringent conditions, and codes a protein having Endo-Om activity.

The Endo-Om gene of the present invention can be obtained by searching a well-known database, and the Endo-Om gene thus obtained has a nucleotide sequence with a homology (identity) of 70% or more, preferably 85% or more, more preferably 90% or more, and most preferably 95% or more for the nucleotide sequence set forth in SEQ ID NO. 2, and the corresponding protein having Endo-Om activity can be expressed as having an amino acid sequence with a homology (identity) of 70% or more, preferably 80% or more, more preferably 90% or more, and most preferably 95% or more for the amino acid sequence set forth in SEQ ID NO. 1. The homology search of polypeptides and polynucleotides can be carried out by, for example, using the FASTA or BLAST program for DNA Databank of JAPAN (DDBJ).

(3) Method for Constructing Overexpression System and Producing Endo-Om in High Volume The Endo-Om-overexpressing strain of a methylotrophic yeast *O. minuta* was prepared as follows.

Firstly, the ORF full length sequence (2349 bp) of the Endo-Om gene was amplified by the PCR method, purified, and then incorporated into the plasmid pOMEA1 for expression using In-Fusion™ Advantage PCR Cloning Kit (Clontech), and thus pOMEA1-Endo-Om was constructed.

The pOMEA1-Endo-Om thus constructed was transformed into the competent cells of the *O. minuta* TK10-1-2 strain using the electroporation method, and thus an Endo-Om-overexpressing *O. minuta* strain (Endo-Om/TK10-1-2 strain) was obtained.

The Endo-Om/TK10-1-2 strain was induced to express Endo-Om, an extracting buffer and glass beads were added to the collected yeast cells, and shaken vigorously to crush the cells. The insoluble matter was removed from the supernatant by centrifugation, and the supernatant was used as an Endo-Om crude enzyme solution.

The Endo-Om crude enzyme solution was denatured by an SDS sample buffer, Western blotting was carried out by a common procedure, thereby confirming the protein expression.

In order to obtain the above-described Endo-Om-overexpressing strain, the host is preferably the same methylotrophic yeast from which the Endo-Om gene of the present invention is obtained, or its analogue yeast. Alternatively, a bacterium such as *E. coli*, bacteria, insect cells, plant cells, or animal cells may be used to construct a similar overexpressing strain by using a vector into which a high expressing promoter is incorporated. In addition, production using a transgenic animal is possible.

Using a transformant strain such as a transformed *Ogataea minuta* Endo-Om-overexpressing strain, high-volume production is allowed under ordinary transformant culture conditions, or using a culture method by methanol induction.

2-2. Method for Obtaining and Producing Endo-Cp (1) Strain Producing the Endo-β-N-Acetylglucosaminidase (Endo-Cp) of the Present Invention The microorganism producing the Endo-Om of the present invention is a methylotrophic yeast *Candida* parapolymorpha DL-1 ATCC26012 strain, and is a yeast strain which can be grown using methanol as the only one carbon source. The yeast is cultured under ordinary yeast culture conditions using a medium for ordinary yeasts containing methanol. The cultured yeast cells are collected and crushed, and the supernatant free from impurity can be used as a crude enzyme solution. However, the amount of production was small, so that the Endo-Cp gene was cloned, and transformed using *E. coli* as the host, and an Endo-Cp gene-overexpression system was prepared as described in the following (3).

(2) Method for Obtaining Endo-Cp and its Gene from Other Microorganism

The genome DNA of the *Candida parapolymorpha* DL-1 ATCC26012 strain was extracted by a common procedure, and the ORF full-length sequence of the Endo-Cp gene was amplified by the PCR method using the primer 3 (SEQ ID NO. 7) and the primer 4 (SEQ ID NO. 8).

Primer 3:
(SEQ ID NO. 7)
5'-TCGAAGGTAGGCATATGCCTCGAAACACAGCTAA-3'

Primer 4:
(SEQ ID NO. 8)
5'-GCTTGAATTCGGATCCTCAAATGTGCATATCGGTACCCT-3'

The PCR product thus obtained was incorporated into the protein-expressing plasmid pCold I DNA for *E. coli* (TaKaRa-Bio Inc.) using In-Fusion™ HD Cloning Kit (Clontech), thereby constructing pCold I-Endo-Cp. The DNA sequencing of the purified vector was carried out, and the full-length nucleotide sequence of the Endo-Cp gene was determined.

Figure 8:
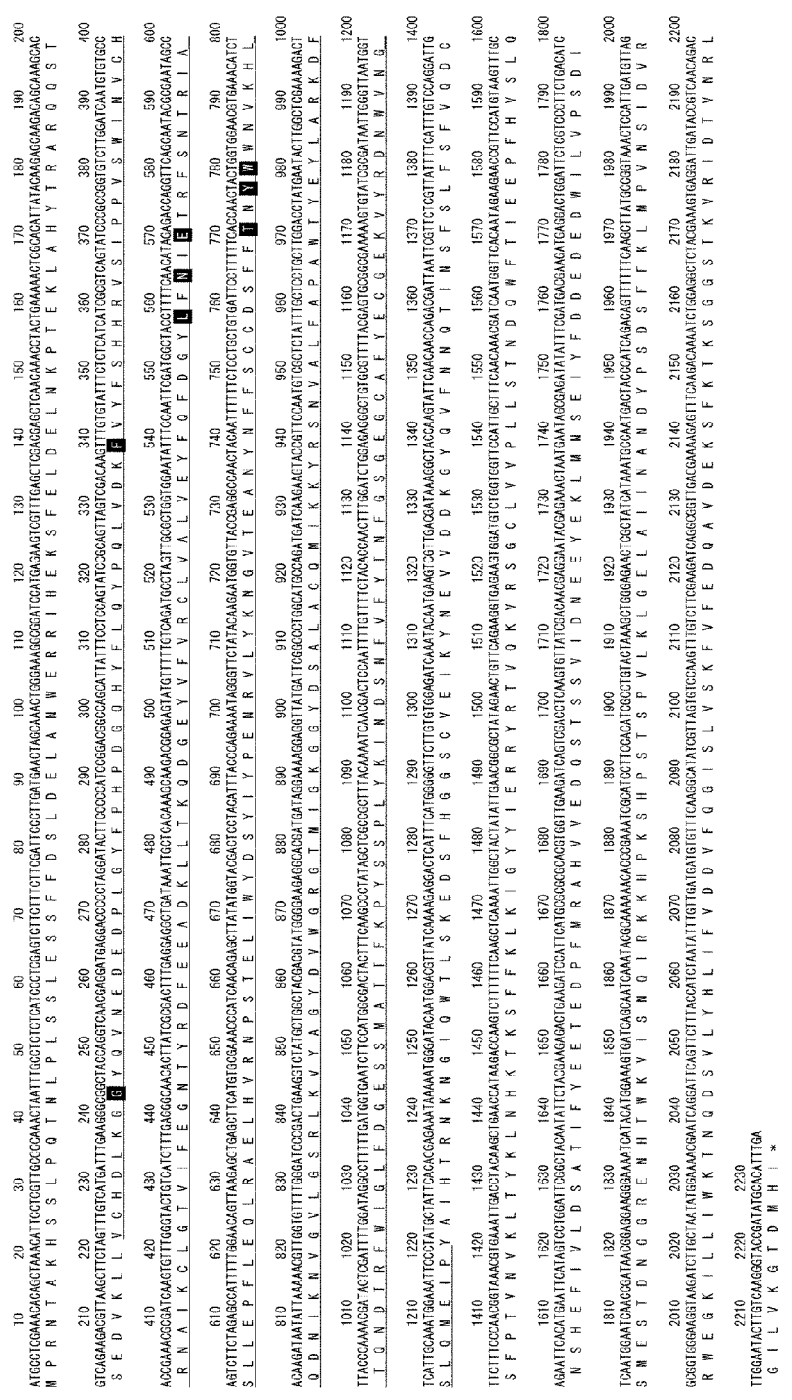

The nucleotide sequence and amino acid sequence of the Endo-Cp gene obtained by the cloning are shown in FIG. 8. The ORF of Endo-Cp is including 2238 bases, and coded the protein including 745 amino acids and having a molecular weight of 86,500.

The present method may be used for a closely-related organism of *Candida parapolymorpha* DL-1 from which the Endo-Cp gene of the present invention is obtained, for example, a *Pichia* yeast which is other methylotrophic yeast, or a DNA library derived from a microorganism such as a bacterium, thereby obtaining an enzyme gene having Endo-Cp activity.

More specifically, the Endo-Cp gene thus obtained can be described as the gene which hybridizes with the DNA including the nucleotide sequence set forth in SEQ ID NO. 6 and the DNA including its complementary nucleotide sequence under stringent conditions, and codes a protein having Endo-Cp activity.

The Endo-Cp gene of the present invention can be obtained by searching a well-known database, and the Endo-Cp gene thus obtained has a nucleotide sequence with a homology (identity) of 70% or more, preferably 85% or more, more preferably 90% or more, and most preferably 95% or more for the nucleotide sequence set forth in SEQ ID NO. 6, and the corresponding protein having Endo-Cp activity can be expressed as having an amino acid sequence with a homology (identity) of 70% or more, preferably 80% or more, more preferably 90% or more, and most preferably 95% or more for the amino acid sequence set forth in SEQ ID NO. 5. The homology search of polypeptides and polynucleotides can be carried out by, for example, using the FASTA or BLAST program for DNA Databank of JAPAN (DDBJ).

(3) Method for Constructing Overexpression System and Producing Endo-Cp in High Volume The Endo-Cp-overexpressing strain of a *E. coli* was prepared as follows.

The pCold I-Endo-Cp described in (2) was transformed into the *E. coli* competent cells for protein expression (NEB Express Competent *E. coli* (High Efficiency), NEW ENGRAND BioLabs), thereby obtaining an Endo-Cp-expressing *E. coli* strain.

The Endo-Cp-expressing *E. coli* strain was induced to express Endo-Cp, an extracting buffer and glass beads were added to the collected bacterial cells, and shaken vigorously to crush the cells. The insoluble matter was removed from the supernatant by centrifugation, and the supernatant was used as an Endo-Cp crude enzyme solution.

The Endo-Cp crude enzyme solution was denatured by an SDS sample buffer, Western blotting was carried out by a common procedure, thereby confirming the protein expression.

In order to obtain the above-described Endo-Cp-overexpressing strain, the host is preferably the same *Candida* yeast from which the Endo-Cp gene of the present invention is obtained, or its analogue yeast.

Alternatively, a bacterium such as *E. coli*, bacteria, insect cells, plant cells, or animal cells may be used to construct a similar overexpressing strain by using a vector into which a high expressing promoter is incorporated. In addition, production using a transgenic animal is possible.

Using a transformant strain such as an Endo-Cp-overexpressing *E. coli* strain, high-volume production is allowed under ordinary transformant culture conditions.

2-3. Method for Obtaining and Producing Endo-Pa (1) Strain Producing the Endo-β-N-Acetylglucosaminidase (Endo-Pa) of the Present Invention The microorganism producing the Endo-Ps of the present invention is a *Pichia anomala* ATCC36904. The yeast is cultured under ordinary yeast culture conditions using a medium for ordinary yeasts. The cultured yeast cells are collected and crushed, and the supernatant free from impurity can be used as a crude enzyme solution. However, the amount of production was small, so that the Endo-Pa gene was cloned, and transformed using *E. coli* as the host, and an Endo-Pa gene-overexpression system was prepared as described in the following (3).

(2) Method for Obtaining Endo-Pa and its Gene from Other Microorganism

The genome DNA of the *Pichia anomala* ATCC36904 strain was extracted by a common procedure, and the ORF full-length sequence of the Endo-Pa gene was amplified by the PCR method using the primer 5 (SEQ ID NO. 11) and the primer 6 (SEQ ID NO. 12).

```
Primer 5:
                                        (SEQ ID NO. 11)
5'-TCGAAGGTAGGCATATGCAACATGATCATGCTGCCATA-3'

Primer 6:
                                        (SEQ ID NO. 12)
5'-GCTTGAATTCGGATCCCTATATAAATATATCCTCGCCTTTG-3'
```

The PCR product thus obtained was incorporated into the protein-expressing plasmid pCold I DNA for *E. coli* (TaKaRa-Bio Inc.) using In-Fusion™ HD Cloning Kit (Clontech), thereby constructing pCold I-Endo-Pa. The DNA sequencing of the purified vector was carried out, and the full-length nucleotide sequence of the Endo-Pa gene was determined.

Figure 12:
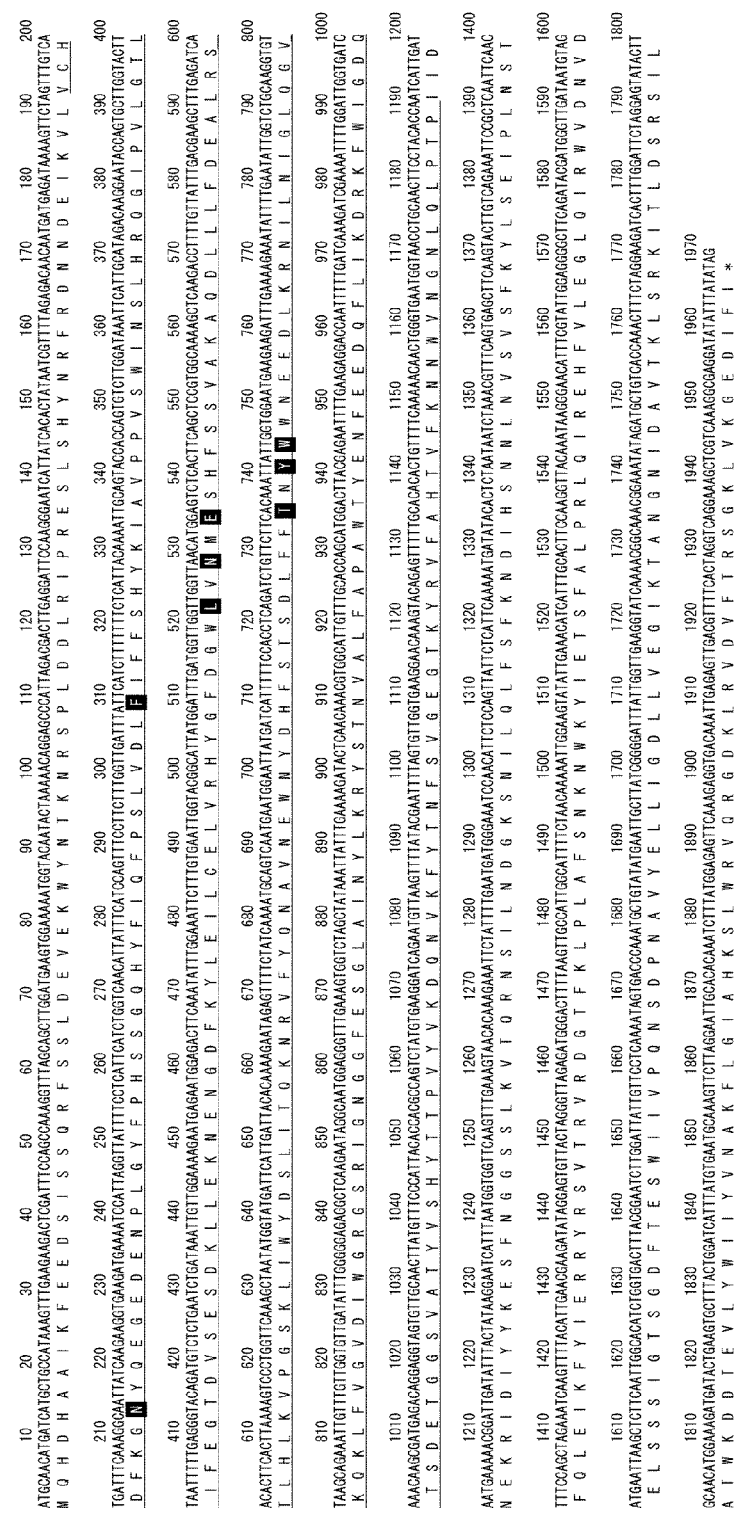

The nucleotide sequence and amino acid sequence of the Endo-Pa gene obtained by the cloning are shown in FIG. 12. The ORF of Endo-Pa is including 1971 bases, and coded the protein including 656 amino acids and having a molecular weight of 76,050.

The present method may be used for a closely-related organism of *Pichia anomala* from which the Endo-Pa gene of the present invention is obtained, for example, a *Pichia* yeast which is other methylotrophic yeast, or a DNA library derived from a microorganism such as a bacterium, thereby obtaining an enzyme gene having Endo-Pa activity.

More specifically, the Endo-Pa gene thus obtained can be described as the gene which hybridizes with the DNA including the nucleotide sequence set forth in SEQ ID NO. 10 and the DNA including its complementary nucleotide sequence under stringent conditions, and codes a protein having Endo-Pa activity.

The Endo-Pa gene of the present invention can be obtained by searching a well-known database, and the Endo-Pa gene thus obtained has a nucleotide sequence with a homology (identity) of 70% or more, preferably 85% or more, more preferably 90% or more, and most preferably 95% or more for the nucleotide sequence set forth in SEQ ID NO. 10, and the corresponding protein having Endo-Pa activity can be expressed as having an amino acid sequence with a homology (identity) of 70% or more, preferably 80% or more, more preferably 90% or more, and most preferably 95% or more for the amino acid sequence set forth in SEQ ID NO. 9. The homology search of polypeptides and polynucleotides can be carried out by, for example, using the FASTA or BLAST program for DNA Databank of JAPAN (DDBJ).

(3) Method for Constructing Overexpression System and Producing Endo-Pa in High Volume The Endo-Pa-overexpressing strain of a *E. coli* was prepared as follows.

The pCold I-Endo-Pa described in (2) was transformed into the *E. coli* competent cells for protein expression (NEB Express Competent *E. coli* (High Efficiency), NEW ENGRAND BioLabs), thereby obtaining an Endo-Pa-expressing *E. coli* strain.

The Endo-Pa-expressing *E. coli* strain was induced to express Endo-Pa, an extracting buffer and glass beads were added to the collected bacterial cells, and shaken vigorously to crush the cells. The insoluble matter was removed from the supernatant by centrifugation, and the supernatant was used as an Endo-Pa crude enzyme solution.

The Endo-Pa crude enzyme solution was denatured by an SDS sample buffer, Western blotting was carried out by a common procedure, thereby confirming the protein expression.

In order to obtain the above-described Endo-Pa-overexpressing strain, the host is preferably the same *Pichia* yeast from which the Endo-Pa gene of the present invention is obtained, or its analogue yeast. Alternatively, bacteria such as *E. coli*, insect cells, plant cells, or animal cells may be used to construct a similar overexpressing strain by using a vector into which a high expressing promoter is incorporated. In addition, production using a transgenic animal is possible.

Using a transformant strain such as an Endo-Pa-overexpressing *E. coli* strain, high-volume production is allowed under ordinary transformant culture conditions.

2-4. Method for Obtaining and Producing Endo-Zr (1) Strain Producing the Endo-β-N-Acetylglucosaminidase (Endo-Zr) of the Present Invention The microorganism producing the Endo-Zr of the present invention is a *Zygosaccharomyces rouxii* ATCC2623. The yeast is cultured under ordinary yeast culture conditions using a medium for ordinary yeasts. The cultured bacterial cells are collected and crushed, and the supernatant free from impurity can be used as a crude enzyme solution. However, the amount of production was small, so that the Endo-Zr gene was cloned, and transformed using *E. coli* as the host, and an Endo-Zr gene-overexpression system was prepared as described in the following (3).

(2) Method for Obtaining Endo-Pa and its Gene from Other Microorganism

The genome DNA of the *Zygosaccharomyces rouxii* ATCC2623 strain was extracted by a common procedure, and the ORF full-length sequence of the Endo-Zr gene was amplified by the PCR method using the primer 7 (SEQ ID NO. 15) and the primer 8 (SEQ ID NO. 16).

Primer 7:
(SEQ ID NO. 15)
5'-TCGAAGGTAGGCATATGAAACGTATTAATCAGGT-3'

Primer 8:
(SEQ ID NO. 16)
5'-GCTTGAATTCGGATCCTTACTTCTTGACTACGAATTTCAAAG-3'

The PCR product thus obtained was incorporated into the protein-expressing plasmid pCold I DNA for *E. coli* (TaKaRa-Bio Inc.) using In-Fusion™ HD Cloning Kit (Clontech), thereby constructing pCold I-Endo-Zr. The DNA sequencing of the purified vector was carried out, and the full length nucleotide sequence of the Endo-Zr gene was determined.

Figure 16:
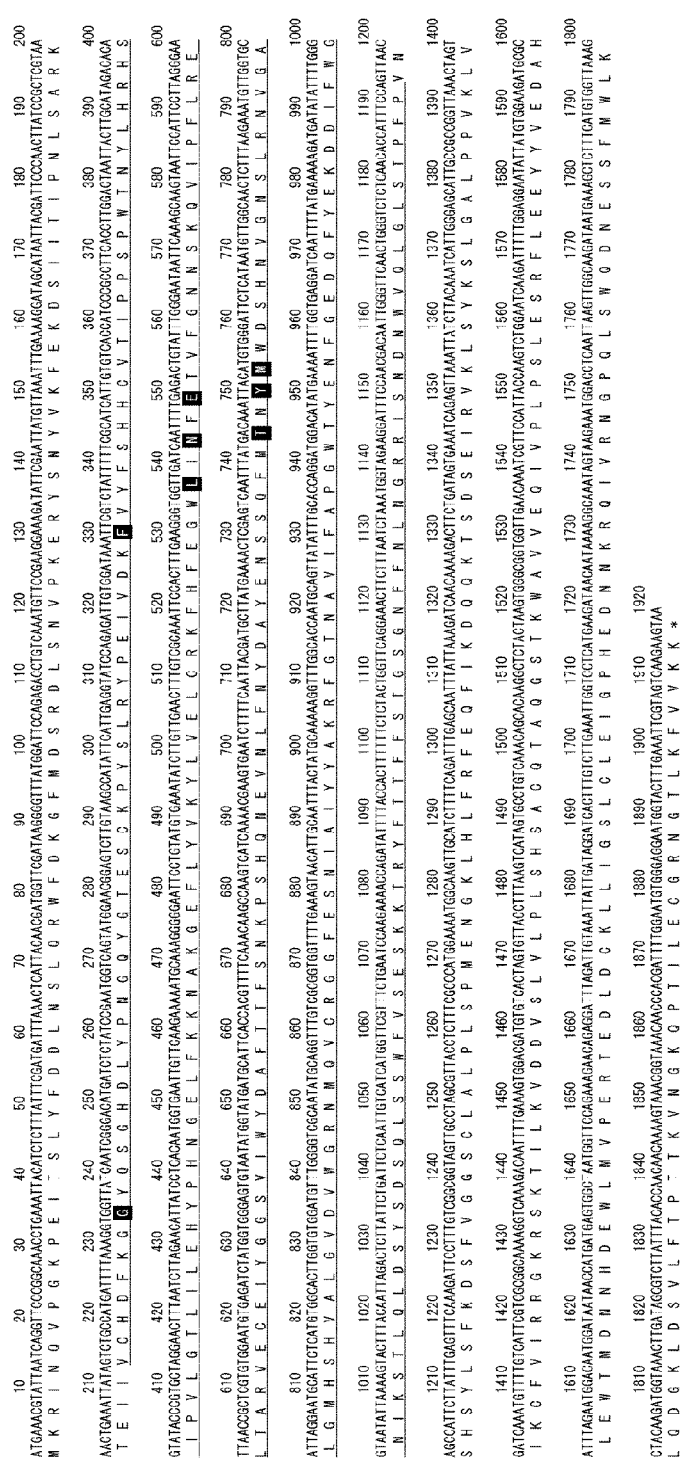

The nucleotide sequence and amino acid sequence of the Endo-Zr gene obtained by the cloning are shown in FIG. 16. The ORF of Endo-Pa is including 1920 bases, and coded the protein including 639 amino acids and having a molecular weight of 73,105.

The present method may be used for a closely-related organism of *Zygosaccharomyces rouxii* from which the Endo-Zr gene of the present invention is obtained, for example, a *Pichia* yeast which is other methyl-utilizing yeast, or a DNA library derived from a microorganism such as a bacterium, thereby obtaining an enzyme gene having Endo-Zr activity.

More specifically, the Endo-Zr gene thus obtained can be described as the gene which hybridizes with the DNA including the nucleotide sequence set forth in SEQ ID NO. 14 and the DNA including its complementary nucleotide sequence under stringent conditions, and codes a protein having Endo-Zr activity.

The Endo-Zr gene of the present invention can be obtained by searching a well-known database, and the Endo-Zr gene thus obtained has a nucleotide sequence with a homology (identity) of 70% or more, preferably 85% or more, more preferably 90% or more, and most preferably 95% or more for the nucleotide sequence set forth in SEQ ID NO. 14, and the corresponding protein having Endo-Zr activity can be expressed as having an amino acid sequence with a homology (identity) of 70% or more, preferably 80% or more, more preferably 90% or more, and most preferably 95% or more for the amino acid sequence set forth in SEQ ID NO. 13. The homology search of polypeptides and polynucleotides can be carried out by, for example, using the FASTA or BLAST program for DNA Databank of JAPAN (DDBJ).

(3) Method for Constructing Overexpression System and Producing Endo-Zr in High Volume The Endo-Zr-overexpressing strain of *E. coli* was prepared as follows.

The pCold I-Endo-Zr described in (2) was transformed into the *E. coli* competent cells for protein expression (NEB Express Competent *E. coli* (High Efficiency), NEW ENGRAND BioLabs), thereby obtaining an Endo-Zr-expressing *E. coli* strain.

The Endo-Zr-expressing *E. coli* strain was induced to express Endo-Zr, an extracting buffer and glass beads were added to the collected bacterial cells, and shaken vigorously to crush the cells. The insoluble matter was removed from the supernatant by centrifugation, and the supernatant was used as an Endo-Zr crude enzyme solution.

The Endo-Zr crude enzyme solution was denatured by an SDS sample buffer, Western blotting was carried out by a common procedure, thereby confirming the protein expression.

In order to obtain the above-described Endo-Zr-overexpressing strain, the host is preferably the same *Zygosaccharomyces* yeast belonging to the genus from which the Endo-Zr gene of the present invention is obtained, or its analogue yeast. Alternatively, bacteria such as *E. coli*, insect cells, plant cells, or animal cells may be used to construct a similar overexpressing strain by using a vector into which a high expressing promoter is incorporated. In addition, production using a transgenic animal is possible.

Using a transformant strain such as an Endo-Zr-overexpressing *E. coli* strain, high-volume production is allowed under ordinary transformant culture conditions.

3. Use of the Endo-β-N-Acetylglucosaminidase of the Present Invention

The endo-β-N-acetylglucosaminidase (Endo-Om) of the present invention has activity for cleaving a complex type sugar chain with a high specific activity, and also has activity for transferring a cleaved sugar chain and a chemically synthesized sugar chain to any acceptor molecule, for example, a monosaccharide such as glucose or N-acetylglucosamine or its derivative, or a glycopeptide or glycoprotein having the saccharide.

Accordingly, the use of the Endo-Om of the present invention allows the analysis of the sugar chain structure including the complex type sugar chain in a glycoprotein. In addition, it can be used for various types of glycosylation, such as the preparation of a neoglycoprotein including the addition of a sugar chain to a protein to which a sugar chain will not be naturally attached, or the introduction of an N-type sugar chain to the position to which the sugar chain will not be attached, cleavage of a heterogeneous sugar chain, followed by homogenization of the N-type sugar chain of a glycoprotein using transglycosidase reaction, and preparation of a standard glycoprotein for a sugar chain analyzer.

Endo-Cp, Endo-Pa, and Endo-Zr, which are other endo-β-N-acetylglucosaminidases of the present invention, also have similar complex type sugar chain cleavage activity and complex type sugar chain transfer activity for any acceptor molecules, so that they are expected to have similar uses.

The present invention is further described below with reference to examples. The technical scope of the present invention will not be limited by these explanations. In addition, the contents of the technical literatures cited herein are regarded as parts of the disclosure of the present description.

EXAMPLES

Example 1

Discovery of *O. minuta*-Derived ENGase (Endo-Om)

As described in the preceding application by the present inventors (Patent Literature 6), secretion production of human glycotransferase using *O. minuta* was carried out. The secreted MGAT5 was partially purified, and reaction was carried out using a biantennary complex type sugar chain (NGA2-Asn-Fmoc) as the receptor substrate, and UDP-GlcNAc as the donor substrate. As the result of the analysis of the products, the peak of by-product other than the transglycosylation product was confirmed. The receptor substrate NGA2-Asn-Fmoc was successively digested by exo-glycosidase to prepare a standard sample, and the peak was analyzed; it was suggested that the bond between GlcNAcβ1-4GlcNAc is cleaved existing on the reducing end of the receptor substrate. It is known that Endo-M has activity for efficiently cleaving a biantennary complex type sugar chain, so that *O. minuta* was considered to have same activity. Therefore, cloning of the gene was studied.

Example 2

Cloning of *O. minuta*-Derived ENGase (Endo-Om) Gene

The host-vector system using the *Ogataea* minuta IFO10746 strain is described in JP 4464269 B1 (Patent Literature 7). The genome sequence information was searched for the gene having high homology with Endo-M, and a gene partially having high homology was found. Then, the genome DNA of *O. minuta* was extracted by a common procedure, and the ORF full length sequence of the Endo-Om gene was amplified by the PCR method using the primer 1 (SEQ ID NO. 3) and the primer 2 (SEQ ID NO. 4).

```
Primer 1:
                                        (SEQ ID NO. 3)
5'-CGATGACAAGGGATCATGGCGCAATCTCAGCTACTGG-3'

Primer 2:
                                        (SEQ ID NO. 4)
5'-GCACCGTCTCGGATCTCACACCCAAACCTCACTCC-3'
```

The PCR fragment thus obtained was subcloned using TOPO Blunt cloning kit (Invitrogen), and the nucleotide sequence was determined.

The nucleotide sequence and amino acid sequence of the Endo-Om gene obtained by the cloning are shown in FIG. 1. The ORF of Endo-Om is including 2319 bases, and coded the protein including 772 amino acids and having a molecular weight of 87,398. The estimated isoelectric point was 5.59. Based on the amino acid sequence thus obtained, BLAST search was carried on the NCBI amino acid sequence database; Endo-Om had the sequence highly conserved in GH family 85 ENGase belonging to the GH18 Chitinase-like superfamily at the position of about 80 to 410 amino acids on the N-terminal side. Of the upper sequences hit by BLAST search, the species close to yeasts were expressed in a dendrogram and shown in FIG. 2. For the sequences other than Endo-M, annotation was not described as ENGase in the database. Endo-Om had the highest homology (53.9%) with the estimated ENGase (the following Example 6, Endo-Cp) derived from the methylotrophic yeast *Candida parapolymorpha* DL-1 (*Hansenula polymorpha* DL-1). The homology with *Mucor hiemalis*-derived Endo-M was 33.9%, and had no homology with the sequences other than those conserved on the N-terminus. On the other hand, no corresponding gene was detected in *Pichia pastoris* or *Candida boidinii*, which are methylotrophic yeasts. In addition, no corresponding gene was detected in *Saccharomyces cerevisiae*.

Example 3

Preparation of Endo-Om-Overexpressing *O. minuta* Strain

The Endo-Om-overexpressing strain of the methanol-utilizing yeast *O. minuta* was prepared as follows.

Firstly, in the same manner as in Example 2, the ORF full length sequence of the Endo-Om gene was amplified by the PCR method using the above-described primer 1 (SEQ ID NO. 3) and primer 2 (SEQ ID NO. 4).

The amplified PCR product of 2349 bp was purified, and then the PCR product was incorporated into the plasmid pOMEA1 for expression, which had been cleaved by BamHI, using In-Fusion™ Advantage PCR Cloning Kit (Clontech), and thus pOMEA1-Endo-Om was constructed.

The pOMEA1-Endo-Om thus constructed was cleaved by NotI, and introduced into the competent cells of the *O. minuta* TK10-1-2 strain using the electroporation method. The transformed yeast was spread over an SD-Ade agar media (2% D-glucose, 0.67% yeast nitrogen base w/o amino acids (Difco), 0.5% casamino acid, 0.1 mg/ml Uracil, 1.5% agar), and cultured at 30° C. for 2 days, thereby obtaining transformant colonies. The colonies were picked up from the plate, incorporation into the chromosome was confirmed by the simple PCR method including suspension in a PCR reaction solution, and the colonies were used as the Endo-Om-overexpressing *O. minuta* strain (Endo-Om/TK10-1-2 strain).

Example 4

Confirmation of Expression and Enzymatic Activity of Endo-Om in Endo-Om-Overexpressing *O. minuta* Strain The Endo-Om/TK10-1-2 strain was inoculated into a 3 ml of YPD medium (2% peptone, 1% yeast extract, and 2% glucose), cultured at 30° C. for 2 days. The medium supernatant was removed by centrifugation, and the yeast cells was resuspended in 3 ml of a BMMY medium (2% peptone, 1% yeast extract, 1.34% yeast nitrogen base w/o amino acids, 2% casamino acid, 1% MeOH, 0.2 mg/ml adenine ½ sulfate, 0.1 mg/ml uracil, and 100 mM potassium phosphate buffer (pH 6.0)), and cultured at 20° C. for further 2 days, thereby inducing the expression of Endo-Om. An extraction buffer (50 mM sodium phosphate buffer (pH 7.4), 1.25 M NaCl, 1 mM PMSF, 1× Complete (Roche), and 5% glycerol) and glass beads were added to the collected yeast cells, and shaken vigorously to crush the cells. The supernatant from which insoluble matter was removed by centrifugation was used as an Endo-Om crude enzyme solution.

Western blotting was carried out as follows. The Endo-Om crude enzyme solution was denatured by an SDS sample buffer, and subjected to Western blotting by a common procedure. Using a mouse anti-FLAG antibody as the primary antibody, and an anti-mouse IgG antibody horseradish peroxidase conjugate was used as the secondary antibody, and ECL plus system (GE Healthcare) and a chemiluminescence detector (GE Healthcare) were used for detection.

Figure 3:
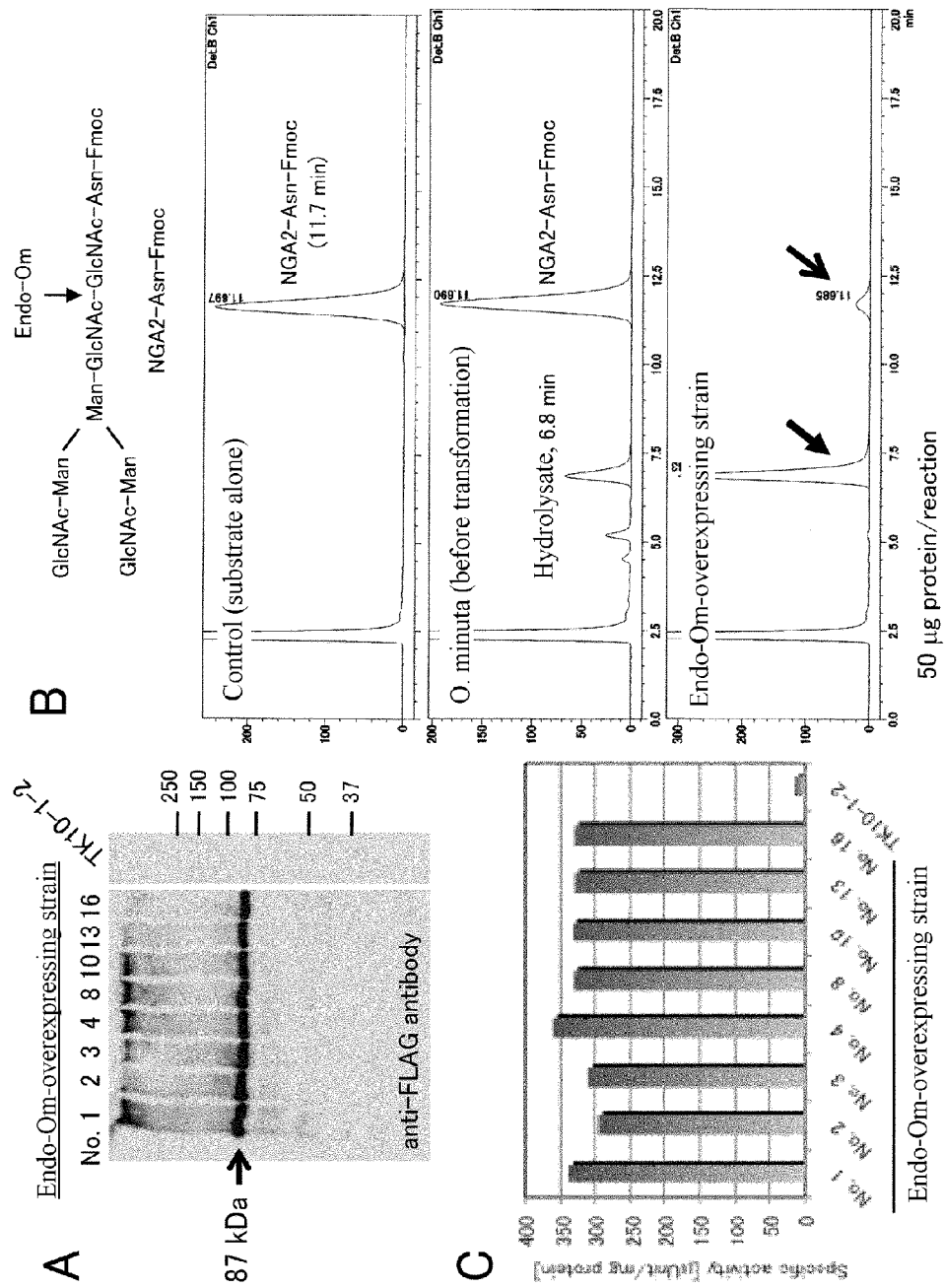
FIG. 3 shows the measurement result of protein expression and enzymatic activity in the Endo-Om-overexpressing *O. minuta* strain. A: confirmation of overexpression of Endo-Om by Western blotting; B: result of detection of enzyme reaction by HPLC; C: specific activity of Endo-Om-overexpressing strain.

The results of Western blotting are shown in FIG. 3A. For the Endo-Om-overexpressing strain, the signal of FLAG-tag was detected at the position corresponding to 87 kDa which is identical to the molecular mass of Endo-Om, and protein expression was confirmed.

The enzyme activity was measured as follows. A reaction solution (total volume: 10 μl) containing 100 mM of a sodium acetate buffer (pH 5.3) at the final concentration, 0.5 M NaCl, 10 μM of a Fmoc-labeled biantennary complex type sugar chain (NGA2-Asn-Fmoc), and an Endo-Om crude enzyme solution was incubated at 50° C. for 1 hour, and heated at 95° C. for 5 minutes, thereby stopping the enzyme reaction. The reaction solution was subjected to HPLC, and the enzymatic activity was calculated from the peak area ratio between the NGA2-Asn-Fmoc as the substrate and its hydrolysate. The column was Asahipak NH2P-50 4E (4.6.250 mm, Shodex), and the solvents were acetonitrile (solvent A) and 200 mM of TEAA (pH 7.0, GLEN RESEARCH: solvent B). Isocratic elution was carried out at a flow rate of 1.0 ml/min, and the solvent B: 43%, and detection was carried out using a fluorescence detector (excitation wavelength 265 nm, and fluorescence wavelength 315 nm). The activity hydrolyzing 1 vol of NGA2-Asn-Fmoc in 1 minute under the above-described reaction conditions was defined as 1 Unit of the enzymatic activity of Endo-Om.

The detection result of the enzyme reaction by HPLC is shown in FIG. 3B. Firstly, the biantennary complex type sugar chain (NGA2-Asn-Fmoc) alone as the substrate was subjected to HPLC; a peak was detected at the position of 11.7 min. Subsequently, each of the crude enzyme solutions of the O. minuta strain before transformation and the Endo-Om-overexpressing strain was allowed to react at the ratio of 50 µg protein/reaction, and the activities were compared. For the Endo-Om-overexpressing strain, the peak of the substrate remarkably decreased in comparison with the strain before transformation, and the peak of the hydrolysate GlcNAc-Asn-Fmoc (6.8 min) increased. This result indicates that Endo-Om is the enzyme of O. minuta hydrolyzing the biantennary complex type sugar chain.

Subsequently, the specific activity of the Endo-Om-overexpressing strain was compared, and the result is shown in FIG. 3C. For the TK10-1-2 strain before transformation, the specific activity was 15.0 [µUnit/mg protein] when 10 µM of NGA2-Asn-Fmoc was used as the substrate. For the Endo-Om-overexpressing strain, the specific gravity increased to 295 to 339 [µUnit/mg protein] (20 to 24 times the before transformation).

Example 5

Study of Properties of Endo-Om (5-1) Preparation of Endo-Om Purified Enzyme Solution, Calculation of Specific Activity Km, and Vmax The properties of Endo-Om were studied using a purified enzyme solution. According to the method described in Example 4, the Endo-Om crude enzyme solution prepared from 100 ml culture was substituted with an equilibration buffer (20 mM sodium phosphate buffer (pH 7.4), 0.5 M NaCl, 0.5 mM PMSF, 50 mM imidazole) by dialysis. The Endo-Om crude enzyme solution after dialysis was subjected to a HisTrap HP column (GE Healthcare), washed with the equilibration buffer, and eluted stepwise by an equilibration buffer containing 50 mM, 100 mM, and 200 mM of imidazole, thereby eluting the protein. The fraction containing Endo-Om eluted from the column was subjected to ultrafiltration concentration using Amicon Ultra (50,000 NMWL, Millipore), further dialyzed with 20 mM of sodium phosphate buffer (pH 7.4) and 0.5 M of NaCl, and glycerol was added to make the final concentration 10%, thereby making an Endo-Om purified enzyme solution. According to the method described in Example 4, the activity of the Endo-Om purified enzyme solution when the substrate concentration was 1 mM was measured, and the specific activity was calculated. In addition, activity measurement was carried out using NGA2-Asn-Fmoc at different concentrations as the substrates, and Km and Vmax were calculated. For comparison, the specific activity, Km, and Vmax of the commercially available Endo-M were calculated by the same method. The optimal pH of Endo-M is 6.0 (Non Patent Literature 6), so that the pH of the sodium acetate buffer was made 6.0 when measuring the activity of Endo-M.

Figure 4:
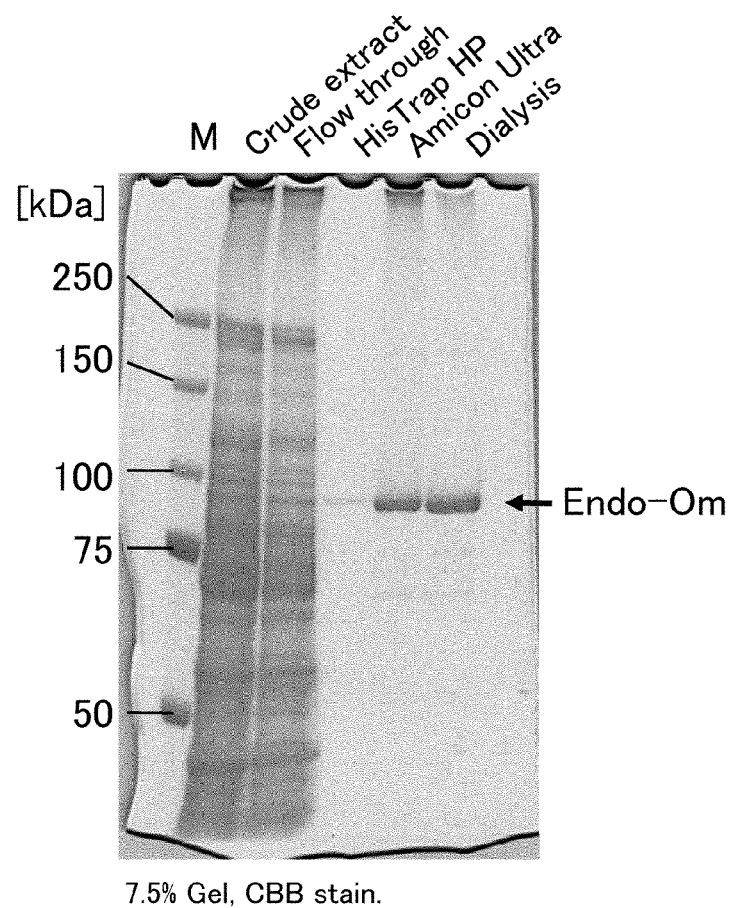
FIG. 4 shows the SDS-PAGE result of a purified sample of the recombinant Endo-Om.
Figure 5:
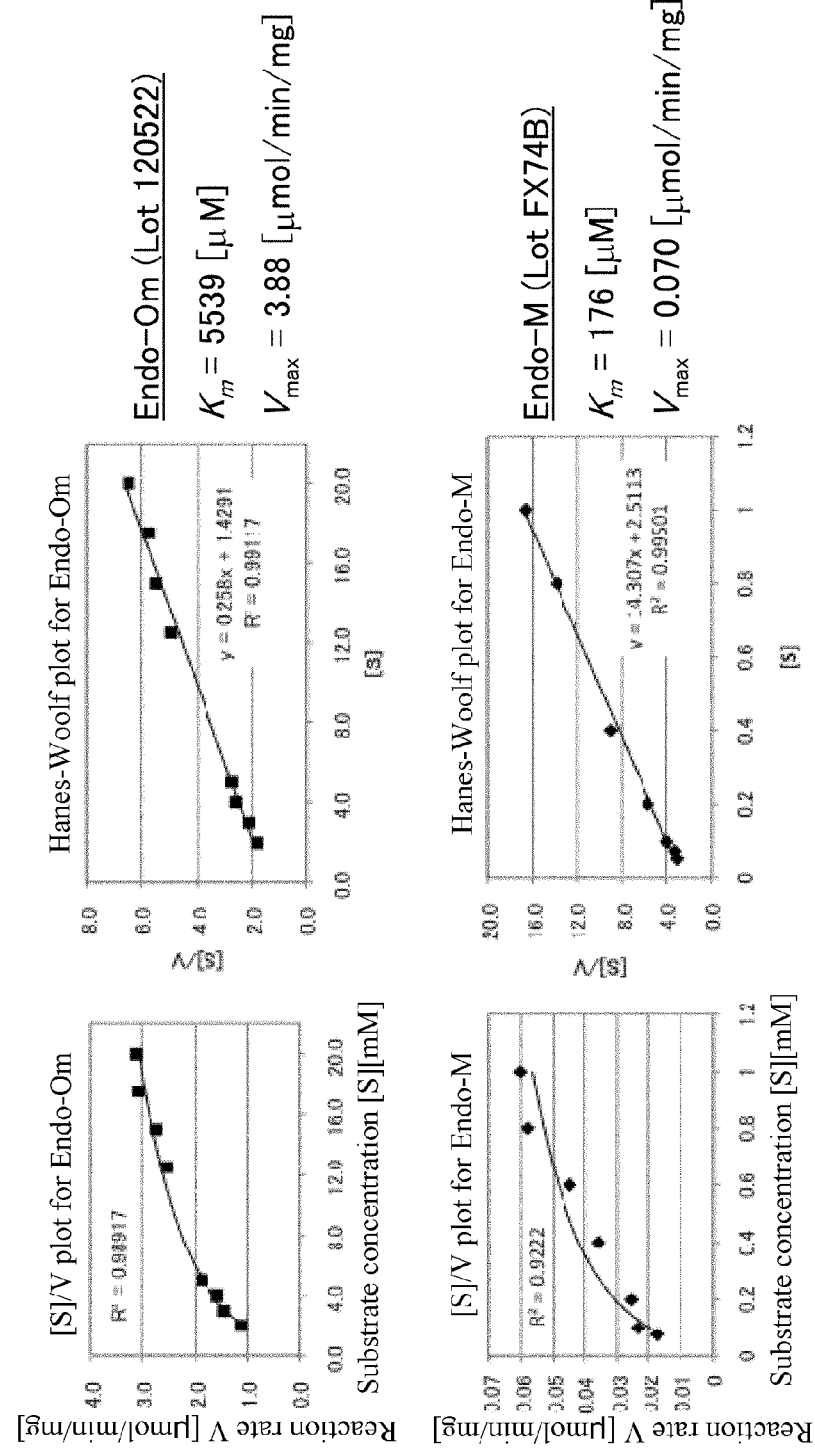
FIG. 5 shows the measurement results of Km and Vmax of Endo-Om and commercially available Endo-M.

The purification result of Endo-Om is shown in FIG. 4. Endo-Om was purified to a single band on SDS-PAGE. The specific activity of the purified Endo-Om was 0.80 mmol/min/mg when 1 mM of NGA2-Asn-Fmoc was used as the substrate. The specific activity of the commercially available Endo-M under the measurement conditions was 0.06 vol/min/mg, indicated that the specific activity of Endo-Om is about 13 times that of Endo-M. In addition, activity measurement was carried out using NGA2-Asn-Fmoc at different concentrations as the substrates, and Km and Vmax were calculated; the Km and Vmax of Endo-Om were 5539 µM and 3.88 mmol/min/mg, respectively, which were 31 times the Km (176 µM) and 55 times the Vmax (0.070 µmol/min/mg) of the commercially available Endo-M (FIG. 5).

(5-2) Study of Optimal Reaction Conditions for Endo-Om

Study of the optimal reaction pH for Endo-Om was carried out as follows. A reaction solution containing any of various buffers having a final concentration of 100 mM, 0.5 M of NaCl, 10 µM of NGA2-Asn-Fmoc, and an Endo-Om purified enzyme solution (total volume: 10 µl) was incubated at 50° C. for 1 hour, and heated at 95° C. for 5 minutes, thereby stopping the enzyme reaction. The buffers used herein were a sodium citrate buffer (pH 3.5-5.5), a sodium acetate buffer (pH 4.5-6.0), a sodium phosphate buffer (pH 6.0-7.5), a MOPS-NaOH buffer (pH 6.5-8.0), and a Tris-HCl buffer (pH 8.0-9.0). The reaction solution was subjected to HPLC by the method described in Example 4, and the enzymatic activity was calculated. The optimal reaction temperature was studied by changing the reaction temperature in the activity measurement method described in Example 4 in the range of 10° C. to 60° C.

Figure 6:
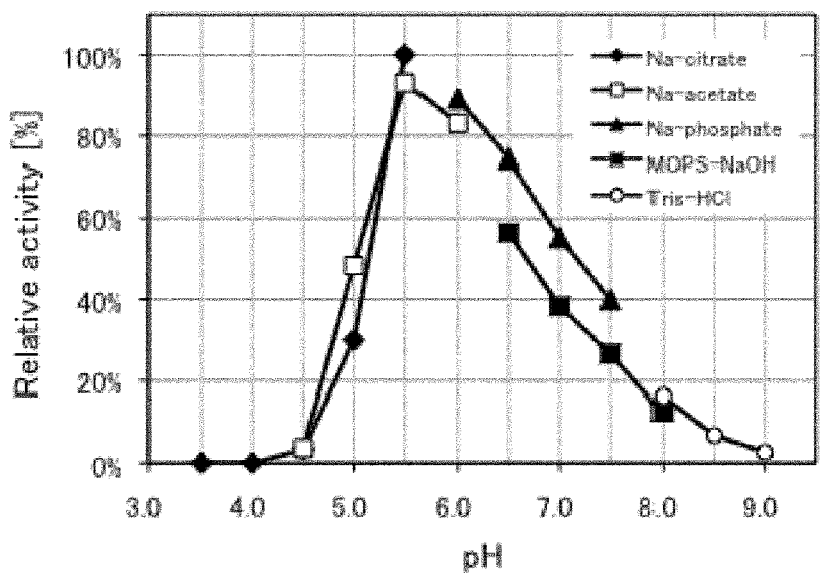
FIG. 6 shows the measurement results of optimal reaction conditions (pH and temperature) of Endo-Om: A: optimal pH; and B: optimal temperature.
Figure 6:
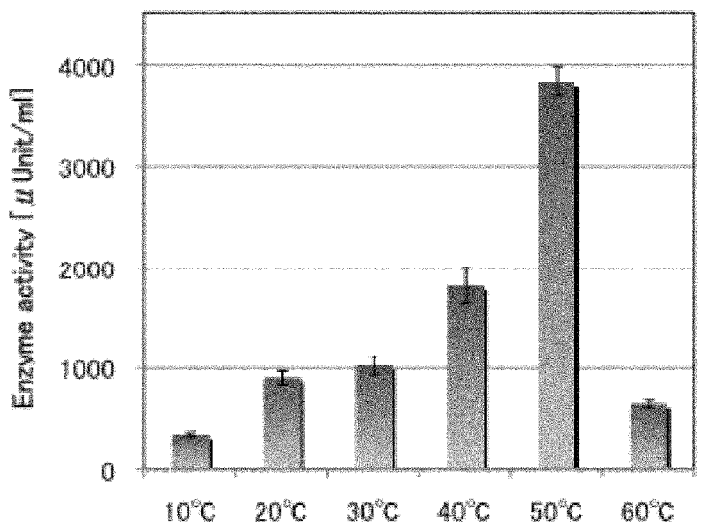

The measurement results of the optimal reaction conditions for Endo-Om are shown in FIG. 6. The optimal reaction pH for Endo-Om was about 5.5, and the optimal reaction temperature was about 50° C.

(5-3) Study of Hydrolysis Activity for Various Sugar Chains

Comparison of hydrolysis activity for PA-labeled sugar chains having various structures was carried out as follows. A reaction solution containing a sodium acetate buffer at final concentration of 100 mM (pH 5.3), 0.5 M of NaCl, 1 µM of any of various PA-labeled sugar chains (TaKaRa-Bio Inc.), and an Endo-Om purified enzyme solution (total volume: 10 µl) was incubated at 30° C. for 3 to 12 hours, and heated at 95° C. for 5 minutes thereby stopping the enzyme reaction. The reaction solution was subjected to HPLC, and enzymatic activity was calculated from the peak area ratio between the PA-labeled sugar chain as the substrate and its hydrolysate. The column used herein was Cosmosil 5C18-ARII (2.0.150 mm, Nacalai Tesque, Inc.), the solvents were a 0.1 M ammonium acetate buffer (pH 4.0: solvent A), a 0.1 M ammonium acetate buffer (pH 4.0), and 0.5% 1-butanol (solvent B). Linear gradient elution was carried out using the solvent B: 5%-50% at a flow rate of 0.5 ml/min over a period of 24 minutes, and detection was carried out using a fluorescence detector (excitation wavelength 320 nm, and fluorescence wavelength 400 nm). The enzymatic activity was calculated with the activity hydrolyzing 1 µmol of the PA-labeled sugar chain in 1 minute under the above-described reaction conditions as 1 Unit, and the relative activity for various sugar chains were calculated with the hydrolysis activity for the sugar chain having an M8A structure as 100%.

The measurement results of the hydrolysis activity of Endo-Om for PA-labeled sugar chains having various structures are shown in Table 1. For comparison, the data from the past literature concerning Endo-M (Non Patent Literature 6) was cited. Endo-Om showed as high hydrolysis activity for a high-mannose sugar chain as Endo-M, and also hydrolyzed a hybrid type sugar chain and a biantennary complex type sugar chain. On the other hand, it was revealed that Endo-Om cannot hydrolyzes a triantennary or more highly branched complex type sugar chain and a sugar chain having a core fucose structure. In addition, reactivity for several sugar chains was different from that of Endo-M, and higher reactivity was exhibited particularly for sugar chains having agalacto biantennary, M3B, M6B, and M9A structures than Endo-M.

(5-4) Study of the Presence or Absence of Transglycosidase Activity

Same ENGases are known to have activity for hydrolyzing a sugar chain and transferring the cleaved sugar chain to any acceptor molecule. Typical examples of such ENGase include Endo-M. Therefore, the presence or absence of sugar transfer activity (transglycosidase activity) of Endo-Om was studied.

The transglycosidase activity of Endo-Om was detected as follows. The reaction solution containing a sodium acetate buffer at a final concentration of 100 mM (pH 6.0), 2 mM NGA2-Asn-Fmoc, 50 mM acceptor molecule (p-nitrophenylglucose), and an Endo-Om purified enzyme solution (total volume: 10 µl) was incubated at 30° C. for 3 hours, and heated at 95° C. for 5 minutes to stop the enzyme reaction. The total amount of the reaction solution was subjected to HPLC by the method described in Example 4, and detection was carried out using a UV detector (274 nm). In addition, the peak corresponding to a transglycosylation product was collected, freeze-dried, and then redissolved in Milli-Q water and subjected to mass spectrometry using MALDI-QIT-TOFMS (AXIMA-QIT, Shimadzu Co., Ltd.), thereby identifying the transglycosylation product.

The result of the detection of transglycosylation activity of Endo-Om is shown in FIG. 7. In the reaction system containing no acceptor, transglycosylation will not occur, so that only the peaks of NGA2-Asn-Fmoc as the donor (10.8 min) and GlcNAc-Asn-Fmoc as the hydrolysate (6.6 min) were detected. In the reaction solution containing an acceptor, the peak of the hydrolysate and a new peak likely attributable to the transglycosylation product (4.15 min) were detected. These peaks were collected, and subjected to MS analysis; a molecular ion peak which corresponds to the predicted molecular weight of the transglycosylation product was detected (m/z=1389 [M+Na—$O_2$]$^+$, m/z=1405 [M+Na—O]$^+$, m/z=1421 [M+Na]$^+$, m/z=1437 [M+K]$^+$). These results suggest that Endo-Om has activity for transferring the cleaved sugar chain to any acceptor molecule.

Example 6

Cloning of *Candida parapolymorpha* DL-1-Derived ENGase (Endo-Cp) Gene

Based on the amino acid sequence of Endo-Om, BLAST search was carried out for the NCBI amino acid sequence database. As a result of this, genes partially having high homologies were detected in several yeasts (FIG. 2). Among them, the gene derived from *Candida parapolymorpha* DL-1 (*Hansenula polymorpha* DL-1) had a homology of 53.9% with the amino acid sequence of Endo-Om, but annotation was not described as ENGase in the database. Therefore, cloning of the Endo-Cp gene and the construction of the protein expression system were studied.

The genome DNA of the *Candida parapolymorpha* DL-1 ATCC26012 strain was extracted by a common procedure, and the ORF full-length sequence of the Endo-Cp gene was amplified by the PCR method using the primer 3 (SEQ ID NO. 7) and the primer 4 (SEQ ID NO. 8).

```
Primer 3:
                                      (SEQ ID NO. 7)
5'-TCGAAGGTAGGCATATGCCTCGAAACACAGCTAA-3'

Primer 4:
                                      (SEQ ID NO. 8)
5'-GCTTGAATTCGGATCCTCAAATGTGCATATCGGTACCCT-3'
```

The PCR product thus obtained was purified, the PCR product was incorporated into the protein expression plasmid pCold I DNA for *E. coli* (TaKaRa-Bio Inc.), which had been cleaved by Nde I and BamHI, using In-Fusion™ HD Cloning Kit (Clontech), thereby constructing pCold I-Endo-Cp. DNA sequencing of the purified vector was carried out, and the full-length nucleotide sequence of the Endo-Cp gene was determined.

The nucleotide sequence and amino acid sequence of the Endo-Cp gene obtained by cloning are shown in FIG. 8. The ORF of Endo-Cp including 2238 bases, and coded a protein including 745 amino acids and having a molecular weight of 86,500. The estimated isoelectric point was 5.61. Endo-Cp had the sequence which is highly conserved in GH family 85 ENGase belonging to the GH18 Chitinase-like superfamily at the position of about 75 to 410 amino acids on the N-terminal side.

Example 7

Preparation of Endo-Cp Expressing *E. coli* Strain

The pCold I-Endo-Cp of Example 6 was introduced into the *E. coli* competent cell for protein expression (NEB Express Competent *E. coli* (High Efficiency), NEW ENGRAND BioLabs). The transformed *E. coli* was spread out to an LB agar medium containing 100 µg/ml of ampicillin (2.5% LB Broth, Miller (Difco), 1.5% Agar), and cultured overnight at 37° C., thereby obtaining the transformant colonies. The colonies were picked up from the plate, amplification of the Endo-Cp gene was confirmed by the simple PCR method including suspension in a PCR reaction solution, and the colonies were used as the Endo-Cp-expressing *E. coli* strain.

Example 8

Expression Induction of Endo-Cp and Preparation of Partially Purified Enzyme Solution The Endo-Cp-expressing *E. coli* strain was inoculated into 5 ml of an LB medium, and cultured at 37° C. overnight. The total amount of the *E. coli* preculture was added to 500 ml of the LB medium, and cultured at 37° C. for about 3 hours, thereby growing the *E. coli* cells until the OD value reached about 0.5. Thereafter, IPTG was added to make the final concentration 1.0 mM, and quenched to 15° C. to give a cold shock, thereby inducing protein expression. After culturing at 15° C. for 48 hours, the *E. coli* cells were collected, and an extraction buffer (50 mM sodium phosphate buffer (pH 7.4), 1.25 M NaCl, 1 mM PMSF, 1× Complete (Roche), 5% glycerol) and glass beads were added, and shaken vigorously to crush the bacterial cells. The supernatant from which insoluble matter was removed by centrifugation was used as the Endo-Cp crude enzyme solution. The Endo-Cp crude enzyme solution was substituted with an equilibration buffer (20 mM sodium phosphate buffer (pH 7.4), 0.5 M NaCl, 0.5 mM PMSF, 50 mM imidazole) by dialysis. The Endo-Cp crude enzyme solution after dialysis was subjected to an HisTrap HP column (GE Healthcare), washed with an equilibration buffer, and then eluted stepwise by an equilibration buffer containing 50 mM, 100 mM, and 200 mM of imidazole in stages, thereby eluting the protein. The fraction containing Endo-Cp eluted from the column was subjected to ultrafiltration concentration using Amicon Ultra (50,000 NMWL, Millipore), further dialyzed with 20 mM of sodium phosphate buffer (pH 7.4) and 0.5 M of NaCl, and glycerol was added to make the final concentration 10%, thereby making an Endo-Cp partially purified enzyme solution.

Western blotting was carried out as follows. The Endo-Cp partially purified enzyme solution was denatured by an SDS sample buffer, and subjected to Western blotting by a common procedure. Using a mouse anti-Tetra-His antibody as the primary antibody, and an anti-mouse IgG antibody horseradish peroxidase conjugate was used as the secondary antibody, and ECL plus system (GE Healthcare) and a chemiluminescence detector (GE Healthcare) were used for detection.

The enzyme activity was measured as follows. A reaction solution (total volume: 10 µl) containing 100 mM of a sodium acetate buffer (pH 5.3) at the final concentration, 0.5 M NaCl, 10 µM of a Fmoc-labeled biantennary complex type sugar chain (NGA2-Asn-Fmoc), and Endo-Cp was incubated at 30° C. for 3 hours, and heated at 95° C. for 5 minutes, thereby stopping the enzyme reaction. The reaction solution was subjected to HPLC, and the enzymatic activity was calculated from the peak area ratio between the NGA2-Asn-Fmoc as the substrate and its hydrolysate. The column was Asahipak NH2P-50 4E (4.6.250 mm, Shodex), and the solvents were acetonitrile (solvent A) and 200 mM of TEAA (pH 7.0, GLEN RESEARCH: solvent B). Isocratic elution was carried out at a flow rate of 1.0 ml/min, and the solvent B: 43%, and detection was carried out using a fluorescence detector (excitation wavelength 265 nm, and fluorescence wavelength 315 nm). The activity hydrolyzing 1 µmol of NGA2-Asn-Fmoc in 1 minute under the above-described reaction conditions was defined as 1 Unit of the enzymatic activity of Endo-Cp.

Figure 9:
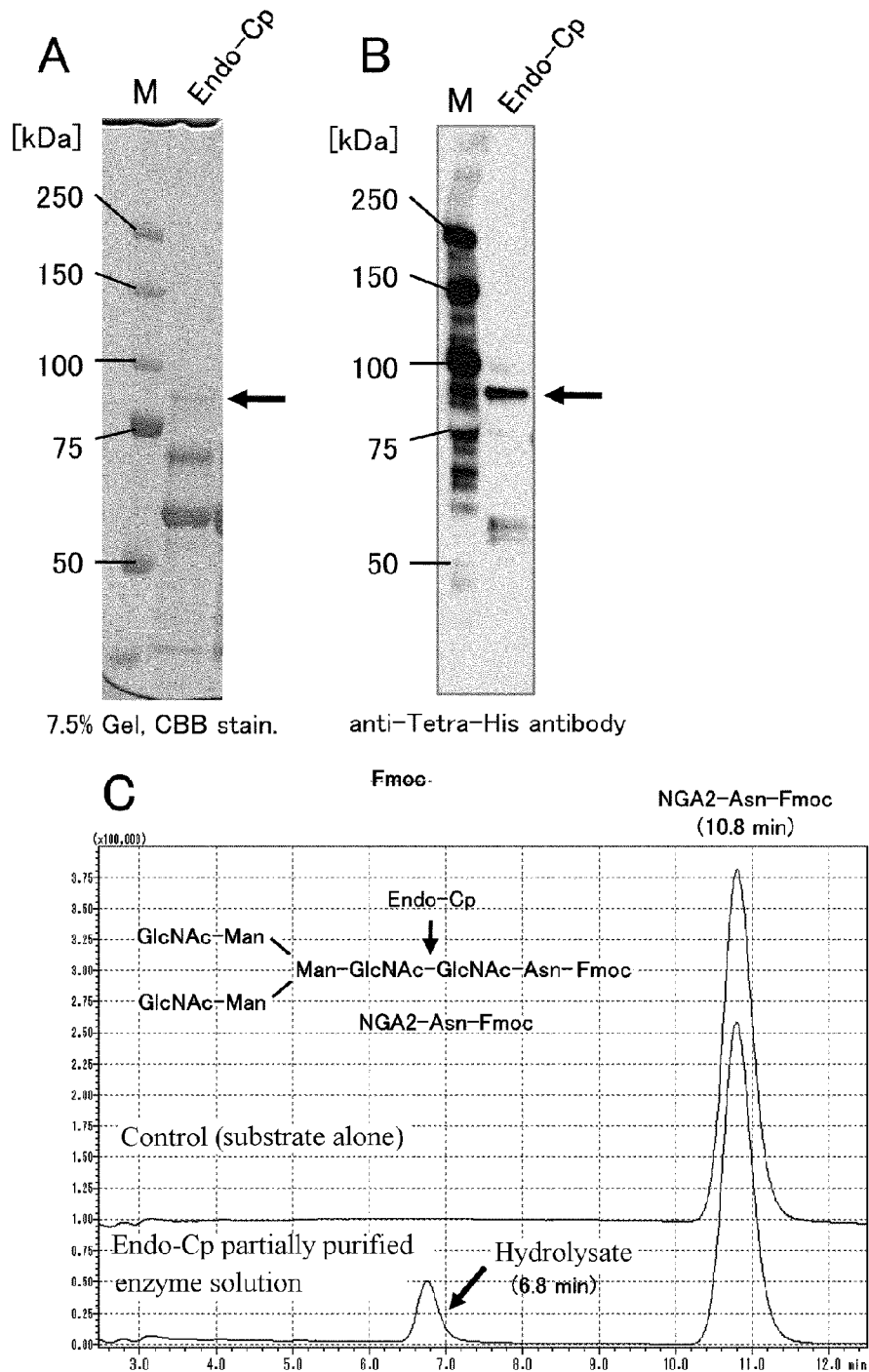
FIG. 9 shows the results of SDS-PAGE, Western blotting, and enzyme activity measurement of the Endo-Cp partially purified enzyme solution. A: SDS-PAGE; B: Western blotting; and C: detection of enzymatic activity HPLC.

The results of SDS-PAGE, Western blotting, and activity measurement of the Endo-Cp partially purified enzyme solution are shown in FIG. 9. Plural bands were detected in SDS-PAGE, and a signal of His-tag was detected in Western blotting at the position corresponding to 86.5 kDa which is identical to the molecular mass of Endo-Cp, indicating the successful protein expression (FIGS. 9A and 9B). The activity was measured using the biantennary complex type sugar chain (NGA2-Asn-Fmoc) as the substrate; the peak of the substrate (10.8 min) decreased for the reaction solution containing the Endo-Cp partially purified enzyme solution, and the peak (6.8 min) of the hydrolysate GlcNAc-Asn-Fmoc appeared (FIG. 9C). These results revealed that Endo-Cp is an ENGase which hydrolyzes a biantennary complex type sugar chain in the same manner as the known Endo-M. The specific activity of the Endo-Cp partially purified enzyme solution was 120 µUnit/mg.

Example 9

Study of Properties of Endo-Cp (9-1) Study of Optimal Reaction Conditions for Endo-Cp Study of the optimal reaction pH for Endo-Cp was carried out as follows. A reaction solution containing any of various buffers having a final concentration of 100 mM, 0.5 M of NaCl, 10 µM of NGA2-Asn-Fmoc, and an Endo-Cp partially purified enzyme solution (total volume: 10 µl) was incubated at 30° C. for 3 hours, and heated at 95° C. for 5 minutes, thereby stopping the enzyme reaction. The buffers used herein were a sodium citrate buffer (pH 3.5-5.5), a sodium acetate buffer (pH 4.5-6.0), a sodium phosphate buffer (pH 6.0-7.5), a MOPS-NaOH buffer (pH 6.5-8.0), and a Tris-HCl buffer (pH 8.0-9.0). The reaction solution was subjected to HPLC by the method described in Example 8, and the enzymatic activity was calculated. The optimal reaction temperature was studied by changing the reaction temperature in the activity measurement method described in Example 8 in the range of 10° C. to 70° C.

Figure 10:
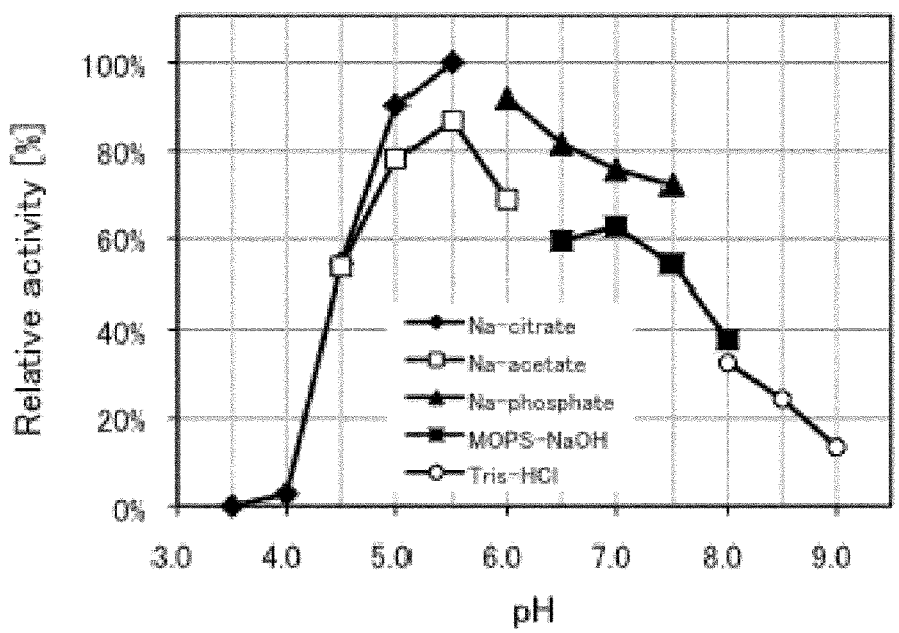
FIG. 10 shows the measurement results of the optimal reaction conditions (pH and temperature) of Endo-Cp. A: optimal pH; and B: optimal temperature.
Figure 10:
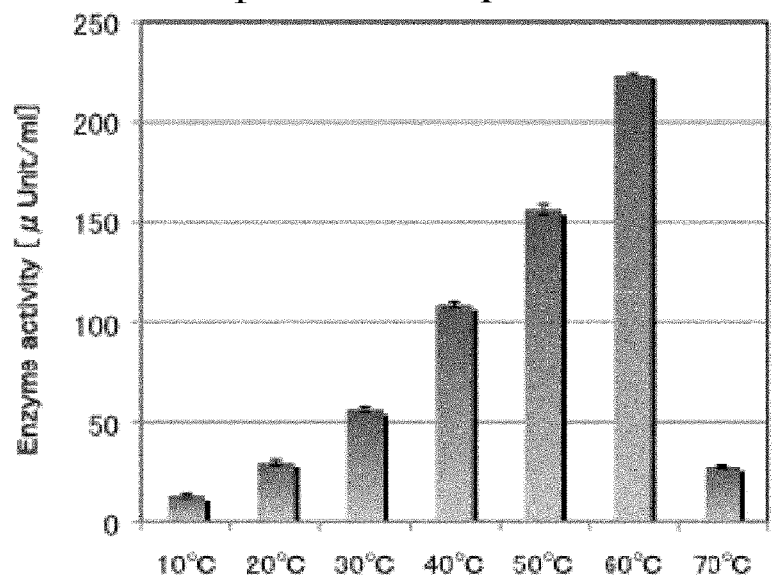

The measurement results of the optimal reaction conditions for Endo-Cp are shown in FIG. 10. The optimal reaction pH for Endo-Cp was about 5.5, and the optimal reaction temperature was about 60° C.

(9-2) Study of Hydrolysis Activity for Various Sugar Chains

Comparison of hydrolysis activity for PA-labeled sugar chains having various structures was carried out as follows. A reaction solution containing a sodium acetate buffer at final concentration of 100 mM (pH 5.3), 0.5 M of NaCl, 1 µM of any of various PA-labeled sugar chains (TaKaRa-Bio Inc.), and an Endo-Cp partially purified enzyme solution (total volume: 10 µl) was incubated at 30° C. for 3 to 12 hours, and heated at 95° C. for 5 minutes thereby stopping the enzyme reaction. The reaction solution was subjected to HPLC, and enzymatic activity was calculated from the peak area ratio between the PA-labeled sugar chain as the substrate and its hydrolysate. The column used herein was Cosmosil 5C18-ARII (2.0.150 mm, Nacalai Tesque, Inc.), the solvents were a 0.1 M ammonium acetate buffer (pH 4.0: solvent A), a 0.1 M ammonium acetate buffer (pH 4.0), and 0.5% 1-butanol (solvent B). Linear gradient elution was carried out using the solvent B: 5%-50% at a flow rate of 0.5 ml/min over a period of 24 minutes, and detection was carried out using a fluorescence detector (excitation wavelength 320 nm, and fluorescence wavelength 400 nm). The enzymatic activity was calculated with the activity hydrolyzing 1 µmol of the PA-labeled sugar chain in 1 minute under the above-described reaction conditions as 1 Unit, and the relative activity for various sugar chains were calculated with the hydrolysis activity for the sugar chain having an M8A structure as 100%.

The measurement results of the hydrolysis activity of Endo-Cp for PA-labeled sugar chains having various structures are shown in Table 2. For comparison, the data from the past literature concerning Endo-M (Non Patent Literature 6) was cited. Endo-Cp showed as high hydrolysis activity for a high-mannose sugar chain as Endo-M, and also hydrolyzed a hybrid type sugar chain and a biantennary complex type sugar chain. On the other hand, it was revealed that Endo-Om cannot hydrolyzes a triantennary or more highly branched complex type sugar chain and a sugar chain having a core fucose structure. In addition, reactivity for several sugar chains was different from that of Endo-M, and higher reactivity was exhibited particularly for sugar chains having agalacto biantennary, M3B, and M6B structures than Endo-M.

(9-3) Study of the Presence or Absence of Transglycosidase Activity

Same ENGases are known to have activity for hydrolyzing a sugar chain and transferring the cleaved sugar chain to any acceptor molecule. Typical examples of such ENGase include Endo-M. Therefore, the presence or absence of sugar transfer activity (transglycosidase activity) of Endo-Cp was studied.

The transglycosidase activity of Endo-Cp was detected as follows. The reaction solution containing a sodium acetate buffer at a final concentration of 100 mM (pH 6.0), 2 mM NGA2-Asn-Fmoc, 50 mM acceptor molecule (p-nitrophenylglucose), and an Endo-Cp partially purified enzyme solution (total volume: 10 µl) was incubated at 30° C. for 3 hours, and heated at 95° C. for 5 minutes to stop the enzyme reaction. The total amount of the reaction solution was subjected to HPLC by the method described in Example 8, and detection was carried out using a UV detector (274 nm). In addition, the peak corresponding to a transglycosylation product was collected, freeze-dried, and then redissolved in Milli-Q water and subjected to mass spectrometry using MALDI-QIT-TOFMS (A•MA-QIT, Shimadzu Co., Ltd.), thereby identifying the transglycosylation product.

The result of the detection of transglycosylation activity of Endo-Cp is shown in FIG. 11. For comparison, the result for Endo-Om is also shown. The Endo-Cp was allowed to react in the reaction system containing an acceptor; the peak of the transglycosylation product (4.15 min) was detected besides the peak of the hydrolysate in the same manner as Endo-Om. The peak was collected, and subjected to MS analysis; a molecular ion peak which corresponds to the predicted molecular weight of the transglycosylation product was detected (m/z=1389 [M+Na—$O_2$]$^+$, m/z=1405 [M+Na—O]$^+$, m/z=1421 [M+Na]$^+$, m/z=1437 [M+K]$^+$). These results suggest that Endo-Cp has activity for transferring the cleaved sugar chain to any acceptor molecule.

Example 10

Cloning of *Pichia anomala*-Derived ENGase (Endo-Pa) Gene

Based on the amino acid sequence of Endo-Om, BLAST search was carried out for the NCBI amino acid sequence database. As a result of this, genes partially having high homologies were found in several yeasts (FIG. 2). Among them, the gene derived from *Pichia anomala* had a homology of 42.5% with the amino acid sequence of Endo-Om, but annotation was not described as ENGase in the database. Therefore, cloning of the Endo-Pa gene and the construction of the protein expression system were studied.

The genome DNA of *Pichia anomala* ATCC36904 strain was extracted by a common procedure, and the ORF full length sequence of the Endo-Pa gene was amplified by the PCR method using the primer 5 (SEQ ID NO. 11) and primer 6 (SEQ ID NO. 12).

```
Primer 5:
                                    (SEQ ID NO. 11)
5'-TCGAAGGTAGGCATATGCAACATGATCATGCTGCCATA-3'

Primer 6:
                                    (SEQ ID NO. 12)
5'-GCTTGAATTCGGATCCCTATATAAATATATCCTCGCCTTTG-3'
```

The PCR product thus obtained was purified, the PCR product was incorporated into the protein expression plasmid pCold I DNA for *E. coli* (TaKaRa-Bio Inc.), which had been cleaved by Nde I and BamHI, using In-Fusion™ HD Cloning Kit (Clontech), thereby constructing pCold I-Endo-Pa. DNA sequencing of the purified vector was carried out, and the full-length nucleotide sequence of the Endo-Pa gene was determined.

The nucleotide sequence and amino acid sequence of the Endo-Pa gene obtained by cloning are shown in FIG. 12. The ORF of Endo-Pa including 1971 bases, and coded a protein including 656 amino acids and having a molecular weight of 76,050. The estimated isoelectric point was 6.06. Endo-Pa had the sequence which is highly conserved in GH family 85 ENGase belonging to the GH18 Chitinase-like superfamily at the position of about 65 to 400 amino acids on the N-terminal side.

Example 11

Preparation of Endo-Pa Expressing *E. Coli* Strain

The pCold I-Endo-Pa of Example 10 was introduced into the *E. coli* competent cell for protein expression (NEB Express Competent *E. coli* (High Efficiency), NEW ENGRAND BioLabs). The transformed *E. coli* was spread out to an LB agar medium containing 100 µg/ml of ampicillin (2.5% LB Broth, Miller (Difco), 1.5% Agar), and cultured overnight at 37° C., thereby obtaining the transformant colonies. The colonies were picked up from the plate, amplification of the Endo-Pa gene was confirmed by the simple PCR method including suspension in a PCR reaction solution, and the colonies were used as the Endo-Pa-expressing *E. coli* strain.

Example 12

Expression Induction of Endo-Pa and Preparation of Partially Purified Enzyme Solution The Endo-Pa-expressing *E. coli* strain was inoculated into 5 ml of an LB medium, and cultured at 37° C. overnight. The total amount of the *E. coli* preculture was added to 500 ml of the LB medium, and cultured at 37° C. for about 3 hours, thereby growing the *E. coli* cells until the OD value reached about 0.5. Thereafter, IPTG was added to make the final concentration 1.0 mM, and quenched to 15° C. to give a cold shock, thereby inducing protein expression. After culturing at 15° C. for 48 hours, the bacterial cells were collected, and an extraction buffer (50 mM sodium phosphate buffer (pH 7.4), 1.25 M NaCl, 1 mM PMSF, 1× Complete (Roche), 5% glycerol) and glass beads were added, and shaken vigorously to crush the bacterial cells. The supernatant from which insoluble matter was removed by centrifugation was used as the Endo-Pa crude enzyme solution. The Endo-Pa crude enzyme solution was substituted with an equilibration buffer (20 mM sodium phosphate buffer (pH 7.4), 0.5 M NaCl, 0.5 mM PMSF, 50 mM imidazole) by dialysis. The Endo-Pa crude enzyme solution after dialysis was subjected to an HisTrap HP column (GE Healthcare), washed with an equilibration buffer, and then eluted stepwise by an equilibration buffer containing 50 mM, 100 mM, and 200 mM of imidazole in stages, thereby eluting the protein. The fraction containing Endo-Pa eluted from the column was subjected to ultrafiltration concentration using Amicon Ultra (50,000 NMWL, Millipore), further dialyzed with 20 mM of sodium phosphate buffer (pH 7.4) and 0.5 M of NaCl, and glycerol was added to make the final concentration 10%, thereby making an Endo-Pa partially purified enzyme solution.

Western blotting was carried out as follows. The Endo-Pa partially purified enzyme solution was denatured by an SDS sample buffer, and subjected to Western blotting by a common procedure. Using a mouse anti-Tetra-His antibody as the primary antibody, and an anti-mouse IgG antibody horseradish peroxidase conjugate was used as the secondary antibody, and ECL plus system (GE Healthcare) and a chemiluminescence detector (GE Healthcare) were used for detection.

The enzyme activity was measured as follows. A reaction solution (total volume: 10 μl) containing 100 mM of a sodium acetate buffer (pH 5.3) at the final concentration, 0.5 M NaCl, 10 μM of a Fmoc-labeled biantennary complex type sugar chain (NGA2-Asn-Fmoc), and Endo-Pa was incubated at 30° C. for 3 hours, and heated at 95° C. for 5 minutes, thereby stopping the enzyme reaction. The reaction solution was subjected to HPLC, and the enzymatic activity was calculated from the peak area ratio between the NGA2-Asn-Fmoc as the substrate and its hydrolysate. The column was Asahipak NH2P-50 4E (4.6.250 mm, Shodex), and the solvents were acetonitrile (solvent A) and 200 mM of TEAA (pH 7.0, GLEN RESEARCH: solvent B). Isocratic elution was carried out at a flow rate of 1.0 ml/min, and the solvent B: 43%, and detection was carried out using a fluorescence detector (excitation wavelength 265 nm, and fluorescence wavelength 315 nm). The activity hydrolyzing 1 μmol of NGA2-Asn-Fmoc in 1 minute under the above-described reaction conditions was defined as 1 Unit of the enzymatic activity of Endo-Pa.

Figure 13:
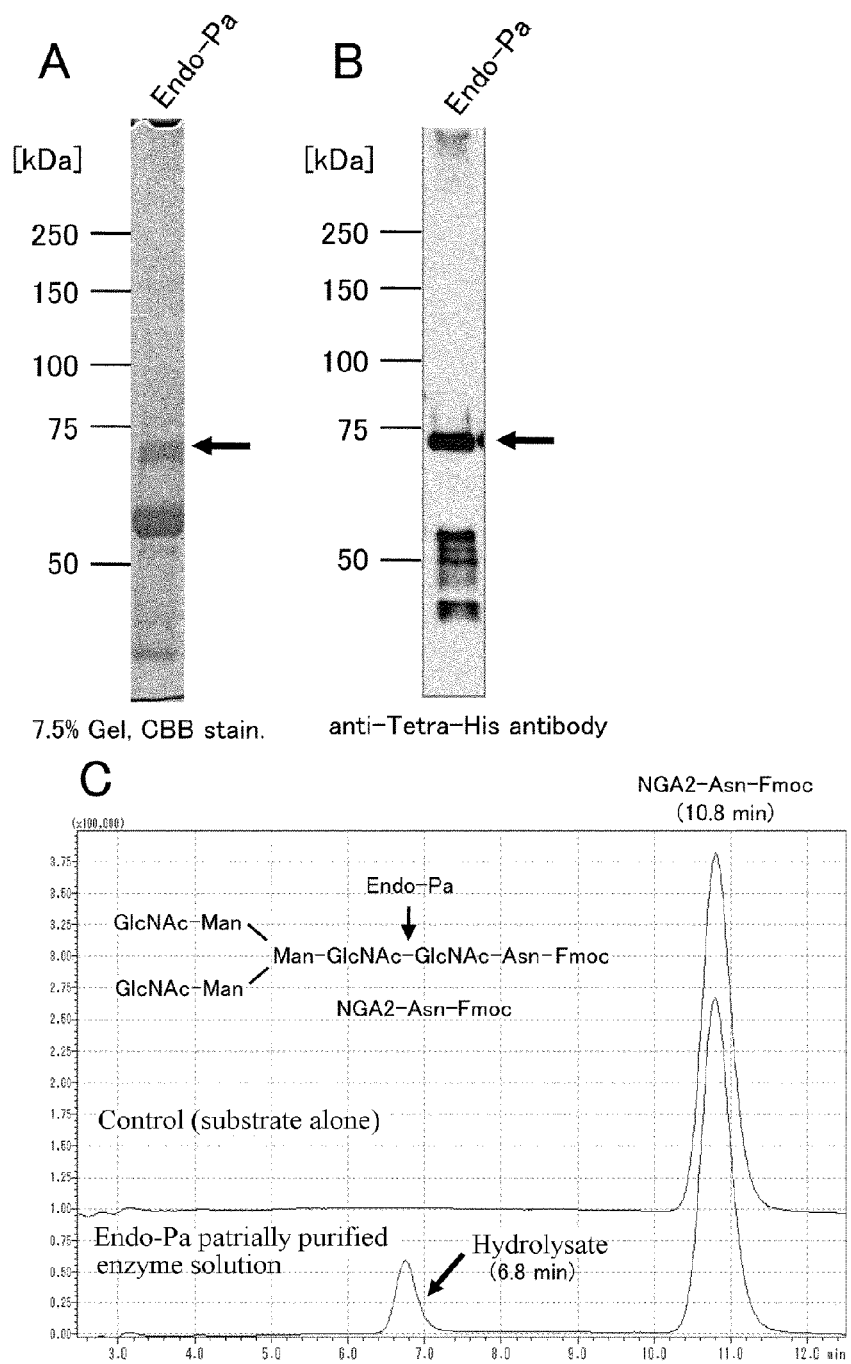
FIG. 13 shows the measurement results of SDS-PAGE, Western blotting, and enzyme activity of the Endo-Pa partially purified enzyme solution. A: SDS-PAGE; B: Western blotting; and C: detection of enzymatic activity by HPLC.

The results of SDS-PAGE, Western blotting, and activity measurement of the Endo-Pa partially purified enzyme solution are shown in FIG. 13. Plural bands were detected in SDS-PAGE, and a signal of His-tag was detected in Western blotting at the position slightly below 76 kDa which is identical to the molecular weight predicted from the sequence, indicating the successful protein expression (FIGS. 13A and 13B). The activity was measured using the biantennary complex type sugar chain (NGA2-Asn-Fmoc) as the substrate; the peak of the substrate (10.8 min) decreased for the reaction solution containing the Endo-Pa partially purified enzyme solution, and the peak (6.8 min) of the hydrolysate GlcNAc-Asn-Fmoc appeared (FIG. 13C). These results revealed that Endo-Pa is an ENGase which hydrolyzes a biantennary complex type sugar chain in the same manner as the known Endo-M. The specific activity of the Endo-Pa partially purified enzyme solution was 353 μUnit/mg.

Example 13

Study of Properties of Endo-Pa (13-1) Study of Optimal Reaction Conditions for Endo-Pa Study of the optimal reaction pH for Endo-Pa was carried out as follows. A reaction solution containing any of various buffers having a final concentration of 100 mM, 0.5 M of NaCl, 10 μM of NGA2-Asn-Fmoc, and an Endo-Pa partially purified enzyme solution (total volume: 10 μl) was incubated at 30° C. for 3 hours, and heated at 95° C. for 5 minutes, thereby stopping the enzyme reaction. The buffers used herein were a sodium citrate buffer (pH 3.5-5.5), a sodium acetate buffer (pH 4.5-6.0), a sodium phosphate buffer (pH 6.0-7.5), a MOPS-NaOH buffer (pH 6.5-8.0), and a Tris-HCl buffer (pH 8.0-9.0). The reaction solution was subjected to HPLC by the method described in Example 12, and the enzymatic activity was calculated. The optimal reaction temperature was studied by changing the reaction temperature in the activity measurement method described in Example 12 in the range of 10° C. to 60° C.

Figure 14:
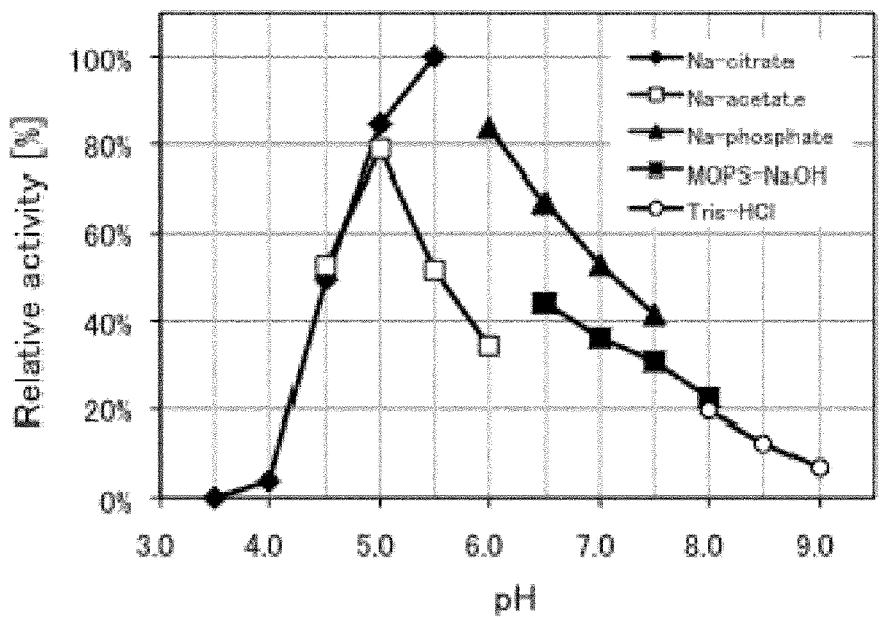
FIG. 14 shows the measurement results the optimal reaction conditions (pH and temperature) of Endo-Pa. A: optimal pH; and B: optimal temperature.
Figure 14:
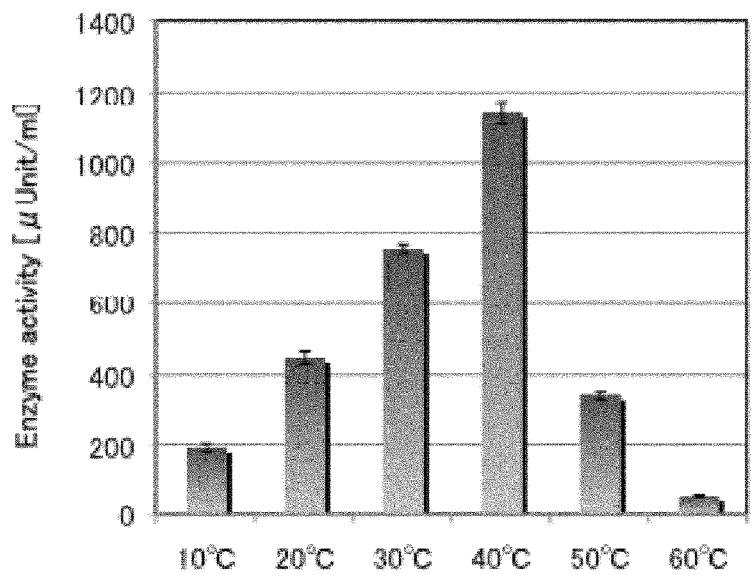

The measurement results of the optimal reaction conditions for Endo-Pa are shown in FIG. 14. The optimal reaction pH for Endo-Pa was between 5.0-5.5, and the optimal reaction temperature was about 40° C.

(13-2) Study of Hydrolysis Activity for Various Sugar Chains

Comparison of hydrolysis activity for PA-labeled sugar chains having various structures was carried out as follows. A reaction solution containing a sodium acetate buffer at final concentration of 100 mM (pH 5.3), 0.5 M of NaCl, 1 μM of any of various PA-labeled sugar chains (TaKaRa-Bio Inc.), and an Endo-Pa partially purified enzyme solution (total volume: 10 μl) was incubated at 30° C. for 3 to 12 hours, and heated at 95° C. for 5 minutes thereby stopping the enzyme reaction. The reaction solution was subjected to HPLC, and enzymatic activity was calculated from the peak area ratio between the PA-labeled sugar chain as the substrate and its hydrolysate. The column used herein was Cosmosil 5C18-ARII (2.0.150 mm, Nacalai Tesque, Inc.), the solvents were a 0.1 M ammonium acetate buffer (pH 4.0: solvent A), a 0.1 M ammonium acetate buffer (pH 4.0), and 0.5% 1-butanol (solvent B). Linear gradient elution was carried out using the solvent B: 5%-50% at a flow rate of 0.5 ml/min over a period of 24 minutes, and detection was carried out using a fluorescence detector (excitation wavelength 320 nm, and fluorescence wavelength 400 nm). The enzymatic activity was calculated with the activity hydrolyzing 1 μmol of the PA-labeled sugar chain in 1 minute under the above-described reaction conditions as 1 Unit, and the relative activity for various sugar chains were calculated with the hydrolysis activity for the sugar chain having an M8A structure as 100%.

The measurement results of the hydrolysis activity of Endo-Pa for PA-labeled sugar chains having various structures are shown in Table 3. For comparison, the data from the past literature concerning Endo-M (Non Patent Literature 6) was cited. Endo-Pa showed as high hydrolysis activity for a high-mannose sugar chain as Endo-M, and also hydrolyzed a hybrid type sugar chain and a biantennary complex type sugar chain. On the other hand, it was revealed that Endo-Om cannot hydrolyzes a triantennary or more highly branched complex type sugar chain and a sugar chain having a core fucose structure. In addition, higher reactivity was exhibited for almost all sugar chains than Endo-M.

(13-3) Study of the Presence or Absence of Transglycosidase Activity

Same ENGases are known to have activity for hydrolyzing a sugar chain and transferring the cleaved sugar chain to any acceptor molecule. Typical examples of such ENGase include Endo-M. Therefore, the presence or absence of sugar transfer activity (transglycosidase activity) of Endo-Pa was studied.

The transglycosidase activity of Endo-Pa was detected as follows. The reaction solution containing a sodium acetate buffer at a final concentration of 100 mM (pH 6.0), 2 mM NGA2-Asn-Fmoc, 50 mM acceptor molecule (p-nitrophenylglucose), and an Endo-Pa partially purified enzyme solution (total volume: 10 μl) was incubated at 30° C. for 16 hours, and heated at 95° C. for 5 minutes to stop the enzyme reaction. The total amount of the reaction solution was subjected to HPLC by the method described in Example 12, and detection was carried out using a UV detector (274 nm). In addition, the peak corresponding to a transglycosylation product was collected, freeze-dried, and then redissolved in Milli-Q water and subjected to mass spectrometry using MALDI-QIT- TOFMS (AXIMA-QIT, Shimadzu Co., Ltd.), thereby identifying the transglycosylation product.

The result of the detection of transglycosylation activity of Endo-Pa is shown in FIG. 15. For comparison, the result for Endo-Om is also shown. The Endo-Pa was allowed to react in the reaction system containing an acceptor; the peak of the transglycosylation product (4.15 min) was newly detected besides the peak of the hydrolysate in the same manner as Endo-Om. The peak was collected, and subjected to MS analysis; a molecular ion peak which corresponds to the predicted molecular mass of the transglycosylation product was detected (m/z=1389 [M+Na—$O_2$]$^+$, m/z=1405 [M+Na—O]$^+$, m/z=1421 [M+Na]$^+$, m/z=1437 [M+K]$^+$). These results suggest that Endo-Pa has activity for transferring the cleaved sugar chain to any acceptor molecule.

Example 14

Cloning of *Zygosaccharomyces rouxii*-Derived ENGase (Endo-Zr) Gene

Based on the amino acid sequence of Endo-Om, BLAST search was carried out for the NCBI amino acid sequence database. As a result of this, genes partially having high homologies were detected in several yeasts (FIG. 2). Among them, the gene derived from *Zygosaccharomyces rouxii* had a homology of 30.6% with the amino acid sequence of Endo-Om, but annotation was not described as ENGase in the database. Therefore, cloning of the Endo-Zr gene and the construction of the protein expression system were studied.

The genome DNA of the *Zygosaccharomyces rouxii* ATCC2623 train was extracted by a common procedure, and the ORF full length sequence of the Endo-Zr gene was amplified by the PCR method using the primer 7 (SEQ ID NO. 15 and the primer 8 (SEQ ID NO. 16).

```
Primer 7:
                                   (SEQ ID NO. 15)
5'-TCGAAGGTAGGCATATGAAACGTATTAATCAGGT-3'

Primer 8:
                                   (SEQ ID NO. 16)
5'-GCTTGAATTCGGATCCTTACTTCTTGACTACGAATTTCAAAG-3'
```

The PCR product thus obtained was purified, the PCR product was incorporated into the protein expression plasmid pCold I DNA for *E. coli* (TaKaRa-Bio Inc.), which had been cleaved by Nde I and BamHI, using In-Fusion™ HD Cloning Kit (Clontech), thereby constructing pCold I-Endo-Zr. DNA sequencing of the purified vector was carried out, and the full-length nucleotide sequence of the Endo-Zr gene was determined.

The nucleotide sequence and amino acid sequence of the Endo-Zr gene obtained by cloning are shown in FIG. 16. The ORF of Endo-Zr including 1920 bases, and coded a protein including 639 amino acids and having a molecular weight of 73,105. The estimated isoelectric point was 6.69. Endo-Zr had the sequence which is highly conserved in GH family 85 ENGase belonging to the GH18 Chitinase-like superfamily at the position of about 70 to 400 amino acids on the N-terminal side.

Example 15

Preparation of Endo-Zr-Expressing *E. Coli* Strain

The pCold I-Endo-Zr of Example 14 was introduced into the *E. coli* competent cell for protein expression (NEB Express Competent *E. coli* (High Efficiency), NEW ENGRAND BioLabs). The transformed *E. coli* was spread out to an LB agar medium containing 100 μg/ml of ampicillin (2.5% LB Broth, Miller (Difco), 1.5% Agar), and cultured overnight at 37° C., thereby obtaining the transformant colonies. The colonies were picked up from the plate, amplification of the Endo-Zr gene was confirmed by the simple PCR method including suspension in a PCR reaction solution, and the colonies were used as the Endo-Zr-expressing *E. coli* strain.

Example 16

Expression Induction of Endo-Zr and Preparation of Partially Purified Enzyme Solution The Endo-Zr-expressing *E. coli* strain was inoculated into 5 ml of an LB medium, and cultured at 37° C. overnight. The total amount of the *E. coli* preculture was added to 500 ml of the LB medium, and cultured at 37° C. for about 3 hours, thereby growing the bacterial cells until the OD value reached about 0.5. Thereafter, IPTG was added to make the final concentration 1.0 mM, and quenched to 15° C. to give a cold shock, thereby inducing protein expression. After culturing at 15° C. for 48 hours, the *E. coli* cells were collected, and an extraction buffer (50 mM sodium phosphate buffer (pH 7.4), 1.25 M NaCl, 1 mM PMSF, 1× Complete (Roche), 5% glycerol) and glass beads were added, and shaken vigorously to crush the bacterial cells. The supernatant from which insoluble matter was removed by centrifugation was used as the Endo-Zr crude enzyme solution. The Endo-Zr crude enzyme solution was substituted with an equilibration buffer (20 mM sodium phosphate buffer (pH 7.4), 0.5 M NaCl, 0.5 mM PMSF, 50 mM imidazole) by dialysis. The Endo-Zr crude enzyme solution after dialysis was subjected to an HisTrap HP column (GE Healthcare), washed with an equilibration buffer, and then eluted by an equilibration buffer containing 50 mM, 100 mM, and 200 mM of imidazole in stages, thereby eluting the protein. The fraction containing Endo-Zr eluted from the column was subjected to ultrafiltration concentration using Amicon Ultra (50,000 NMWL, Millipore), further dialyzed with 20 mM of sodium phosphate buffer (pH 7.4) and 0.5 M of NaCl, and glycerol was added to make the final concentration 10%, thereby making an Endo-Zr partially purified enzyme solution.

Western blotting was carried out as follows. The Endo-Zr partially purified enzyme solution was denatured by an SDS sample buffer, and subjected to Western blotting by a common procedure. Using a mouse anti-Tetra-His antibody as the primary antibody, and an anti-mouse IgG antibody horseradish peroxidase conjugate was used as the secondary antibody, and ECL plus system (GE Healthcare) and a chemiluminescence detector (GE Healthcare) were used for detection.

The enzyme activity was measured as follows. A reaction solution (total volume: 10 μl) containing 100 mM of a sodium acetate buffer (pH 5.3) at the final concentration, 0.5 M NaCl, 10 μM of a Fmoc-labeled biantennary complex type sugar chain (NGA2-Asn-Fmoc), and Endo-Zr was incubated at 30° C. for 3 to 12 hours, and heated at 95° C. for 5 minutes, thereby stopping the enzyme reaction. The reaction solution was subjected to HPLC, and the enzymatic activity was calculated from the peak area ratio between the NGA2-Asn-Fmoc as the substrate and its hydrolysate. The column was Asahipak NH2P-50 4E (4.6.250 mm, Shodex), and the solvents were acetonitrile (solvent A) and 200 mM of TEAA (pH 7.0, GLEN RESEARCH: solvent B). Isocratic elution was carried out at a flow rate of 1.0 ml/min, and the solvent B:

43%, and detection was carried out using a fluorescence detector (excitation wavelength 265 nm, and fluorescence wavelength 315 nm). The activity hydrolyzing 1 µmol of NGA2-Asn-Fmoc in 1 minute under the above-described reaction conditions was defined as 1 Unit of the enzymatic activity of Endo-Zr.

Figure 17:
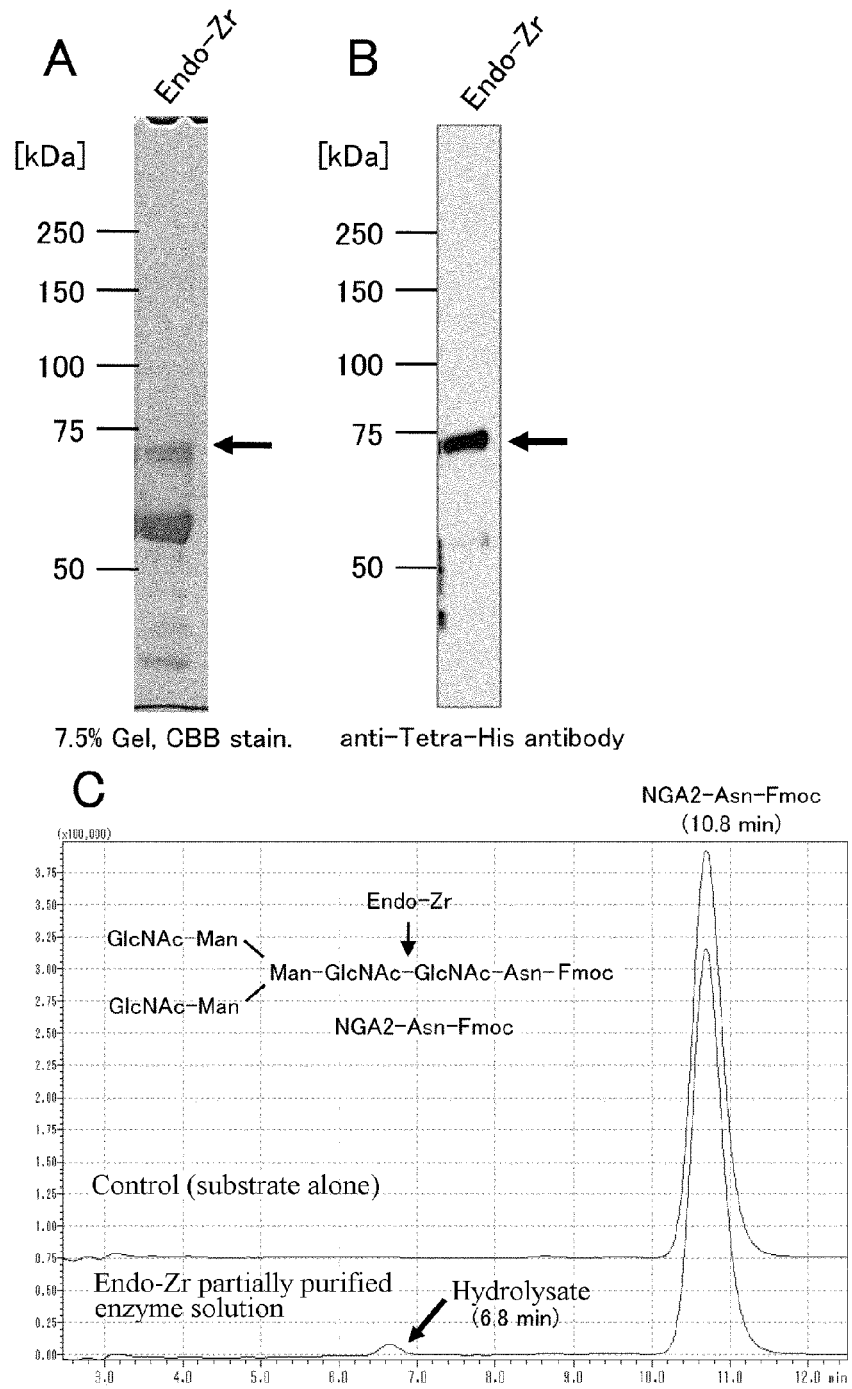
FIG. 17 shows the results of SDS-PAGE, Western blotting, and measurement of enzyme activity of the Endo-Zr partially purified enzyme solution. A; SDS-PAGE; B: Western blotting; and C: detection of enzymatic activity by HPLC.

The results of SDS-PAGE, Western blotting, and activity measurement of the Endo-Zr partially purified enzyme solution are shown in FIG. 17. Plural bands were detected in SDS-PAGE, and a signal of His-tag was detected in Western blotting at the position corresponding to 73 kDa which is identical to the molecular mass of Endo-Zr, indicating the protein expression (FIGS. 17A and 17B). The activity was measured using the biantennary complex type sugar chain (NGA2-Asn-Fmoc) as the substrate; the peak of the substrate (10.8 min) decreased for the reaction solution containing the Endo-Zr partially purified enzyme solution, and the peak (6.8 min) of the hydrolysate GlcNAc-Asn-Fmoc appeared (FIG. 17C). These results revealed that Endo-Zr is an ENGase which hydrolyzes a biantennary complex type sugar chain in the same manner as the known Endo-M. The specific activity of the Endo-Pa partially purified enzyme solution was 3.3 µUnit/mg.

Example 17

Study of Properties of Endo-Zr (17-1) Study of Optimal Reaction Conditions for Endo-Zr Study of the optimal reaction pH for Endo-Zr was carried out as follows. A reaction solution containing any of various buffers having a final concentration of 100 mM, 0.5 M of NaCl, 10 µM of NGA2-Asn-Fmoc, and an Endo-Zr partially purified enzyme solution (total volume: 10 µl) was incubated at 30° C. for 3 hours, and heated at 95° C. for 5 minutes, thereby stopping the enzyme reaction. The buffers used herein were a sodium citrate buffer (pH 3.5-5.5), a sodium acetate buffer (pH 4.5-6.0), a sodium phosphate buffer (pH 6.0-7.5), a MOPS-NaOH buffer (pH 6.5-8.0), and a Tris-HCl buffer (pH 8.0-9.0). The reaction solution was subjected to HPLC by the method described in Example 16, and the enzymatic activity was calculated. The optimal reaction temperature was studied by changing the reaction temperature in the activity measurement method described in Example 16 in the range of 10° C. to 60° C.

Figure 18:
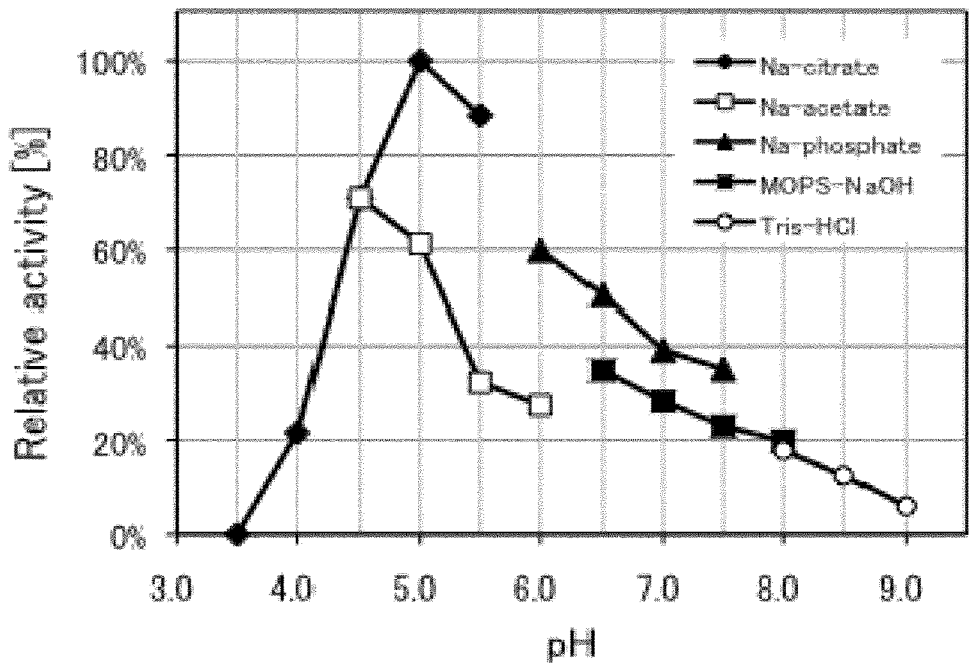
FIG. 18 shows the measurement results of the optimal reaction conditions (pH and temperature) of Endo-Zr. A: optimal pH; and B: optimal temperature.
Figure 18:
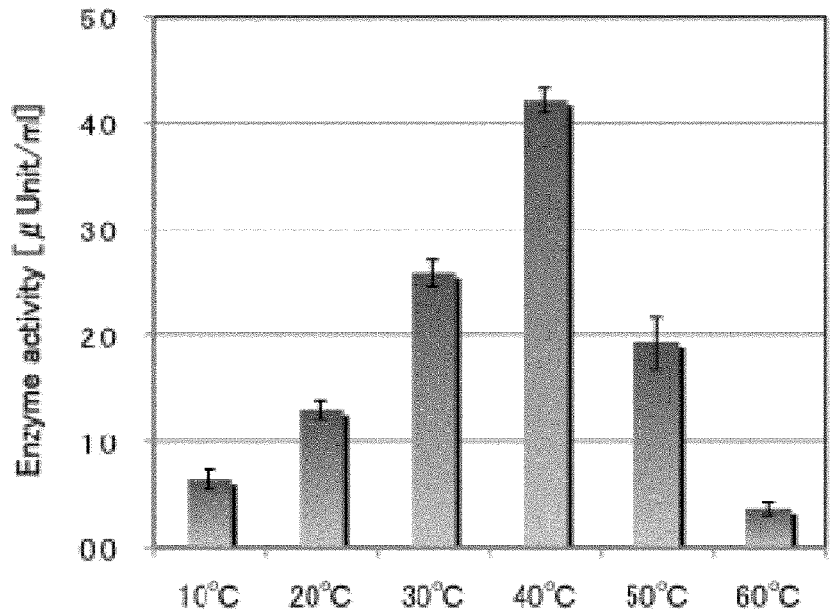

The measurement results of the optimal reaction conditions for Endo-Zr are shown in FIG. 18. The optimal reaction pH for Endo-Zr was between 4.5-5.0, and the optimal reaction temperature was about 40° C.

(17-2) Study of Hydrolysis Activity for Various Sugar Chains

Comparison of hydrolysis activity for PA-labeled sugar chains having various structures was carried out as follows. A reaction solution containing a sodium acetate buffer at final concentration of 100 mM (pH 5.3), 0.5 M of NaCl, 1 µM of any of various PA-labeled sugar chains (TaKaRa-Bio Inc.), and an Endo-Zr partially purified enzyme solution (total volume: 10 µl) was incubated at 30° C. for 3 to 12 hours, and heated at 95° C. for 5 minutes thereby stopping the enzyme reaction. The reaction solution was subjected to HPLC, and enzymatic activity was calculated from the peak area ratio between the PA-labeled sugar chain as the substrate and its hydrolysate. The column used herein was Cosmosil 5C18-ARII (2.0.150 mm, Nacalai Tesque, Inc.), the solvents were a 0.1 M ammonium acetate buffer (pH 4.0: solvent A), a 0.1 M ammonium acetate buffer (pH 4.0), and 0.5% 1-butanol (solvent B). Linear gradient elution was carried out using the solvent B: 5%-50% at a flow rate of 0.5 ml/min over a period of 24 minutes, and detection was carried out using a fluorescence detector (excitation wavelength 320 nm, and fluorescence wavelength 400 nm). The enzymatic activity was calculated with the activity hydrolyzing 1 µmol of the PA-labeled sugar chain in 1 minute under the above-described reaction conditions as 1 Unit, and the relative activity for various sugar chains were calculated with the hydrolysis activity for the sugar chain having an M8A structure as 100%.

The measurement results of the hydrolysis activity of Endo-Zr for PA-labeled sugar chains having various structures are shown in Table 4. For comparison, the data from the past literature concerning Endo-M (Non Patent Literature 6) was cited. Endo-Zr showed as high hydrolysis activity for a high-mannose sugar chain as Endo-M, and also hydrolyzed a hybrid type sugar chain and a biantennary complex type sugar chain. On the other hand, it was revealed that Endo-Zr cannot hydrolyzes a triantennary or more highly branched complex type sugar chain, a sugar chain having a core fucose structure, and a complex type sugar chain having a bisecting GlcNAc. In addition, it shows different reactivity for several sugar chains from Endo-M, and exhibits particularly higher reactivity for sugar chains having a biantennary M3B, M5A and M6B structures than Endo-M.

(17-3) Study of the Presence or Absence of Transglycosidase Activity

Same ENGases are known to have activity for hydrolyzing a sugar chain and transferring the cleaved sugar chain to any acceptor molecule. Typical examples of such ENGase include Endo-M. Therefore, the presence or absence of sugar transfer activity (transglycosidase activity) of Endo-Zr was studied.

The transglycosidase activity of Endo-Zr was detected as follows. The reaction solution containing a sodium acetate buffer at a final concentration of 100 mM (pH 6.0), 2 mM NGA2-Asn-Fmoc, 50 mM acceptor molecule (p-nitrophenylglucose), and an Endo-Zr partially purified enzyme solution (total volume: 10 µl) was incubated at 30° C. for 16 hours, and heated at 95° C. for 5 minutes to stop the enzyme reaction. The total amount of the reaction solution was subjected to HPLC by the method described in Example 16, and detection was carried out using a UV detector (274 nm).

As a result of the HPLC analysis, the peak of the transglycosylation product was not detected for the Endo-Zr sample, and transglycosidase activity was not confirmed (Data not shown).

[Sequence Free Text]
SEQ ID NO. 1: Endo-Om AA
SEQ ID NO. 2: Endo-Om (2319 bp)
SEQ ID NO. 3: primer 1 (Endo-Om primer F)
SEQ ID NO. 4: primer 2 (Endo-Om primer R)
SEQ ID NO. 5: Endo-Cp AA (*Candida parapolymorpha*)
SEQ ID NO. 6: Endo-Cp (*Candida parapolymorpha*) (2238 bp)
SEQ ID NO. 7: primer 3 (Endo-Cp primer F)
SEQ ID NO. 8: primer 4 (Endo-Cp primer R)
SEQ ID NO. 9: Endo-Pa AA (*Pichia anomala*)
SEQ ID NO. 10: Endo-Pa (*Pichia anomala*) (1971 bp)
SEQ ID NO. 11: primer 5 (Endo-Pa primer F)
SEQ ID NO. 12: primer 6 (Endo-Om primer R)
SEQ ID NO. 13: Endo-Zr AA (*Zygosaccharomyces rouxii*)

SEQ ID NO. 14: Endo-Zr (*Zygosaccharomyces rouxii*) (1920 bp)

SEQ ID NO. 15: primer 7 (Endo-Zr primer F)
SEQ ID NO. 16: primer 8 (Endo-Zr primer R)

The invention claimed is:

1. A cDNA which encodes a protein having endo-β-N-acetylglucosaminidase activity wherein the protein comprises an amino acid sequence selected from the group consisting of:
   (1) SEQ ID NO: 1;
   (2) the amino acid sequence obtained by deletion, substitution, insertion and/or addition of any of 1-20 amino acids in SEQ ID NO: 1,
   (3) the amino acid sequence having an identity of 90% or more with SEQ ID NO: 1;
   (4) the amino acid sequence encoded by SEQ ID NO: 2; and
   (5) the amino acid sequence encoded by the nucleotide sequence of the polynucleotide which hybridizes with the polynucleotide having the nucleotide sequence complementary to SEQ ID NO: 2 under stringent hybridization conditions of (a) 6×SSC (1×SSC is 0.15 M NaCl, 0.015 M sodium citrate, pH 7.0), 0.5% SDS, 5×Denhardt's (Denhardt's, 0.1% bovine serum albumin (BSA), 0.1% polyvinyl pyrrolidone, and 0.1% Ficoll 400) and 100 µg/ml salmon sperm DNA, at 50° C. for 4 hours to overnight, wherein a specific hybrid is formed and less than 10% of mismatch in the entire nucleotide sequence is allowed or (b) 2×SSC, 0.5% SDS, 25% formamide, 5×Denhardt's, and 100 µg/ml salmon sperm DNA, at 55° C. for 4 hours to overnight, wherein a specific hybrid is formed and less than 10% of mismatch in the entire nucleotide sequence is allowed.

2. A cDNA selected from the group consisting of:
   (1) cDNA comprising SEQ ID NO: 2;
   (2) cDNA which hybridizes with the polynucleotide having the nucleotide sequence complementary to SEQ ID NO: 2 under stringent hybridization conditions of (a) 6×SSC (1×SSC is 0.15 M NaCl, 0.015 M sodium citrate, pH 7.0), 0.5% SDS, 5×Denhardt's (Denhardt's, 0.1% bovine serum albumin (BSA), 0.1% polyvinyl pyrrolidone, and 0.1% Ficoll 400) and 100 µg/ml salmon sperm DNA, at 50° C. for 4 hours to overnight, wherein a specific hybrid is formed and less than 10% of mismatch in the entire nucleotide sequence is allowed or (b) 2×SSC, 0.5% SDS, 25% formamide, 5×Denhardt's, and 100 µg/ml salmon sperm DNA, at 55° C. for 4 hours to overnight, wherein a specific hybrid is formed and less than 10% of mismatch in the entire nucleotide sequence is allowed, and said cDNA encodes a protein having endo-β-N-acetylglucosaminidase activity; and
   (3) DNA having an identity of 90% or more with SEQ ID NO: 2, which is amplified by the primer set containing SEQ ID NO: 3 and 4, and encodes a protein having endo-β-N-acetylglucosaminidase activity.

3. A vector for expressing a protein having endo-β-N-acetylglucosaminidase activity, comprising the cDNA of claim 1.

4. A vector for expressing a protein having endo-β-N-acetylglucosaminidase activity, comprising the cDNA of claim 2.

5. A transformant for expressing a protein having endo-β-N-acetylglucosaminidase activity into which the vector of claim 3 is introduced.

6. The transformant of claim 5, wherein the transformant is hosted by yeast cells selected from any of the yeasts *Ogataea minuta*, *Candida parapolymorpha*, *Pichia anomala*, and *Zygosaccharomyces rouxii*.

7. A transformant for expressing a protein having endo-β-N-acetylglucosaminidase activity into which the vector of claim 4 is introduced.

8. The transformant of claim 7, wherein the transformant is hosted by yeast cells selected from any of the yeasts *Ogataea minuta*, *Candida parapolymorpha*, *Pichia anomala*, and *Zygosaccharomyces rouxii*.

9. A method for producing a protein having endo-β-N-acetylglucosaminidase activity, comprising the process of culturing the transformant of claim 5.

10. A method for producing a protein having endo-β-N-acetylglucosaminidase activity, comprising the process of culturing the transformant of claim 7.

11. The cDNA of claim 1, wherein the amino acid sequence of (3) is an amino acid sequence having an identity of 95% or more with SEQ ID NO: 1.

12. The cDNA of claim 2, wherein the cDNA of (3) is a cDNA having an identity of 95% or more with SEQ ID NO: 2, which is amplified by the primer set containing SEQ ID NO: 3 and 4, and encodes a protein having endo-β-N-acetylglucosaminidase activity.

* * * * *

SEQUENCE LISTING

<160> NUMBER OF SEQ ID NOS: 16

<210> SEQ ID NO 1
<211> LENGTH: 772
<212> TYPE: PRT
<213> ORGANISM: Ogataea minuta

<400> SEQUENCE: 1

```
Met Ala Gln Ser Gln Leu Leu Gly Gly Ala Val Arg Pro Val Phe Phe
1               5                   10                  15

Asp Lys Leu Glu Glu Leu Arg Arg Trp His Thr Gln Ser Ala Asn Leu
            20                  25                  30

Ser Arg Glu Ser Glu Leu Asp Ser Leu Asn Val Ala Thr Glu Pro Phe
        35                  40                  45

Ser Ser Tyr Glu Arg Ala Gln Thr Gly Ser Gly Ser Arg Ser Ser Glu
    50                  55                  60

Pro Val Pro Gly Asp Lys Glu Asp Pro Pro Ile Lys Leu Met Val Cys
65                  70                  75                  80

His Asp Phe Lys Gly Gly Tyr Gln Asp Tyr Glu Asp Ala Gln Pro Leu
                85                  90                  95

Gly Tyr Phe Pro His Pro Thr Gly Ser Arg Tyr Phe Leu Gln Tyr Pro
            100                 105                 110

Gln Leu Ile Asp Gln Phe Val Tyr Phe Ser His His Arg Val Thr Val
        115                 120                 125

Pro Pro Val Asn Trp Ile Asn Phe Cys His Arg Asn Gly Ile Lys Cys
    130                 135                 140

Phe Gly Thr Val Ile Phe Glu Gly Asn Ala Ser Lys Asp Phe Glu Glu
145                 150                 155                 160

Leu Asp Arg Leu Val Ser Arg Asp Glu Lys Gly Asp Phe Val Phe Val
                165                 170                 175

Asp Ala Leu Ile Lys Leu Ala Ala His Tyr Gly Phe Asp Gly Tyr Leu
            180                 185                 190

Leu Asn Ile Glu Thr Thr Phe Ser Asn Thr Lys Ile Ala Ala Asp Leu
        195                 200                 205

Glu Pro Phe Ala Glu Gln Leu Lys Ser Gly Leu His Cys Leu Asp Ser
    210                 215                 220

Lys Asn Glu Leu Ile Trp Tyr Asp Ser Tyr Val Phe Pro Ala Asn Lys
225                 230                 235                 240

Val Ser Tyr Thr Asn Gly Val Thr Glu Ser Asn Tyr Asn Phe Phe Ser
                245                 250                 255

Leu Ser Asp Ala Phe Phe Ser Asn Tyr Trp Trp Asn Ile Lys Asn Leu
            260                 265                 270

Gln Glu Asn Ile Lys Asn Val Gly Val Leu Gly Val Gln Lys Lys Ile
        275                 280                 285

Tyr Val Gly Tyr Asp Val Trp Gly Arg Gly Thr Leu Val Gly Lys Gly
    290                 295                 300

Gly Phe Asp Ser Ser Leu Ala Cys Lys Met Ile Ala Lys Phe Lys Ser
305                 310                 315                 320

Asn Val Ala Leu Phe Ala Pro Ala Trp Thr Tyr Glu Ser Leu Gly Pro
                325                 330                 335

Lys Asp Phe Asn Gln Asn Asp Ala Arg Phe Trp Ile Gly Leu Phe Glu
            340                 345                 350
```

-continued

```
Asn Glu Ser Ser Ile Ser Ser Thr Val Pro Pro His Ser Ala Val
            355                 360                 365
Tyr Lys Ile Asn Glu Ser Ser Phe Ile Phe Tyr Thr Asn Phe Ser Ser
370                 375                 380
Gly Glu Gly Asn Arg Phe Phe Ser Lys Gly Ser Glu Val Tyr Arg Lys
385                 390                 395                 400
Asn Trp Val Asn Gly Ser Leu Gln Phe Asp Leu Pro Ile Asp Leu His
                405                 410                 415
Arg Lys Asp Lys Asn Gly Leu Gln Trp Ala Leu Asp Lys Ser Asp Ala
            420                 425                 430
Phe His Gly Gly Ala Cys Leu Glu Ile Lys Tyr Ser Glu Ile Lys Asp
        435                 440                 445
Glu Asn Gly Tyr Gln Ile Phe Asn Asn Gln Met Val Ser Asp Phe Thr
    450                 455                 460
Leu Phe Asn Phe Thr Lys Glu Cys His Phe Pro Thr Val Asn Val Lys
465                 470                 475                 480
Val Thr Tyr Lys Leu Asn His Lys Thr Lys Ser Thr Phe Lys Ile Lys
                485                 490                 495
Ile Lys Tyr Ile Ile Glu Arg Arg Phe Arg Ser Val Gln Thr Val Arg
            500                 505                 510
Thr Gly Tyr Leu Thr Ile Pro Leu Leu Ser Thr Ser Gly Lys Trp Phe
        515                 520                 525
Thr Val Glu Glu Ser Phe Gln Ile Asn Leu Gln Thr Ser His Glu Tyr
    530                 535                 540
Ile Val Leu Glu Ser Ala His Val Thr Tyr Asp Glu Asp Arg Ser Ala
545                 550                 555                 560
Asp Ser Phe Phe Arg Ser Tyr Ile Val Glu Asp Ser Ala Ile Thr Ser
                565                 570                 575
Val Ile Asp Asn Glu Glu Tyr Glu Lys Leu Ile Asn Ser Glu Ile Tyr
            580                 585                 590
Asn Asp Asp Glu Asp Glu Asp Trp Ile Leu Val Pro Ser Asp Val Ser
        595                 600                 605
Ile Ser Ser Ser Glu Ser Gln Ser Asn Asp Ser Lys Thr Gln Tyr Leu
    610                 615                 620
Gly Arg Lys Leu Phe Gly Asn Lys Ser Thr Pro Lys Thr Arg Thr Leu
625                 630                 635                 640
Glu Gly Thr Ala Pro Leu Leu Arg Ile Gly Glu Phe Ala Ile Ile Ser
                645                 650                 655
Ala Asn Asn Tyr Pro Ser Ser Asn Phe Leu Ala Val Thr Ser Val Lys
            660                 665                 670
Ser Ile Glu Ser Ser Arg Leu Glu Gly Asp Ser Leu Val Leu Leu Asn
        675                 680                 685
Trp Gln Val Gly Glu Gly His Gln Lys Gly Val Cys Tyr Tyr Ile Ile
    690                 695                 700
Tyr Val Asn Gly Ala Val Val Gly Leu Ser Val Ala Pro Lys Phe Ile
705                 710                 715                 720
Tyr Gln Asp Thr Glu Leu Ala Ser Glu Asn Ser Ala Ser Ala Arg Ser
                725                 730                 735
Asn Tyr Lys Lys Ser Gly Leu Gly Ser Ser Asp Arg Lys Ser Lys
            740                 745                 750
Val Arg Val Asp Ser Val Asp Lys Leu Gly Asn Val Phe Thr Gly Ser
        755                 760                 765
Glu Val Trp Val
```

```
<210> SEQ ID NO 2
<211> LENGTH: 2319
<212> TYPE: DNA
<213> ORGANISM: Ogataea minuta
<220> FEATURE:
<221> NAME/KEY: CDS
<222> LOCATION: (1)..(2316)
<220> FEATURE:
<221> NAME/KEY: terminator
<222> LOCATION: (2317)..(2319)

<400> SEQUENCE: 2 atg gcg caa tct cag cta ctg ggc ggt gca gtg cgc cca gtt ttc ttc      48
Met Ala Gln Ser Gln Leu Leu Gly Gly Ala Val Arg Pro Val Phe Phe
1               5                   10                  15 gac aaa ctg gaa gag ctc cgg cgt tgg cac acc cag tca gcg aat ttg      96
Asp Lys Leu Glu Glu Leu Arg Arg Trp His Thr Gln Ser Ala Asn Leu
            20                  25                  30 tcc aga gag tcg gaa ttg gac agt ctc aac gtt gca act gaa cca ttt     144
Ser Arg Glu Ser Glu Leu Asp Ser Leu Asn Val Ala Thr Glu Pro Phe
        35                  40                  45 tcc tcc tac gag agg gca caa acc ggg tct gga tcc cgg tcc agc gag     192
Ser Ser Tyr Glu Arg Ala Gln Thr Gly Ser Gly Ser Arg Ser Ser Glu
    50                  55                  60 cca gtc cct gga gac aaa gag gac cct cct atc aag ctg atg gtt tgc     240
Pro Val Pro Gly Asp Lys Glu Asp Pro Pro Ile Lys Leu Met Val Cys
65                  70                  75                  80 cac gat ttc aaa ggc ggc tat cag gac tac gag gac gcc cag cct ttg     288
His Asp Phe Lys Gly Gly Tyr Gln Asp Tyr Glu Asp Ala Gln Pro Leu
                85                  90                  95 ggc tat ttt ccc cac cca acc ggc tcg agg tac ttc ttg cag tat ccg     336
Gly Tyr Phe Pro His Pro Thr Gly Ser Arg Tyr Phe Leu Gln Tyr Pro
            100                 105                 110 cag ctc ata gac cag ttc gtt tac ttt agt cac cac aga gtc acc gtt     384
Gln Leu Ile Asp Gln Phe Val Tyr Phe Ser His His Arg Val Thr Val
        115                 120                 125 ccg cct gtg aac tgg atc aat ttc tgc cat aga aac ggg ata aaa tgc     432
Pro Pro Val Asn Trp Ile Asn Phe Cys His Arg Asn Gly Ile Lys Cys
    130                 135                 140 ttt gga act gtc atc ttt gaa ggt aat gcg tcg aag gat ttt gaa gag     480
Phe Gly Thr Val Ile Phe Glu Gly Asn Ala Ser Lys Asp Phe Glu Glu
145                 150                 155                 160 ctg gac cga ttg gtt tct cgc gat gaa aag gga gac ttt gtc ttt gtg     528
Leu Asp Arg Leu Val Ser Arg Asp Glu Lys Gly Asp Phe Val Phe Val
                165                 170                 175 gac gca ttg att aag ctg gct gcg cat tac ggt ttc gac ggc tat ctt     576
Asp Ala Leu Ile Lys Leu Ala Ala His Tyr Gly Phe Asp Gly Tyr Leu
            180                 185                 190 ctc aac att gaa act acg ttc agc aac acc aag att gcg gct gac ttg     624
Leu Asn Ile Glu Thr Thr Phe Ser Asn Thr Lys Ile Ala Ala Asp Leu
        195                 200                 205 gag ccg ttt gct gaa cag ctc aag tca ggt ctc cat tgt ctg gat tca     672
Glu Pro Phe Ala Glu Gln Leu Lys Ser Gly Leu His Cys Leu Asp Ser
    210                 215                 220 aag aat gaa ctc atc tgg tac gac tca tac gtt ttc ccg gca aac aag     720
Lys Asn Glu Leu Ile Trp Tyr Asp Ser Tyr Val Phe Pro Ala Asn Lys
225                 230                 235                 240 gtt tcc tac acc aac ggg gtg acc gag tcg aat tac aac ttt ttc tca     768
Val Ser Tyr Thr Asn Gly Val Thr Glu Ser Asn Tyr Asn Phe Phe Ser
                245                 250                 255
```

```
ctg tcc gac gct ttt ttc tcc aat tac tgg tgg aac atc aaa aac ttg        816
Leu Ser Asp Ala Phe Phe Ser Asn Tyr Trp Trp Asn Ile Lys Asn Leu
        260                 265                 270 cag gag aac atc aaa aac gtt ggc gtg ttg ggc gtt cag aag aaa att        864
Gln Glu Asn Ile Lys Asn Val Gly Val Leu Gly Val Gln Lys Lys Ile
    275                 280                 285 tac gtc ggc tac gac gtc tgg ggc cgt gga acg ctg gtt ggc aaa gga        912
Tyr Val Gly Tyr Asp Val Trp Gly Arg Gly Thr Leu Val Gly Lys Gly
290                 295                 300 ggg ttt gac tcc agc ttg gcg tgc aaa atg att gca aag ttc aag tct        960
Gly Phe Asp Ser Ser Leu Ala Cys Lys Met Ile Ala Lys Phe Lys Ser
305                 310                 315                 320 aac gtt gcc cta ttt gcg cca gcg tgg acc tat gag agt ctg ggg ccg       1008
Asn Val Ala Leu Phe Ala Pro Ala Trp Thr Tyr Glu Ser Leu Gly Pro
                325                 330                 335 aaa gac ttc aat caa aat gac gcc cgg ttc tgg att ggt ctt ttt gaa       1056
Lys Asp Phe Asn Gln Asn Asp Ala Arg Phe Trp Ile Gly Leu Phe Glu
            340                 345                 350 aac gag tca tcc atc tcg tct acc gtc cct cca cac agc tct gct gtg       1104
Asn Glu Ser Ser Ile Ser Ser Thr Val Pro Pro His Ser Ser Ala Val
        355                 360                 365 tat aaa atc aac gag tcc agc ttc atc ttt tac acc aac ttc agt tcg       1152
Tyr Lys Ile Asn Glu Ser Ser Phe Ile Phe Tyr Thr Asn Phe Ser Ser
    370                 375                 380 ggt gaa gga aac aga ttt ttc agc aag ggg tcc gag gtg tac cga aag       1200
Gly Glu Gly Asn Arg Phe Phe Ser Lys Gly Ser Glu Val Tyr Arg Lys
385                 390                 395                 400 aat tgg gtc aat ggg agc ttg cag ttt gac ctc cct atc gac cta cac       1248
Asn Trp Val Asn Gly Ser Leu Gln Phe Asp Leu Pro Ile Asp Leu His
                405                 410                 415 cga aag gac aag aac gga ctc cag tgg gca ctg gat aag tcg gac gcg       1296
Arg Lys Asp Lys Asn Gly Leu Gln Trp Ala Leu Asp Lys Ser Asp Ala
            420                 425                 430 ttt cac ggc gga gca tgt cta gag atc aag tac agt gag ata aaa gac       1344
Phe His Gly Gly Ala Cys Leu Glu Ile Lys Tyr Ser Glu Ile Lys Asp
        435                 440                 445 gaa aac gga tat caa att ttc aac aac caa atg gtc agc gat ttc acc       1392
Glu Asn Gly Tyr Gln Ile Phe Asn Asn Gln Met Val Ser Asp Phe Thr
    450                 455                 460 ctg ttc aat ttc acc aaa gag tgt cat ttc cca acc gtc aac gtc aag       1440
Leu Phe Asn Phe Thr Lys Glu Cys His Phe Pro Thr Val Asn Val Lys
465                 470                 475                 480 gtg acc tac aag cta aac cac aaa aca aaa tca act ttc aag atc aaa       1488
Val Thr Tyr Lys Leu Asn His Lys Thr Lys Ser Thr Phe Lys Ile Lys
                485                 490                 495 atc aag tat atc att gaa aga aga ttc aga tct gtt caa aca gtc cgc       1536
Ile Lys Tyr Ile Ile Glu Arg Arg Phe Arg Ser Val Gln Thr Val Arg
            500                 505                 510 acg ggc tac ctc act att cca ctt ctt tca acc tct gga aaa tgg ttc       1584
Thr Gly Tyr Leu Thr Ile Pro Leu Leu Ser Thr Ser Gly Lys Trp Phe
        515                 520                 525 acg gtt gaa gaa tcc ttc caa atc aac ttg caa acc tct cac gag tac       1632
Thr Val Glu Glu Ser Phe Gln Ile Asn Leu Gln Thr Ser His Glu Tyr
    530                 535                 540 att gtc ctc gaa agt gcc cac gtc acg tac gat gaa gac aga agt gca       1680
Ile Val Leu Glu Ser Ala His Val Thr Tyr Asp Glu Asp Arg Ser Ala
545                 550                 555                 560 gac agt ttt ttc aga tct tac atc gtg gaa gac tct gct atc acg tca       1728
Asp Ser Phe Phe Arg Ser Tyr Ile Val Glu Asp Ser Ala Ile Thr Ser
```

```
                565                 570                 575
gtc att gac aac gag gag tac gaa aag ctg atc aac agc gag att tac        1776
Val Ile Asp Asn Glu Glu Tyr Glu Lys Leu Ile Asn Ser Glu Ile Tyr
            580                 585                 590 aat gac gat gaa gac gag gac tgg att ctc gtt ccc tct gac gtt tca        1824
Asn Asp Asp Glu Asp Glu Asp Trp Ile Leu Val Pro Ser Asp Val Ser
        595                 600                 605 ata agc tcc tca gag agc cag agt aac gac tcc aag acc cag tat ctg        1872
Ile Ser Ser Ser Glu Ser Gln Ser Asn Asp Ser Lys Thr Gln Tyr Leu
    610                 615                 620 ggt cga aag ctc ttc gga aac aaa agt acg ccc aaa acc cga acc ctg        1920
Gly Arg Lys Leu Phe Gly Asn Lys Ser Thr Pro Lys Thr Arg Thr Leu
625                 630                 635                 640 gaa ggc acg gct ccc cta ctc aga ata ggc gag ttt gca atc atc agt        1968
Glu Gly Thr Ala Pro Leu Leu Arg Ile Gly Glu Phe Ala Ile Ile Ser
                645                 650                 655 gca aac aac tat ccc tcc tcc aac ttc ctc gct gtt acc agt gtc aag        2016
Ala Asn Asn Tyr Pro Ser Ser Asn Phe Leu Ala Val Thr Ser Val Lys
            660                 665                 670 tcg atc gag tca agc cgg ttg gaa ggg gat tct ttg gtg ctg ctg aat        2064
Ser Ile Glu Ser Ser Arg Leu Glu Gly Asp Ser Leu Val Leu Leu Asn
        675                 680                 685 tgg cag gtg ggg gag gga cac cag aaa ggg gtc tgc tac tat ata att        2112
Trp Gln Val Gly Glu Gly His Gln Lys Gly Val Cys Tyr Tyr Ile Ile
    690                 695                 700 tat gtg aat ggc gcg gtc gtg gga ctc tca gtt gct cct aag ttt atc        2160
Tyr Val Asn Gly Ala Val Val Gly Leu Ser Val Ala Pro Lys Phe Ile
705                 710                 715                 720 tac cag gat acc gag ttg gcg tcg gag aac agt gca tct gct cgt tcg        2208
Tyr Gln Asp Thr Glu Leu Ala Ser Glu Asn Ser Ala Ser Ala Arg Ser
                725                 730                 735 aat tac aag aaa agc ggg ctt ggg tcc tcc agc gat agg aaa tca aag        2256
Asn Tyr Lys Lys Ser Gly Leu Gly Ser Ser Ser Asp Arg Lys Ser Lys
            740                 745                 750 gtg aga gtt gac tct gtc gac aaa ttg ggc aat gtt ttc acg ggg agt        2304
Val Arg Val Asp Ser Val Asp Lys Leu Gly Asn Val Phe Thr Gly Ser
        755                 760                 765 gag gtt tgg gtg tga                                                    2319
Glu Val Trp Val
    770

<210> SEQ ID NO 3
<211> LENGTH: 37
<212> TYPE: DNA
<213> ORGANISM: Artificial
<220> FEATURE:
<223> OTHER INFORMATION: Endo-Om primer(F)

<400> SEQUENCE: 3
cgatgacaag ggatcatggc gcaatctcag ctactgg                                37

<210> SEQ ID NO 4
<211> LENGTH: 35
<212> TYPE: DNA
<213> ORGANISM: Artificial
<220> FEATURE:
<223> OTHER INFORMATION: Endo-Om primer(R)

<400> SEQUENCE: 4
gcaccgtctc ggatctcaca cccaaacctc actcc                                  35
```

```
<210> SEQ ID NO 5
<211> LENGTH: 743
<212> TYPE: PRT
<213> ORGANISM: Candida parapolymorpha

<400> SEQUENCE: 5
```

| | | | | | | | | | | | | | | |
|---|---|---|---|---|---|---|---|---|---|---|---|---|---|---|
| Met | Pro | Arg | Asn | Thr | Ala | Lys | His | Ser | Ser | Leu | Pro | Gln | Thr | Asn | Leu |
| 1 | | | | 5 | | | | | 10 | | | | | 15 | |
| Pro | Leu | Ser | Ser | Leu | Glu | Ser | Ser | Phe | Phe | Asp | Ser | Leu | Asp | Glu | Leu |
| | | | 20 | | | | | 25 | | | | | 30 | | |
| Ala | Asn | Trp | Glu | Arg | Arg | Ile | His | Glu | Lys | Ser | Phe | Glu | Leu | Asp | Glu |
| | | | 35 | | | | | 40 | | | | | 45 | | |
| Leu | Asn | Lys | Pro | Thr | Glu | Lys | Leu | Ala | His | Tyr | Thr | Arg | Ala | Arg | Gln |
| | 50 | | | | | 55 | | | | | 60 | | | | |
| Gln | Ser | Thr | Ser | Glu | Asp | Val | Lys | Leu | Leu | Val | Cys | His | Asp | Leu | Lys |
| 65 | | | | | 70 | | | | | 75 | | | | | 80 |
| Gly | Gly | Tyr | Gln | Val | Asn | Glu | Asp | Glu | Asp | Pro | Leu | Gly | Tyr | Phe | Pro |
| | | | | 85 | | | | | 90 | | | | | 95 | |
| His | Pro | Asp | Gly | Gln | His | Tyr | Phe | Leu | Gln | Tyr | Pro | Gln | Leu | Val | Asp |
| | | | 100 | | | | | 105 | | | | | 110 | | |
| Lys | Phe | Val | Tyr | Phe | Ser | His | Arg | Val | Ser | Ile | Pro | Pro | Val | Ser |
| | | 115 | | | | | 120 | | | | | 125 | | | |
| Trp | Ile | Asn | Val | Cys | His | Arg | Asn | Ala | Ile | Lys | Cys | Leu | Gly | Thr | Val |
| | 130 | | | | | 135 | | | | | 140 | | | | |
| Ile | Phe | Glu | Gly | Asn | Thr | Tyr | Arg | Asp | Phe | Glu | Ala | Asp | Lys | Leu |
| 145 | | | | | 150 | | | | | 155 | | | | | 160 |
| Leu | Thr | Lys | Gln | Asp | Gly | Glu | Tyr | Val | Phe | Val | Arg | Cys | Leu | Val | Ala |
| | | | | 165 | | | | | 170 | | | | | 175 | |
| Leu | Val | Glu | Tyr | Phe | Gln | Phe | Asp | Gly | Tyr | Leu | Phe | Asn | Ile | Glu | Thr |
| | | | 180 | | | | | 185 | | | | | 190 | | |
| Arg | Phe | Ser | Asn | Thr | Arg | Ile | Ala | Ser | Leu | Leu | Glu | Pro | Phe | Leu | Glu |
| | | | 195 | | | | | 200 | | | | | 205 | | |
| Gln | Leu | Arg | Ala | Glu | Leu | His | Val | Arg | Asn | Pro | Ser | Thr | Glu | Leu | Ile |
| | 210 | | | | | 215 | | | | | 220 | | | | |
| Trp | Tyr | Asp | Ser | Tyr | Ile | Tyr | Pro | Glu | Asn | Arg | Val | Leu | Tyr | Lys | Asn |
| 225 | | | | | 230 | | | | | 235 | | | | | 240 |
| Gly | Val | Thr | Glu | Ala | Asn | Tyr | Asn | Phe | Phe | Ser | Cys | Cys | Asp | Ser | Phe |
| | | | | 245 | | | | | 250 | | | | | 255 | |
| Phe | Thr | Asn | Tyr | Trp | Trp | Asn | Val | Lys | His | Leu | Gln | Asp | Asn | Ile | Lys |
| | | | 260 | | | | | 265 | | | | | 270 | | |
| Asn | Val | Gly | Val | Leu | Gly | Ser | Arg | Leu | Lys | Val | Tyr | Ala | Gly | Tyr | Asp |
| | | 275 | | | | | 280 | | | | | 285 | | | |
| Val | Trp | Gly | Arg | Gly | Thr | Met | Ile | Gly | Lys | Gly | Tyr | Asp | Ser | Ala |
| | 290 | | | | | 295 | | | | | 300 | | | | |
| Leu | Ala | Cys | Gln | Met | Ile | Lys | Lys | Tyr | Arg | Ser | Asn | Val | Ala | Leu | Phe |
| 305 | | | | | 310 | | | | | 315 | | | | | 320 |
| Ala | Pro | Ala | Trp | Thr | Tyr | Glu | Tyr | Leu | Ala | Arg | Lys | Asp | Phe | Thr | Gln |
| | | | | 325 | | | | | 330 | | | | | 335 | |
| Asn | Asp | Thr | Arg | Phe | Trp | Ile | Gly | Leu | Phe | Asp | Gly | Glu | Ser | Ser | Met |
| | | | 340 | | | | | 345 | | | | | 350 | | |
| Ala | Thr | Thr | Phe | Lys | Pro | Tyr | Ser | Pro | Leu | Tyr | Lys | Ile | Asn | Asp |
| | | 355 | | | | | 360 | | | | | 365 | | | |
| Ser | Asn | Phe | Val | Phe | Tyr | Thr | Asn | Phe | Gly | Ser | Gly | Glu | Gly | Cys | Ala |
| | 370 | | | | | 375 | | | | | 380 | | | | |

Phe Tyr Glu Cys Gly Glu Lys Val Tyr Arg Asp Asn Trp Val Asn Gly
385                 390                 395                 400

Ser Leu Gln Met Glu Ile Pro Tyr Ala Ile His Thr Arg Asn Lys Asn
            405                 410                 415

Gly Ile Gln Trp Thr Leu Ser Lys Glu Asp Ser Phe His Gly Gly Ser
        420                 425                 430

Cys Val Glu Ile Lys Tyr Asn Glu Val Val Asp Asp Lys Gly Tyr Gln
    435                 440                 445

Val Phe Asn Asn Gln Thr Ile Asn Ser Phe Ser Leu Phe Ser Phe Val
450                 455                 460

Gln Asp Cys Ser Phe Pro Thr Val Asn Val Lys Leu Thr Tyr Lys Leu
465                 470                 475                 480

Asn His Lys Thr Lys Ser Phe Phe Lys Leu Lys Ile Gly Tyr Tyr Ile
            485                 490                 495

Glu Arg Arg Tyr Arg Thr Val Gln Lys Val Arg Ser Gly Cys Leu Val
        500                 505                 510

Val Pro Leu Leu Ser Thr Asn Asp Gln Trp Phe Thr Ile Glu Glu Pro
    515                 520                 525

Phe His Val Ser Leu Gln Asn Ser His Glu Phe Ile Val Leu Asp Ser
530                 535                 540

Ala Thr Ile Phe Tyr Glu Glu Thr Glu Asp Pro Phe Met Arg Ala His
545                 550                 555                 560

Val Val Glu Asp Gln Ser Thr Ser Ser Val Ile Asp Asn Glu Glu Tyr
            565                 570                 575

Glu Lys Leu Met Asn Ser Glu Ile Tyr Phe Asp Asp Glu Asp Glu Asp
        580                 585                 590

Trp Ile Leu Val Pro Ser Asp Ile Ser Met Glu Ser Thr Asp Asn Gly
    595                 600                 605

Gly Arg Glu Asn His Thr Trp Lys Val Ile Ser Asn Gln Ile Arg Lys
610                 615                 620

Lys His Pro Lys Ser His Pro Ser Thr Ser Pro Val Leu Lys Leu Gly
625                 630                 635                 640

Glu Leu Ala Ile Ile Asn Ala Asn Asp Tyr Pro Ser Asp Ser Phe Phe
            645                 650                 655

Lys Leu Met Pro Val Asn Ser Ile Asp Val Arg Arg Trp Glu Gly Lys
        660                 665                 670

Ile Leu Leu Ile Trp Lys Thr Asn Gln Asp Ser Val Leu Tyr His Leu
    675                 680                 685

Ile Phe Val Asp Asp Val Phe Gln Gly Ile Ser Leu Val Ser Lys Phe
690                 695                 700

Val Phe Glu Asp Gln Ala Val Asp Glu Lys Ser Phe Lys Thr Lys Ser
705                 710                 715                 720

Gly Gly Ser Thr Lys Val Arg Ile Asp Thr Val Asn Arg Leu Gly Ile
            725                 730                 735

Leu Val Lys Gly Thr Asp Met
            740

<210> SEQ ID NO 6
<211> LENGTH: 2238
<212> TYPE: DNA
<213> ORGANISM: Candida parapolymorpha
<220> FEATURE:
<221> NAME/KEY: CDS
<222> LOCATION: (1)..(2229)
<220> FEATURE:
<221> NAME/KEY: 3'UTR
<222> LOCATION: (2230)..(2235)
<220> FEATURE:
<221> NAME/KEY: terminator
<222> LOCATION: (2236)..(2238)

<400> SEQUENCE: 6

```
atg cct cga aac aca gct aaa cat tcc tcg ttg ccc caa act aat ttg      48
Met Pro Arg Asn Thr Ala Lys His Ser Ser Leu Pro Gln Thr Asn Leu
1               5                   10                  15 cct ctc tca tcc ctc gag tct tct ttc ttc gat tcc ctt gat gaa cta      96
Pro Leu Ser Ser Leu Glu Ser Ser Phe Phe Asp Ser Leu Asp Glu Leu
            20                  25                  30 gca aac tgg gaa agg cgg atc cat gag aag tcg ttt gag ctc gac gag     144
Ala Asn Trp Glu Arg Arg Ile His Glu Lys Ser Phe Glu Leu Asp Glu
        35                  40                  45 ctc aac aaa cct act gaa aaa ctc gca cat tat aca aga gca aga cag     192
Leu Asn Lys Pro Thr Glu Lys Leu Ala His Tyr Thr Arg Ala Arg Gln
    50                  55                  60 caa agc acg tca gaa gac gtt aag ctt cta gtt tgt cat gat ttg aag     240
Gln Ser Thr Ser Glu Asp Val Lys Leu Leu Val Cys His Asp Leu Lys
65                  70                  75                  80 ggc ggc tac cag gtc aac gag gat gag gac ccc cta gga tac ttc ccc     288
Gly Gly Tyr Gln Val Asn Glu Asp Glu Asp Pro Leu Gly Tyr Phe Pro
                85                  90                  95 cat ccg gac ggc cag cat tat ttc ctc cag tat ccg cag tta gtc gac     336
His Pro Asp Gly Gln His Tyr Phe Leu Gln Tyr Pro Gln Leu Val Asp
            100                 105                 110 aag ttt gtg tat ttc tct cat cat cgc gtc agt atc ccg ccg gtg tct     384
Lys Phe Val Tyr Phe Ser His His Arg Val Ser Ile Pro Pro Val Ser
        115                 120                 125 tgg atc aat gtg tgc cac cga aac gcg atc aag tgt ttg ggt act gtc     432
Trp Ile Asn Val Cys His Arg Asn Ala Ile Lys Cys Leu Gly Thr Val
    130                 135                 140 atc ttt gag ggc aac act tat cgc gac ttt gag gag gct gat aaa ttg     480
Ile Phe Glu Gly Asn Thr Tyr Arg Asp Phe Glu Glu Ala Asp Lys Leu
145                 150                 155                 160 ctc aca aag caa gac gga gag tat gtt ttt gtc aga tgc cta gtt gcg     528
Leu Thr Lys Gln Asp Gly Glu Tyr Val Phe Val Arg Cys Leu Val Ala
                165                 170                 175 ctg gtg gaa tat ttc caa ttc gat ggc tac ctt ttc aac ata gag acc     576
Leu Val Glu Tyr Phe Gln Phe Asp Gly Tyr Leu Phe Asn Ile Glu Thr
            180                 185                 190 agg ttc agc aat acg cga ata gcc agt ctt cta gag cca ttt ttg gaa     624
Arg Phe Ser Asn Thr Arg Ile Ala Ser Leu Leu Glu Pro Phe Leu Glu
        195                 200                 205 cag tta aga gct gag ctt cat gtg cga aac cca tca aca gag ctt ata     672
Gln Leu Arg Ala Glu Leu His Val Arg Asn Pro Ser Thr Glu Leu Ile
    210                 215                 220 tgg tac gac tcc tac att tac cca gaa aat agg gtt cta tac aag aat     720
Trp Tyr Asp Ser Tyr Ile Tyr Pro Glu Asn Arg Val Leu Tyr Lys Asn
225                 230                 235                 240 ggt gtt acc gag gcc aac tac aat ttt ttc tcc tgc tgt gat tcc ttt     768
Gly Val Thr Glu Ala Asn Tyr Asn Phe Phe Ser Cys Cys Asp Ser Phe
                245                 250                 255 ttc acc aac tac tgg tgg aac gtg aaa cat cta caa gat aat att aaa     816
Phe Thr Asn Tyr Trp Trp Asn Val Lys His Leu Gln Asp Asn Ile Lys
            260                 265                 270 aac gtt ggt gtt ttg gga tcc cga ctg aag gtc tat gct ggc tac gac     864
Asn Val Gly Val Leu Gly Ser Arg Leu Lys Val Tyr Ala Gly Tyr Asp
        275                 280                 285
```

-continued

| | |
|---|---|
| gta tgg gga aga ggc acg atg ata gga aaa gga ggt tat gat tcg gcc<br>Val Trp Gly Arg Gly Thr Met Ile Gly Lys Gly Gly Tyr Asp Ser Ala<br>290                            295                             300 | 912 |
| ctg gca tgc cag atg atc aag aag tac cgt tcc aat gtc gct cta ttt<br>Leu Ala Cys Gln Met Ile Lys Lys Tyr Arg Ser Asn Val Ala Leu Phe<br>305                            310                          315                       320 | 960 |
| gct cct gct tgg acc tat gaa tac ttg gct cga aaa gac ttt acc caa<br>Ala Pro Ala Trp Thr Tyr Glu Tyr Leu Ala Arg Lys Asp Phe Thr Gln<br>                        325                          330                       335 | 1008 |
| aac gat act cga ttt tgg ata ggc ctt ttt gat ggt gaa tct tcc atg<br>Asn Asp Thr Arg Phe Trp Ile Gly Leu Phe Asp Gly Glu Ser Ser Met<br>                      340                         345                       350 | 1056 |
| gcg act act ttc aag ccc tat agc tcg ccg ctt tac aaa atc aac gac<br>Ala Thr Thr Phe Lys Pro Tyr Ser Ser Pro Leu Tyr Lys Ile Asn Asp<br>355                            360                          365 | 1104 |
| tcc aat ttt gtt ttc tac acc aac ttt gga tct gga gag ggc tgt gcg<br>Ser Asn Phe Val Phe Tyr Thr Asn Phe Gly Ser Gly Glu Gly Cys Ala<br>    370                      375                       380 | 1152 |
| ttt tac gag tgc ggc gaa aaa gtg tat cgc gat aat tgg gtt aat ggt<br>Phe Tyr Glu Cys Gly Glu Lys Val Tyr Arg Asp Asn Trp Val Asn Gly<br>385                            390                          395                       400 | 1200 |
| tca ttg caa atg gaa att ccc tat gct att cac acg aga aat aaa aat<br>Ser Leu Gln Met Glu Ile Pro Tyr Ala Ile His Thr Arg Asn Lys Asn<br>                            405                          410                       415 | 1248 |
| ggg ata caa tgg acg tta tca aaa gag gac tca ttt cat ggg ggt tct<br>Gly Ile Gln Trp Thr Leu Ser Lys Glu Asp Ser Phe His Gly Gly Ser<br>                      420                         425                       430 | 1296 |
| tgt gtg gag atc aaa tac aat gaa gtc gtt gac gat aaa ggc tac caa<br>Cys Val Glu Ile Lys Tyr Asn Glu Val Val Asp Asp Lys Gly Tyr Gln<br>                            435                          440                       445 | 1344 |
| gta ttc aac aac cag acg att aat tcg ttc tcg tta ttt tca ttt gtc<br>Val Phe Asn Asn Gln Thr Ile Asn Ser Phe Ser Leu Phe Ser Phe Val<br>450                            455                          460 | 1392 |
| cag gat tgt tct ttc cca acg gta aac gtg aaa ttg acc tac aag ctg<br>Gln Asp Cys Ser Phe Pro Thr Val Asn Val Lys Leu Thr Tyr Lys Leu<br>465                            470                          475                       480 | 1440 |
| aac cat aag acc aag tct ttt ttc aag ctc aaa att ggc tac tat att<br>Asn His Lys Thr Lys Ser Phe Phe Lys Leu Lys Ile Gly Tyr Tyr Ile<br>                        485                          490                       495 | 1488 |
| gaa cgg cgc tat aga act gtt cag aag gtg aga agt gga tgt ctg gtg<br>Glu Arg Arg Tyr Arg Thr Val Gln Lys Val Arg Ser Gly Cys Leu Val<br>                      500                         505                       510 | 1536 |
| gtt cca ttg ctt tca aca aac gat caa tgg ttc aca ata gaa gaa ccg<br>Val Pro Leu Leu Ser Thr Asn Asp Gln Trp Phe Thr Ile Glu Glu Pro<br>                        515                          520                       525 | 1584 |
| ttc cat gta agt ttg cag aat tca cat gaa ttc ata gtc ctg gat tcg<br>Phe His Val Ser Leu Gln Asn Ser His Glu Phe Ile Val Leu Asp Ser<br>530                            535                          540 | 1632 |
| gct aca ata ttc tac gaa gag act gaa gat cca ttc atg cgc gcg cac<br>Ala Thr Ile Phe Tyr Glu Glu Thr Glu Asp Pro Phe Met Arg Ala His<br>545                            550                          555                       560 | 1680 |
| gtg gtt gaa gat cag tcg acc tca agt gtt atc gac aac gag gaa tac<br>Val Val Glu Asp Gln Ser Thr Ser Ser Val Ile Asp Asn Glu Glu Tyr<br>                        565                          570                       575 | 1728 |
| gag aaa cta atg aat agc gag ata tat ttc gat gac gaa gat gag gac<br>Glu Lys Leu Met Asn Ser Glu Ile Tyr Phe Asp Asp Glu Asp Glu Asp<br>                      580                         585                       590 | 1776 |
| tgg att ctc gtc cct tct gac atc tca atg gaa tca acc gat aac gga<br>Trp Ile Leu Val Pro Ser Asp Ile Ser Met Glu Ser Thr Asp Asn Gly<br>                        595                          600                       605 | 1824 |

```
gga agg gaa aat cat aca tgg aaa gtg atc agc aat caa ata cgc aaa    1872
Gly Arg Glu Asn His Thr Trp Lys Val Ile Ser Asn Gln Ile Arg Lys
        610                 615                 620 aaa cac ccg aaa tcg cat cct tcc aca tcg cct gta cta aag ctg gga    1920
Lys His Pro Lys Ser His Pro Ser Thr Ser Pro Val Leu Lys Leu Gly
625                 630                 635                 640 gaa ctc gct atc ata aat gcc aat gac tac cca tca gac agt ttt ttc    1968
Glu Leu Ala Ile Ile Asn Ala Asn Asp Tyr Pro Ser Asp Ser Phe Phe
                645                 650                 655 aag ctt atg ccg gta aac tcc att gat gtt agg cgg tgg gaa ggt aag    2016
Lys Leu Met Pro Val Asn Ser Ile Asp Val Arg Arg Trp Glu Gly Lys
            660                 665                 670 atc ttg cta ata tgg aaa acg aat cag gat tca gtt ctt tac cat cta    2064
Ile Leu Leu Ile Trp Lys Thr Asn Gln Asp Ser Val Leu Tyr His Leu
        675                 680                 685 ata ttt gtt gat gat gtg ttt caa ggc ata tcg tta gtg tcc aag ttt    2112
Ile Phe Val Asp Asp Val Phe Gln Gly Ile Ser Leu Val Ser Lys Phe
690                 695                 700 gtc ttc gaa gat cag gcg gtt gac gaa aag agt ttc aag aca aaa tct    2160
Val Phe Glu Asp Gln Ala Val Asp Glu Lys Ser Phe Lys Thr Lys Ser
705                 710                 715                 720 gga ggc tct acg aaa gtg agg att gat acc gtc aac aga ctt gga ata    2208
Gly Gly Ser Thr Lys Val Arg Ile Asp Thr Val Asn Arg Leu Gly Ile
                725                 730                 735 ctt gtc aag ggt acc gat atg cacatttga                              2238
Leu Val Lys Gly Thr Asp Met
            740

<210> SEQ ID NO 7
<211> LENGTH: 34
<212> TYPE: DNA
<213> ORGANISM: Artificial
<220> FEATURE:
<223> OTHER INFORMATION: Endo-Cp primer F

<400> SEQUENCE: 7
tcgaaggtag gcatatgcct cgaaacacag ctaa                              34

<210> SEQ ID NO 8
<211> LENGTH: 39
<212> TYPE: DNA
<213> ORGANISM: Artificial
<220> FEATURE:
<223> OTHER INFORMATION: Endo-Cp primer R

<400> SEQUENCE: 8
gcttgaattc ggatcctcaa atgtgcatat cggtaccct                         39

<210> SEQ ID NO 9
<211> LENGTH: 656
<212> TYPE: PRT
<213> ORGANISM: Pichia anomala

<400> SEQUENCE: 9

Met Gln His Asp His Ala Ala Ile Lys Phe Glu Glu Asp Ser Ile Ser
1               5                   10                  15

Ser Gln Arg Phe Ser Ser Leu Asp Glu Val Glu Lys Trp Tyr Asn Thr
            20                  25                  30

Lys Asn Arg Ser Pro Leu Asp Asp Leu Arg Ile Pro Arg Glu Ser Leu
        35                  40                  45

Ser His Tyr Asn Arg Phe Arg Asp Asn Asn Asp Glu Ile Lys Val Leu
```

-continued

```
            50                  55                  60
Val Cys His Asp Phe Lys Gly Asn Tyr Gln Glu Gly Glu Asp Glu Asn
 65                      70                  75                  80

Pro Leu Gly Tyr Phe Pro His Ser Ser Gly Gln His Tyr Phe Ile Gln
                     85                  90                  95

Phe Pro Ser Leu Val Asp Leu Phe Ile Phe Ser His Tyr Lys Ile
                100                 105                 110

Ala Val Pro Pro Val Ser Trp Ile Asn Ser Leu His Arg Gln Gly Ile
            115                 120                 125

Pro Val Leu Gly Thr Leu Ile Phe Glu Gly Thr Asp Val Ser Glu Ser
            130                 135                 140

Asp Lys Leu Leu Glu Lys Asn Glu Asn Gly Asp Phe Lys Tyr Leu Glu
145                 150                 155                 160

Ile Leu Cys Glu Leu Val Arg His Tyr Gly Phe Asp Gly Trp Leu Val
                165                 170                 175

Asn Met Glu Ser His Phe Ser Ser Val Ala Lys Ala Gln Asp Leu Leu
                180                 185                 190

Leu Phe Asp Glu Ala Leu Arg Ser Thr Leu His Leu Lys Val Pro Gly
            195                 200                 205

Ser Lys Leu Ile Trp Tyr Asp Ser Leu Ile Thr Gln Lys Asn Arg Val
    210                 215                 220

Phe Tyr Gln Asn Ala Val Asn Glu Trp Asn Tyr Asp His Phe Ser Thr
225                 230                 235                 240

Ser Asp Leu Phe Phe Thr Asn Tyr Trp Trp Asn Glu Glu Asp Leu Lys
                245                 250                 255

Arg Asn Ile Leu Asn Ile Gly Leu Gln Gly Val Lys Gln Lys Leu Phe
                260                 265                 270

Val Gly Val Asp Ile Trp Gly Arg Gly Ser Arg Ile Gly Asn Gly Gly
            275                 280                 285

Phe Glu Ser Gly Leu Ala Ile Asn Tyr Leu Lys Arg Tyr Ser Thr Asn
            290                 295                 300

Val Ala Leu Phe Ala Pro Ala Trp Thr Tyr Glu Asn Phe Glu Glu Asp
305                 310                 315                 320

Gln Phe Leu Ile Lys Asp Arg Lys Phe Trp Ile Gly Asp Gln Thr Ser
                325                 330                 335

Asp Glu Thr Gly Gly Ser Val Ala Thr Tyr Val Ser His Tyr Thr Thr
            340                 345                 350

Pro Val Tyr Val Lys Asp Gln Asn Val Lys Phe Tyr Thr Asn Phe Ser
            355                 360                 365

Val Gly Glu Gly Thr Lys Tyr Arg Val Phe Ala His Thr Val Phe Lys
    370                 375                 380

Asn Asn Trp Val Asn Gly Asn Leu Gln Leu Pro Thr Pro Ile Ile Asp
385                 390                 395                 400

Asn Glu Lys Arg Ile Asp Ile Tyr Tyr Lys Glu Ser Phe Asn Gly Gly
                405                 410                 415

Ser Ser Leu Lys Val Thr Gln Arg Asn Ser Ile Leu Asn Asp Gly Lys
            420                 425                 430

Ser Asn Ile Leu Gln Leu Phe Ser Phe Lys Asn Asp Ile His Ser Asn
            435                 440                 445

Asn Leu Asn Val Ser Val Ser Phe Lys Tyr Leu Ser Glu Ile Pro Leu
    450                 455                 460

Asn Ser Thr Phe Gln Leu Glu Ile Lys Phe Tyr Ile Glu Arg Arg Tyr
465                 470                 475                 480
```

```
Arg Ser Val Thr Arg Val Arg Asp Gly Thr Phe Lys Leu Pro Leu Ala
                485                 490                 495

Phe Ser Asn Lys Asn Trp Lys Tyr Ile Glu Thr Ser Phe Ala Leu Pro
            500                 505                 510

Arg Leu Gln Ile Arg Glu His Phe Val Leu Glu Gly Leu Gln Ile Arg
        515                 520                 525

Trp Val Asp Asn Val Asp Glu Leu Ser Ser Ile Gly Thr Ser Gly
    530                 535                 540

Asp Phe Thr Glu Ser Trp Ile Ile Val Pro Gln Asn Ser Asp Pro Asn
545                 550                 555                 560

Ala Val Tyr Glu Leu Leu Ile Gly Asp Leu Val Glu Gly Ile Lys
                565                 570                 575

Thr Ala Asn Gly Asn Ile Asp Ala Val Thr Lys Leu Ser Arg Lys Ile
            580                 585                 590

Thr Leu Asp Ser Arg Ser Ile Leu Ala Thr Trp Lys Asp Asp Thr Glu
        595                 600                 605

Val Leu Tyr Trp Ile Ile Tyr Val Asn Ala Lys Phe Leu Gly Ile Ala
    610                 615                 620

His Lys Ser Leu Trp Arg Val Gln Arg Gly Asp Lys Leu Arg Val Asp
625                 630                 635                 640

Val Phe Thr Arg Ser Gly Lys Leu Val Lys Gly Glu Asp Ile Phe Ile
                645                 650                 655

<210> SEQ ID NO 10
<211> LENGTH: 1971
<212> TYPE: DNA
<213> ORGANISM: Pichia anomala
<220> FEATURE:
<221> NAME/KEY: CDS
<222> LOCATION: (1)..(1968)
<220> FEATURE:
<221> NAME/KEY: terminator
<222> LOCATION: (1969)..(1971)

<400> SEQUENCE: 10 atg caa cat gat cat gct gcc ata aag ttt gaa gaa gac tcg att tcc      48
Met Gln His Asp His Ala Ala Ile Lys Phe Glu Glu Asp Ser Ile Ser
1               5                   10                  15 agc caa agg ttt agc agc ttg gat gaa gtg gaa aaa tgg tac aat act      96
Ser Gln Arg Phe Ser Ser Leu Asp Glu Val Glu Lys Trp Tyr Asn Thr
            20                  25                  30 aaa aac agg agc cca tta gac gac ttg agg att cca agg gaa tca tta     144
Lys Asn Arg Ser Pro Leu Asp Asp Leu Arg Ile Pro Arg Glu Ser Leu
        35                  40                  45 tca cac tat aat cgt ttt aga gac aac aat gat gag ata aaa gtt cta     192
Ser His Tyr Asn Arg Phe Arg Asp Asn Asn Asp Glu Ile Lys Val Leu
    50                  55                  60 gtt tgt cat gat ttc aaa ggc aat tat caa gaa ggt gaa gat gaa aat     240
Val Cys His Asp Phe Lys Gly Asn Tyr Gln Glu Gly Glu Asp Glu Asn
65                  70                  75                  80 cca tta ggt tat ttt cct cat tca tct ggt caa cat tat ttc atc cag     288
Pro Leu Gly Tyr Phe Pro His Ser Ser Gly Gln His Tyr Phe Ile Gln
                85                  90                  95 ttt cct tct ttg gtt gat tta ttc atc ttt ttt tct cat tac aaa att     336
Phe Pro Ser Leu Val Asp Leu Phe Ile Phe Phe Ser His Tyr Lys Ile
            100                 105                 110 gca gta cca cca gtg tct tgg ata aat tca ttg cat aga caa gga ata     384
Ala Val Pro Pro Val Ser Trp Ile Asn Ser Leu His Arg Gln Gly Ile
        115                 120                 125
```

```
cca gtg ctt ggt act tta att ttt gag ggt aca gat gtc tct gaa tct      432
Pro Val Leu Gly Thr Leu Ile Phe Glu Gly Thr Asp Val Ser Glu Ser
    130                 135                 140 gat aaa ttg ttg gaa aag aat gag aat gga gac ttc aaa tat ttg gaa      480
Asp Lys Leu Leu Glu Lys Asn Glu Asn Gly Asp Phe Lys Tyr Leu Glu
145                 150                 155                 160 att ctt tgt gaa ttg gta cgg cat tat gga ttt gat ggt tgg ttg gtt      528
Ile Leu Cys Glu Leu Val Arg His Tyr Gly Phe Asp Gly Trp Leu Val
                165                 170                 175 aac atg gag tct cac ttc agc tcc gtg gca aaa gct caa gac ctt ttg      576
Asn Met Glu Ser His Phe Ser Ser Val Ala Lys Ala Gln Asp Leu Leu
            180                 185                 190 tta ttt gac gaa gct ttg aga tca aca ctt cac tta aaa gtc cct ggt      624
Leu Phe Asp Glu Ala Leu Arg Ser Thr Leu His Leu Lys Val Pro Gly
        195                 200                 205 tca aag cta ata tgg tat gat tca ttg att aca caa aag aat aga gtt      672
Ser Lys Leu Ile Trp Tyr Asp Ser Leu Ile Thr Gln Lys Asn Arg Val
    210                 215                 220 ttc tat caa aat gca gtc aat gaa tgg aat tat gat cat ttt tcc acc      720
Phe Tyr Gln Asn Ala Val Asn Glu Trp Asn Tyr Asp His Phe Ser Thr
225                 230                 235                 240 tca gat ctg ttc ttc aca aat tat tgg tgg aat gaa gaa gat ttg aaa      768
Ser Asp Leu Phe Phe Thr Asn Tyr Trp Trp Asn Glu Glu Asp Leu Lys
                245                 250                 255 aga aat att ttg aat att ggt ctg caa ggt gtt aag cag aaa ttg ttt      816
Arg Asn Ile Leu Asn Ile Gly Leu Gln Gly Val Lys Gln Lys Leu Phe
            260                 265                 270 gtt ggt gtt gat att tgg ggg aga ggc tca aga ata ggc aat gga ggg      864
Val Gly Val Asp Ile Trp Gly Arg Gly Ser Arg Ile Gly Asn Gly Gly
        275                 280                 285 ttt gaa agt ggt cta gct ata aat tat ttg aaa aga tac tca aca aac      912
Phe Glu Ser Gly Leu Ala Ile Asn Tyr Leu Lys Arg Tyr Ser Thr Asn
    290                 295                 300 gtg gca ttg ttt gca cca gca tgg act tac gag aat ttt gaa gag gac      960
Val Ala Leu Phe Ala Pro Ala Trp Thr Tyr Glu Asn Phe Glu Glu Asp
305                 310                 315                 320 caa ttt ttg atc aaa gat cga aaa ttt tgg att ggt gat caa aca agc     1008
Gln Phe Leu Ile Lys Asp Arg Lys Phe Trp Ile Gly Asp Gln Thr Ser
                325                 330                 335 gat gag aca gga ggt agt gtt gca act tat gtt tcc cat tac acc acg     1056
Asp Glu Thr Gly Gly Ser Val Ala Thr Tyr Val Ser His Tyr Thr Thr
            340                 345                 350 cca gtc tat gtg aag gat cag aat gtt aag ttt tat acg aat ttt agt     1104
Pro Val Tyr Val Lys Asp Gln Asn Val Lys Phe Tyr Thr Asn Phe Ser
        355                 360                 365 gtt ggt gaa gga aca aag tac aga gtt ttt gca cac act gtt ttc aaa     1152
Val Gly Glu Gly Thr Lys Tyr Arg Val Phe Ala His Thr Val Phe Lys
    370                 375                 380 aac aac tgg gtg aat ggt aac ctg caa ctt cct aca cca atc att gat     1200
Asn Asn Trp Val Asn Gly Asn Leu Gln Leu Pro Thr Pro Ile Ile Asp
385                 390                 395                 400 aat gaa aaa cgg att gat att tac tat aag gaa tca ttt aat ggt ggt     1248
Asn Glu Lys Arg Ile Asp Ile Tyr Tyr Lys Glu Ser Phe Asn Gly Gly
                405                 410                 415 tca agt ttg aaa gta aca caa aga aat tct att ttg aat gat ggg aaa     1296
Ser Ser Leu Lys Val Thr Gln Arg Asn Ser Ile Leu Asn Asp Gly Lys
            420                 425                 430 tcc aac att ctc cag tta ttc tca ttc aaa aat gat ata cac tct aat     1344
Ser Asn Ile Leu Gln Leu Phe Ser Phe Lys Asn Asp Ile His Ser Asn
```

-continued

```
                       435                 440                 445
aat cta aac gtt tca gtg agc ttc aag tac ttg tca gaa att ccg ctc      1392
Asn Leu Asn Val Ser Val Ser Phe Lys Tyr Leu Ser Glu Ile Pro Leu
450                 455                 460 aat tca act ttc cag cta gaa atc aag ttt tac att gaa cga aga tat      1440
Asn Ser Thr Phe Gln Leu Glu Ile Lys Phe Tyr Ile Glu Arg Arg Tyr
465                 470                 475                 480 agg agt gtt act agg gtt aga gat ggg act ttt aag ttg cca ttg gca      1488
Arg Ser Val Thr Arg Val Arg Asp Gly Thr Phe Lys Leu Pro Leu Ala
                485                 490                 495 ttt tct aac aaa aat tgg aag tat att gaa aca tca ttt gca ctt cca      1536
Phe Ser Asn Lys Asn Trp Lys Tyr Ile Glu Thr Ser Phe Ala Leu Pro
            500                 505                 510 agg tta caa ata agg gaa cat ttc gta ttg gag ggg ctt cag ata cga      1584
Arg Leu Gln Ile Arg Glu His Phe Val Leu Glu Gly Leu Gln Ile Arg
        515                 520                 525 tgg gtt gat aat gta gat gaa tta agc tct tca att ggc aca tct ggt      1632
Trp Val Asp Asn Val Asp Glu Leu Ser Ser Ser Ile Gly Thr Ser Gly
    530                 535                 540 gac ttt acg gaa tct tgg att att gtt cct caa aat agt gac cca aat      1680
Asp Phe Thr Glu Ser Trp Ile Ile Val Pro Gln Asn Ser Asp Pro Asn
545                 550                 555                 560 gct gta tat gaa ttg ctt atc ggg gat tta ttg gtt gaa ggt atc aaa      1728
Ala Val Tyr Glu Leu Leu Ile Gly Asp Leu Leu Val Glu Gly Ile Lys
                565                 570                 575 acg gca aac gga aat ata gat gct gtc acc aaa ctt tct agg aag atc      1776
Thr Ala Asn Gly Asn Ile Asp Ala Val Thr Lys Leu Ser Arg Lys Ile
            580                 585                 590 act ttg gat tct agg agt ata ctt gca aca tgg aaa gat gat act gaa      1824
Thr Leu Asp Ser Arg Ser Ile Leu Ala Thr Trp Lys Asp Asp Thr Glu
        595                 600                 605 gtg ctt tac tgg atc att tat gtg aat gca aag ttc tta gga att gca      1872
Val Leu Tyr Trp Ile Ile Tyr Val Asn Ala Lys Phe Leu Gly Ile Ala
    610                 615                 620 cac aaa tct tta tgg aga gtt caa aga ggt gac aaa ttg aga gtt gac      1920
His Lys Ser Leu Trp Arg Val Gln Arg Gly Asp Lys Leu Arg Val Asp
625                 630                 635                 640 gtt ttc act agg tca gga aag ctc gtc aaa ggc gag gat ata ttt ata      1968
Val Phe Thr Arg Ser Gly Lys Leu Val Lys Gly Glu Asp Ile Phe Ile
                645                 650                 655 tag                                                                  1971
```

<210> SEQ ID NO 11
<211> LENGTH: 38
<212> TYPE: DNA
<213> ORGANISM: Artificial
<220> FEATURE:
<223> OTHER INFORMATION: Endo-Pa prime F

<400> SEQUENCE: 11
tcgaaggtag gcatatgcaa catgatcatg ctgccata                            38

<210> SEQ ID NO 12
<211> LENGTH: 41
<212> TYPE: DNA
<213> ORGANISM: Artificial
<220> FEATURE:
<223> OTHER INFORMATION: Endo-Pa primer R

<400> SEQUENCE: 12
gcttgaattc ggatccctat ataaatatat cctcgccttt g                        41

<210> SEQ ID NO 13
<211> LENGTH: 639
<212> TYPE: PRT
<213> ORGANISM: Zygosaccharomyces rouxii

<400> SEQUENCE: 13

```
Met Lys Arg Ile Asn Gln Val Pro Gly Lys Pro Glu Ile Thr Ser Leu
1               5                   10                  15

Tyr Phe Asp Asp Leu Asn Ser Leu Gln Arg Trp Phe Asp Lys Gly Phe
            20                  25                  30

Met Asp Ser Arg Asp Leu Ser Asn Val Pro Lys Glu Arg Tyr Ser Asn
        35                  40                  45

Tyr Val Lys Phe Glu Lys Asp Ser Ile Ile Thr Ile Pro Asn Leu Ser
    50                  55                  60

Ala Arg Lys Thr Glu Ile Ile Val Cys His Asp Phe Lys Gly Gly Tyr
65                  70                  75                  80

Gln Ser Gly His Asp Leu Tyr Pro Asn Gly Tyr Gly Thr Glu Ser
            85                  90                  95

Cys Lys Pro Tyr Ser Leu Arg Tyr Pro Glu Ile Val Asp Lys Phe Val
        100                 105                 110

Tyr Phe Ser His His Cys Val Thr Ile Pro Pro Ser Pro Trp Thr Asn
    115                 120                 125

Tyr Leu His Arg His Ser Ile Pro Val Leu Gly Thr Leu Ile Leu Glu
130                 135                 140

His Tyr Pro His Asn Gly Glu Leu Phe Lys Lys Asn Ala Lys Gly Glu
145                 150                 155                 160

Phe Leu Tyr Val Lys Tyr Leu Val Glu Leu Cys Arg Lys Phe His Phe
            165                 170                 175

Glu Gly Trp Leu Ile Asn Phe Glu Thr Val Phe Gly Asn Asn Ser Lys
        180                 185                 190

Gln Val Ile Pro Phe Leu Arg Glu Leu Thr Ala Arg Val Glu Cys Glu
    195                 200                 205

Ile Tyr Gly Gly Ser Val Ile Trp Tyr Asp Ala Phe Thr Thr Phe Ser
210                 215                 220

Asn Lys Pro Ser His Gln Asn Glu Val Asn Leu Phe Asn Tyr Asp Ala
225                 230                 235                 240

Tyr Glu Asn Ser Ser Gln Phe Met Thr Asn Tyr Met Trp Asp Ser His
            245                 250                 255

Asn Val Gly Asn Ser Leu Arg Asn Val Gly Ala Leu Gly Met His Ser
        260                 265                 270

His Val Ala Leu Gly Val Asp Val Trp Gly Arg Asn Met Gln Val Cys
    275                 280                 285

Arg Gly Gly Phe Glu Ser Asn Ile Ala Ile Tyr Tyr Ala Lys Arg Phe
290                 295                 300

Gly Thr Asn Ala Val Ile Phe Ala Pro Gly Trp Thr Tyr Glu Asn Phe
305                 310                 315                 320

Gly Glu Asp Gln Phe Tyr Glu Lys Asp Ile Phe Trp Gly Asn Ile
            325                 330                 335

Lys Ser Thr Leu Gln Leu Asp Ser Tyr Ser Asp Ser Gln Leu Ser Ser
        340                 345                 350

Trp Phe Val Ser Glu Ser Lys Lys Thr Arg Tyr Phe Thr Thr Phe Phe
    355                 360                 365

Ser Thr Gly Ser Gly Asn Phe Phe Asn Leu Asn Gly Arg Arg Ile Ser
```

```
                370             375             380
Asn Asp Asn Trp Val Gln Leu Gly Leu Ser Thr Pro Phe Pro Val Asn
385                 390                 395                 400

Ser His Ser Tyr Leu Ser Phe Lys Asp Ser Phe Val Gly Gly Ser Cys
                405                 410                 415

Leu Ala Leu Pro Leu Ser Pro Met Glu Asn Gly Lys Leu His Leu Phe
                420                 425                 430

Arg Phe Glu Gln Phe Ile Lys Asp Gln Gln Lys Thr Ser Asp Ser Glu
                435                 440                 445

Ile Arg Val Lys Leu Ser Tyr Lys Ser Leu Gly Ala Leu Pro Pro Val
            450                 455                 460

Lys Leu Val Ile Lys Cys Phe Val Ile Arg Arg Gly Lys Arg Ser Lys
465                 470                 475                 480

Thr Ile Leu Lys Val Asp Asp Val Ser Leu Val Leu Pro Leu Ser His
                485                 490                 495

Ser Ala Cys Gln Thr Ala Gln Gly Ser Thr Lys Trp Ala Val Val Glu
                500                 505                 510

Gln Ile Val Pro Leu Pro Ser Leu Glu Ser Arg Phe Leu Glu Glu Tyr
                515                 520                 525

Tyr Val Glu Asp Ala His Leu Glu Trp Thr Met Asp Asn Asn His Asp
                530                 535                 540

Glu Trp Leu Met Val Pro Glu Arg Thr Glu Asp Leu Asp Cys Lys Leu
545                 550                 555                 560

Leu Ile Gly Ser Leu Cys Leu Glu Ile Gly Pro His Glu Asp Asn Asn
                565                 570                 575

Lys Arg Gln Ile Val Arg Asn Gly Pro Gln Leu Ser Trp Gln Asp Asn
                580                 585                 590

Glu Ser Ser Phe Met Trp Leu Lys Leu Gln Asp Gly Lys Leu Asp Ser
                595                 600                 605

Val Leu Phe Thr Pro Thr Thr Lys Val Asn Gly Lys Gln Pro Thr Ile
                610                 615                 620

Leu Glu Cys Gly Arg Asn Gly Thr Leu Lys Phe Val Val Lys Lys
625                 630                 635

<210> SEQ ID NO 14
<211> LENGTH: 1920
<212> TYPE: DNA
<213> ORGANISM: Zygosaccharomyces rouxii
<220> FEATURE:
<221> NAME/KEY: CDS
<222> LOCATION: (1)..(1917)
<220> FEATURE:
<221> NAME/KEY: terminator
<222> LOCATION: (1918)..(1920)

<400> SEQUENCE: 14 atg aaa cgt att aat cag gtt ccc ggc aaa cct gaa att aca tct ctt      48
Met Lys Arg Ile Asn Gln Val Pro Gly Lys Pro Glu Ile Thr Ser Leu
1               5                   10                  15 tat ttc gat gat tta aac tca tta caa cga tgg ttc gat aag ggg ttt      96
Tyr Phe Asp Asp Leu Asn Ser Leu Gln Arg Trp Phe Asp Lys Gly Phe
                20                  25                  30 atg gat tcc aga gac ctg tca aat gtt ccg aag gaa aga tat tcg aat     144
Met Asp Ser Arg Asp Leu Ser Asn Val Pro Lys Glu Arg Tyr Ser Asn
            35                  40                  45 tat gtt aaa ttt gaa aag gat agc ata att acg att ccc aac tta tcc     192
Tyr Val Lys Phe Glu Lys Asp Ser Ile Ile Thr Ile Pro Asn Leu Ser
        50                  55                  60
```

```
gct cgt aaa act gaa att ata gtc tgc cat gat ttt aaa ggt ggt tat    240
Ala Arg Lys Thr Glu Ile Ile Val Cys His Asp Phe Lys Gly Gly Tyr
65              70                  75                  80 caa tcg gga cat gat ctc tat ccg aat ggt cag tat gga acg gag tct    288
Gln Ser Gly His Asp Leu Tyr Pro Asn Gly Gln Tyr Gly Thr Glu Ser
                85                  90                  95 tgt aag cca tat tca ttg agg tat cca gag att gtg gat aaa ttc gtc    336
Cys Lys Pro Tyr Ser Leu Arg Tyr Pro Glu Ile Val Asp Lys Phe Val
            100                 105                 110 tat ttt tcg cat cat tgt gtc acc atc ccg cct tca cct tgg act aat    384
Tyr Phe Ser His His Cys Val Thr Ile Pro Pro Ser Pro Trp Thr Asn
        115                 120                 125 tac ttg cat aga cac agt ata ccc gtg cta gga act tta atc tta gaa    432
Tyr Leu His Arg His Ser Ile Pro Val Leu Gly Thr Leu Ile Leu Glu
    130                 135                 140 cat tat cct cac aat ggt gaa ttg ttc aag aaa aat gca aag ggg gaa    480
His Tyr Pro His Asn Gly Glu Leu Phe Lys Lys Asn Ala Lys Gly Glu
145                 150                 155                 160 ttc ctg tat gtg aaa tat ctt gtt gaa ctt tgt cgc aaa ttc cac ttt    528
Phe Leu Tyr Val Lys Tyr Leu Val Glu Leu Cys Arg Lys Phe His Phe
                165                 170                 175 gaa ggg tgg ttg atc aat ttt gag act gta ttt ggg aat aat tca aag    576
Glu Gly Trp Leu Ile Asn Phe Glu Thr Val Phe Gly Asn Asn Ser Lys
            180                 185                 190 caa gta att cca ttc ctt agg gaa tta acc gct cgt gtg gaa tgt gag    624
Gln Val Ile Pro Phe Leu Arg Glu Leu Thr Ala Arg Val Glu Cys Glu
        195                 200                 205 atc tat ggt ggg agt gta ata tgg tat gat gca ttc acc acg ttt tca    672
Ile Tyr Gly Gly Ser Val Ile Trp Tyr Asp Ala Phe Thr Thr Phe Ser
    210                 215                 220 aac aag cca agt cat caa aac gaa gtg aat ctt ttc aat tac gat gct    720
Asn Lys Pro Ser His Gln Asn Glu Val Asn Leu Phe Asn Tyr Asp Ala
225                 230                 235                 240 tat gaa aac tcg agt caa ttt atg aca aat tac atg tgg gat tct cat    768
Tyr Glu Asn Ser Ser Gln Phe Met Thr Asn Tyr Met Trp Asp Ser His
                245                 250                 255 aat gtt ggc aac tct tta aga aat gtt ggt gca tta gga atg cat tct    816
Asn Val Gly Asn Ser Leu Arg Asn Val Gly Ala Leu Gly Met His Ser
            260                 265                 270 cat gtg gca ctt ggt gtg gat gtt tgg ggt cgc aat atg cag gtt tgt    864
His Val Ala Leu Gly Val Asp Val Trp Gly Arg Asn Met Gln Val Cys
        275                 280                 285 cgc ggt ggt ttt gaa agt aac att gca att tac tat gca aaa agg ttt    912
Arg Gly Gly Phe Glu Ser Asn Ile Ala Ile Tyr Tyr Ala Lys Arg Phe
    290                 295                 300 ggc acc aat gca gtt ata ttt gca cca gga tgg aca tat gaa aat ttt    960
Gly Thr Asn Ala Val Ile Phe Ala Pro Gly Trp Thr Tyr Glu Asn Phe
305                 310                 315                 320 ggt gag gat caa ttt tat gaa aaa gat gat ata ttt tgg ggt aat att   1008
Gly Glu Asp Gln Phe Tyr Glu Lys Asp Asp Ile Phe Trp Gly Asn Ile
                325                 330                 335 aaa agt act tta caa tta gac tct tat tct gat tct caa ttg tca tca   1056
Lys Ser Thr Leu Gln Leu Asp Ser Tyr Ser Asp Ser Gln Leu Ser Ser
            340                 345                 350 tgg ttc gtt tct gaa tcc aag aaa acc aga tat ttt acc act ttt ttc   1104
Trp Phe Val Ser Glu Ser Lys Lys Thr Arg Tyr Phe Thr Thr Phe Phe
        355                 360                 365 tct act ggt tca gga aac ttc ttt aat cta aat ggt aga agg att tcc   1152
Ser Thr Gly Ser Gly Asn Phe Phe Asn Leu Asn Gly Arg Arg Ile Ser
```

```
aac gac aat tgg gtt caa ctg ggt ctc tca aca cca ttt cca gtt aac      1200
Asn Asp Asn Trp Val Gln Leu Gly Leu Ser Thr Pro Phe Pro Val Asn
385                 390                 395                 400 agc cat tct tat ttg agt ttc aaa gat tcc ttt gtc ggc ggt agt tgc      1248
Ser His Ser Tyr Leu Ser Phe Lys Asp Ser Phe Val Gly Gly Ser Cys
                405                 410                 415 cta gcg tta cct ctt tcg ccc atg gaa aat ggc aag ttg cat ctt ttc      1296
Leu Ala Leu Pro Leu Ser Pro Met Glu Asn Gly Lys Leu His Leu Phe
            420                 425                 430 aga ttt gag caa ttt att aaa gat caa caa aag act tct gat agt gaa      1344
Arg Phe Glu Gln Phe Ile Lys Asp Gln Gln Lys Thr Ser Asp Ser Glu
        435                 440                 445 atc aga gtt aaa tta tct tac aaa tca ttg gga gca ttg ccg ccg gtt      1392
Ile Arg Val Lys Leu Ser Tyr Lys Ser Leu Gly Ala Leu Pro Pro Val
    450                 455                 460 aaa cta gtg atc aaa tgt ttt gtc att cgt cgc ggc aaa agg tca aag      1440
Lys Leu Val Ile Lys Cys Phe Val Ile Arg Arg Gly Lys Arg Ser Lys
465                 470                 475                 480 aca att ttg aaa gtg gac gat gtg tca cta gtg tta cct tta agt cat      1488
Thr Ile Leu Lys Val Asp Asp Val Ser Leu Val Leu Pro Leu Ser His
                485                 490                 495 agt gcc tgt caa aca gca caa ggc tct act aag tgg gcg gtg gtt gaa      1536
Ser Ala Cys Gln Thr Ala Gln Gly Ser Thr Lys Trp Ala Val Val Glu
            500                 505                 510 caa atc gtt cca tta cca agt ctg gaa tca aga ttt ttg gag gaa tat      1584
Gln Ile Val Pro Leu Pro Ser Leu Glu Ser Arg Phe Leu Glu Glu Tyr
        515                 520                 525 tat gtg gaa gat gcg cat tta gaa tgg aca atg gat aat aac cat gat      1632
Tyr Val Glu Asp Ala His Leu Glu Trp Thr Met Asp Asn Asn His Asp
    530                 535                 540 gag tgg cta atg gtt cca gaa aga aca gag gat tta gat tgt aaa tta      1680
Glu Trp Leu Met Val Pro Glu Arg Thr Glu Asp Leu Asp Cys Lys Leu
545                 550                 555                 560 ttg ata gga tca ctt tgt ctt gaa att ggt cct cat gaa gat aac aat      1728
Leu Ile Gly Ser Leu Cys Leu Glu Ile Gly Pro His Glu Asp Asn Asn
                565                 570                 575 aaa agg caa ata gta aga aat gga cct caa tta agt tgg caa gat aat      1776
Lys Arg Gln Ile Val Arg Asn Gly Pro Gln Leu Ser Trp Gln Asp Asn
            580                 585                 590 gaa agc tct ttc atg tgg tta aag cta caa gat ggt aaa ctt gat agc      1824
Glu Ser Ser Phe Met Trp Leu Lys Leu Gln Asp Gly Lys Leu Asp Ser
        595                 600                 605 gtc tta ttt aca cca aca aca aaa gta aac ggt aaa caa ccc acg att      1872
Val Leu Phe Thr Pro Thr Thr Lys Val Asn Gly Lys Gln Pro Thr Ile
    610                 615                 620 ttg gaa tgt ggg agg aat ggt act ttg aaa ttc gta gtc aag aag taa      1920
Leu Glu Cys Gly Arg Asn Gly Thr Leu Lys Phe Val Val Lys Lys
625                 630                 635
```

<210> SEQ ID NO 15
<211> LENGTH: 34
<212> TYPE: DNA
<213> ORGANISM: Artificial
<220> FEATURE:
<223> OTHER INFORMATION: Endo-Zr primer F

<400> SEQUENCE: 15
tcgaaggtag gcatatgaaa cgtattaatc aggt         34

```
<210> SEQ ID NO 16
<211> LENGTH: 42
<212> TYPE: DNA
<213> ORGANISM: Artificial
<220> FEATURE:
<223> OTHER INFORMATION: Endo-Zr primer R

<400> SEQUENCE: 16
gcttgaattc ggatccttac ttcttgacta cgaatttcaa ag                    42
```